United States Patent
Church et al.

(10) Patent No.: US 11,293,052 B2
(45) Date of Patent: *Apr. 5, 2022

(54) COMPOSITIONS AND METHODS FOR ANALYTE DETECTION

(71) Applicant: President and Fellows of Harvard College, Cambridge, MA (US)

(72) Inventors: George M. Church, Brookline, MA (US); Jehyuk Lee, Allston, MA (US); Daniel Levner, Boston, MA (US); Michael Super, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/238,682

(22) Filed: Apr. 23, 2021

(65) Prior Publication Data

US 2021/0254131 A1   Aug. 19, 2021

Related U.S. Application Data

(63) Continuation of application No. 16/941,585, filed on Jul. 29, 2020, now Pat. No. 11,021,737, which is a continuation-in-part of application No. 16/157,243, filed on Oct. 11, 2018, now Pat. No. 11,078,520, which is a continuation of application No. 14/774,282, filed as application No. PCT/US2014/018580 on Feb. 26, 2014, now Pat. No. 10,138,509, said application No. 16/941,585 is a continuation-in-part of application No. 16/393,215, filed on Apr. 24, 2019, which is a continuation of application No. 16/255,920, filed on Jan. 24, 2019, now abandoned, which is a continuation of application No. 14/366,486, filed as application No. PCT/US2012/071398 on Dec. 21, 2012, now Pat. No. 10,227,639.

(60) Provisional application No. 61/777,383, filed on Mar. 12, 2013, provisional application No. 61/579,265, filed on Dec. 22, 2011.

(51) Int. Cl.
| | |
|---|---|
| *C12Q 1/6806* | (2018.01) |
| *C12Q 1/6844* | (2018.01) |
| *C12Q 1/6869* | (2018.01) |
| *C12Q 1/6874* | (2018.01) |
| *C12P 19/34* | (2006.01) |

(52) U.S. Cl.
CPC ............ *C12Q 1/6806* (2013.01); *C12P 19/34* (2013.01); *C12Q 1/6844* (2013.01); *C12Q 1/6869* (2013.01); *C12Q 1/6874* (2013.01)

(58) Field of Classification Search
CPC .. C12Q 1/6806; C12Q 1/6844; C12Q 1/6869; C12Q 1/6874; C12Q 2565/50; C12Q 2565/158; C12P 19/34
See application file for complete search history.

(56) References Cited

U.S. PATENT DOCUMENTS

| | | |
|---|---|---|
| 4,123,610 A | 10/1978 | Summerton et al. |
| 4,844,617 A | 7/1989 | Kelderman et al. |
| 4,886,741 A | 12/1989 | Schwartz |
| 4,981,985 A | 1/1991 | Kaplan et al. |
| 5,151,189 A | 9/1992 | Hu et al. |
| 5,563,056 A | 10/1996 | Swan et al. |
| 5,594,235 A | 1/1997 | Lee |
| 5,695,940 A | 12/1997 | Drmanac et al. |
| 5,830,708 A | 11/1998 | Naughton |
| 5,834,758 A | 11/1998 | Trulson et al. |
| 5,871,921 A | 2/1999 | Landegren et al. |
| 6,068,979 A | 5/2000 | Akhavan-Tafti |
| 6,083,726 A | 7/2000 | Mills, Jr. et al. |
| 6,194,148 B1 | 2/2001 | Hori et al. |
| 6,306,597 B1 | 10/2001 | Macevicz |
| 6,534,266 B1 | 3/2003 | Singer |
| 6,586,176 B1 | 7/2003 | Trnovsky et al. |
| 6,632,655 B1 | 10/2003 | Mehta et al. |
| 7,255,994 B2 | 8/2007 | Lao |
| 7,323,305 B2 | 1/2008 | Leamon et al. |
| 7,427,479 B2 | 9/2008 | Karger et al. |
| 7,473,767 B2 | 1/2009 | Dimitrov |
| 7,745,129 B1 | 6/2010 | Schatz |
| 7,771,949 B2 | 8/2010 | Kramer |
| 7,906,285 B2 | 3/2011 | Drmanac |
| 7,910,304 B2 | 3/2011 | Drmanac |
| 7,941,279 B2 | 5/2011 | Hwang et al. |
| 8,013,134 B2 | 9/2011 | Fredriksson |
| 8,124,751 B2 | 2/2012 | Pierce et al. |
| 8,268,554 B2 | 9/2012 | Schallmeiner |
| 8,329,404 B2 | 12/2012 | McKernan et al. |
| 8,415,102 B2 | 4/2013 | Geiss et al. |
| 8,431,691 B2 | 4/2013 | McKernan et al. |
| 8,460,865 B2 | 6/2013 | Chee et al. |

(Continued)

FOREIGN PATENT DOCUMENTS

| | | |
|---|---|---|
| BR | 112015013784 A2 | 7/2017 |
| BR | 112015013785 A2 | 7/2017 |

(Continued)

OTHER PUBLICATIONS

Al-Attar et al., Clustered Regularly Interspaced Short Palindromic Repeats (CRISPRs): The Hallmark of an Ingenious Antiviral Defense Mechanism in Prokaryotes, Bioi Chem. (20 11) vol. 392, Issue 4, pp. 277-289.

(Continued)

*Primary Examiner* — David C Thomas
(74) *Attorney, Agent, or Firm* — Banner & Witcoff, Ltd.

(57) ABSTRACT

Methods of making a three-dimensional matrix of nucleic acids within a cell is provided.

82 Claims, 14 Drawing Sheets

Specification includes a Sequence Listing.

(56) References Cited

U.S. PATENT DOCUMENTS

| | | |
|---|---|---|
| 8,501,459 B2 | 8/2013 | Chen et al. |
| 8,519,115 B2 | 8/2013 | Webster et al. |
| 8,551,710 B2 | 10/2013 | Bernitz et al. |
| 8,658,361 B2 | 2/2014 | Wu et al. |
| 8,697,359 B1 | 4/2014 | Zhang |
| 8,871,445 B2 | 10/2014 | Cong et al. |
| 8,906,616 B2 | 12/2014 | Zhang et al. |
| 8,932,814 B2 | 1/2015 | Cong et al. |
| 8,946,389 B2 | 2/2015 | Gao et al. |
| 8,986,926 B2 | 3/2015 | Ferree et al. |
| 8,993,233 B2 | 3/2015 | Zhang et al. |
| 8,999,641 B2 | 4/2015 | Zhang et al. |
| 9,017,992 B2 | 4/2015 | Winther et al. |
| 9,201,063 B2 | 12/2015 | Sood et al. |
| 9,217,151 B2 | 12/2015 | Yin et al. |
| 9,257,135 B2 | 2/2016 | Ong et al. |
| 9,267,135 B2 | 2/2016 | Church et al. |
| 9,371,563 B2 | 6/2016 | Geiss et al. |
| 9,371,598 B2 | 6/2016 | Chee |
| 9,714,446 B2 | 7/2017 | Webster et al. |
| 9,714,937 B2 | 7/2017 | Dunaway |
| 9,896,720 B2 | 2/2018 | Raj et al. |
| 10,030,261 B2 | 7/2018 | Frisen et al. |
| 10,138,509 B2 | 11/2018 | Church et al. |
| 10,227,639 B2 | 3/2019 | Levner et al. |
| 10,266,888 B2 | 4/2019 | Daugharthy et al. |
| 10,267,808 B2 | 4/2019 | Cai |
| 10,465,235 B2 | 11/2019 | Gullberg et al. |
| 10,494,662 B2 | 12/2019 | Church et al. |
| 10,494,667 B2 | 12/2019 | Chee |
| 10,501,791 B2 | 12/2019 | Church et al. |
| 10,545,075 B2 | 1/2020 | Deisseroth et al. |
| 11,021,737 B2 | 6/2021 | Church et al. |
| 2002/0015952 A1 | 2/2002 | Anderson et al. |
| 2002/0155989 A1 | 10/2002 | Efimov et al. |
| 2002/0172950 A1 | 11/2002 | Kenny et al. |
| 2003/0148335 A1 | 8/2003 | Shen et al. |
| 2003/0165852 A1 | 9/2003 | Schueler et al. |
| 2004/0077014 A1 | 4/2004 | Becker |
| 2004/0248144 A1 | 12/2004 | Mir |
| 2004/0259190 A1 | 12/2004 | Naughton |
| 2005/0106629 A1 | 5/2005 | McGrath et al. |
| 2005/0147981 A1 | 7/2005 | Yamakawa et al. |
| 2005/0191687 A1 | 9/2005 | Wang et al. |
| 2005/0233318 A1 | 10/2005 | Chee et al. |
| 2006/0024711 A1 | 2/2006 | Lapidus et al. |
| 2006/0077536 A1 | 4/2006 | Bromage et al. |
| 2006/0177833 A1 | 8/2006 | Brenner |
| 2006/0183107 A1 | 8/2006 | Melkonyan et al. |
| 2006/0216339 A1 | 9/2006 | Ambron et al. |
| 2006/0228733 A1 | 10/2006 | Pierce et al. |
| 2006/0234261 A1 | 10/2006 | Pierce et al. |
| 2006/0248349 A1 | 11/2006 | Rathjen et al. |
| 2006/0292611 A1 | 12/2006 | Berka et al. |
| 2007/0020650 A1 | 1/2007 | Kahvejian |
| 2007/0087362 A1 | 4/2007 | Church et al. |
| 2007/0117109 A1 | 5/2007 | Rothemund |
| 2007/0117177 A1 | 5/2007 | Luo et al. |
| 2007/0206275 A1 | 9/2007 | Hemmer et al. |
| 2007/0231823 A1 | 10/2007 | McKernan et al. |
| 2007/0292877 A1 | 12/2007 | Dimitrov |
| 2008/0050718 A1 | 2/2008 | Gesteland et al. |
| 2008/0176769 A1 | 7/2008 | Rank et al. |
| 2008/0269068 A1 | 10/2008 | Church et al. |
| 2009/0005259 A1 | 1/2009 | Drmanac |
| 2009/0208965 A1 | 8/2009 | Tafas et al. |
| 2009/0220968 A1 | 9/2009 | Issadore et al. |
| 2009/0246879 A1 | 10/2009 | Drmanac et al. |
| 2010/0009868 A1 | 1/2010 | Yan et al. |
| 2010/0047924 A1 | 2/2010 | Webster et al. |
| 2010/0076057 A1 | 3/2010 | Sontheimer et al. |
| 2010/0087325 A1 | 4/2010 | Buermann |
| 2010/0151472 A1 | 6/2010 | Nolan et al. |
| 2010/0223276 A1 | 9/2010 | Al-Shameri et al. |
| 2010/0268478 A1 | 10/2010 | Andregg et al. |
| 2011/0020291 A1 | 1/2011 | Banerjee et al. |
| 2011/0033520 A1 | 2/2011 | Mather et al. |
| 2011/0086774 A1 | 4/2011 | Dunaway |
| 2011/0092376 A1 | 4/2011 | Colston, Jr. et al. |
| 2011/0104693 A1 | 5/2011 | Seligmann |
| 2011/0189776 A1 | 8/2011 | Terns et al. |
| 2011/0223585 A1 | 9/2011 | Gullberg et al. |
| 2011/0223638 A1 | 9/2011 | Wiedenheft et al. |
| 2011/0245111 A1 | 10/2011 | Chee |
| 2011/0257031 A1 | 10/2011 | Bodeau et al. |
| 2011/0294135 A1 | 12/2011 | Carlson |
| 2012/0040397 A1 | 2/2012 | Luo et al. |
| 2012/0122712 A1 | 5/2012 | Goldstein |
| 2012/0126142 A1 | 5/2012 | Matsui et al. |
| 2012/0252686 A1 | 10/2012 | Umbarger et al. |
| 2012/0330636 A1 | 12/2012 | Albou |
| 2013/0017229 A1 | 1/2013 | Mooney et al. |
| 2013/0130248 A1 | 5/2013 | Haurwitz et al. |
| 2013/0245096 A1 | 9/2013 | Abitbol |
| 2013/0253040 A1 | 9/2013 | Miller et al. |
| 2013/0323729 A1 | 12/2013 | Landegren et al. |
| 2014/0049632 A1 | 2/2014 | Hemmer |
| 2014/0068797 A1 | 3/2014 | Doudna et al. |
| 2014/0087378 A1 | 3/2014 | Chatre et al. |
| 2014/0087427 A1 | 3/2014 | Bujnicki et al. |
| 2014/0179006 A1 | 6/2014 | Zhang |
| 2014/0179770 A1 | 6/2014 | Zhang et al. |
| 2014/0200146 A1 | 7/2014 | Xie et al. |
| 2014/0220578 A1 | 8/2014 | Bohannon et al. |
| 2014/0220587 A1 | 8/2014 | Green, Jr. et al. |
| 2014/0270435 A1 | 9/2014 | Dunn |
| 2014/0273226 A1 | 9/2014 | Wu |
| 2014/0273233 A1 | 9/2014 | Chen et al. |
| 2014/0310830 A1 | 10/2014 | Zhang et al. |
| 2014/0315985 A1 | 10/2014 | May et al. |
| 2014/0342457 A1 | 11/2014 | Mali et al. |
| 2015/0004598 A1 | 1/2015 | Gao et al. |
| 2015/0133319 A1 | 5/2015 | Fu et al. |
| 2015/0247150 A1 | 9/2015 | Zhang et al. |
| 2015/0267251 A1 | 9/2015 | Cai et al. |
| 2016/0002704 A1 | 1/2016 | Diehl et al. |
| 2016/0024524 A1 | 1/2016 | Joung et al. |
| 2016/0024555 A1 | 1/2016 | Church et al. |
| 2016/0153006 A1 | 6/2016 | Zhang et al. |
| 2016/0160210 A1 | 6/2016 | Mali et al. |
| 2016/0253584 A1 | 9/2016 | Fodor et al. |
| 2016/0265046 A1 | 9/2016 | Zhang et al. |
| 2016/0289740 A1 | 10/2016 | Fu et al. |
| 2016/0340662 A1 | 11/2016 | Zhang et al. |
| 2016/0355795 A1 | 12/2016 | Ran et al. |
| 2016/0358326 A1 | 12/2016 | Sarachan et al. |
| 2017/0176338 A1 | 6/2017 | Wu et al. |
| 2017/0191078 A1 | 7/2017 | Zhang et al. |
| 2017/0212983 A1 | 7/2017 | Cai et al. |
| 2018/0010166 A1 | 1/2018 | Pierce et al. |
| 2018/0051322 A1 | 2/2018 | Church et al. |
| 2018/0282787 A1 | 10/2018 | Walter et al. |
| 2020/0090786 A1 | 3/2020 | Quiroz Zarate et al. |

FOREIGN PATENT DOCUMENTS

| | | |
|---|---|---|
| BR | 112015008708 A2 | 9/2017 |
| BR | 112015012375 A2 | 9/2017 |
| BR | 112015014425 A2 | 10/2017 |
| BR | 112015022061 A2 | 11/2017 |
| CA | 2891347 A1 | 6/2014 |
| CN | 1580283 A | 2/2005 |
| CN | 1959384 A | 5/2007 |
| CN | 101553306 A | 10/2009 |
| EP | 2878671 A1 | 6/2015 |
| JP | H04-268359 A | 9/1992 |
| JP | 2012-170337 A | 9/2012 |
| JP | 2014-513523 A | 6/2014 |
| KR | 20080003402 A | 1/2008 |
| WO | 9746704 A1 | 12/1997 |
| WO | 98/56955 A1 | 12/1998 |
| WO | 01/26708 A1 | 4/2001 |
| WO | 01/37266 A1 | 5/2001 |
| WO | 2003044229 A1 | 5/2003 |

(56) References Cited

FOREIGN PATENT DOCUMENTS

| | | | |
|---|---|---|---|
| WO | 2004/104645 | A2 | 12/2004 |
| WO | 2006/138257 | A2 | 12/2006 |
| WO | 2007/001986 | A2 | 1/2007 |
| WO | 2007076128 | A2 | 7/2007 |
| WO | 2007086900 | A2 | 8/2007 |
| WO | 2007/121489 | A2 | 10/2007 |
| WO | 2007/123744 | A2 | 11/2007 |
| WO | 2007/149696 | A1 | 12/2007 |
| WO | 2008069973 | A2 | 6/2008 |
| WO | 2008/108989 | A2 | 9/2008 |
| WO | 2008157696 | A2 | 12/2008 |
| WO | 2009/046149 | A1 | 4/2009 |
| WO | 2009/046348 | A1 | 4/2009 |
| WO | 2010/054108 | A2 | 5/2010 |
| WO | 2010080134 | A1 | 7/2010 |
| WO | 2010/087325 | A1 | 8/2010 |
| WO | 2011/143124 | A2 | 11/2011 |
| WO | 2011/143583 | A1 | 11/2011 |
| WO | 2012005595 | A2 | 1/2012 |
| WO | 2012/058638 | A2 | 5/2012 |
| WO | 2012/110899 | A2 | 8/2012 |
| WO | 2012150035 | A1 | 11/2012 |
| WO | 2012/164565 | A1 | 12/2012 |
| WO | 2013/055995 | A2 | 4/2013 |
| WO | 2013/098244 | A1 | 7/2013 |
| WO | 2013/126794 | A1 | 8/2013 |
| WO | 2013/141680 | A1 | 9/2013 |
| WO | 2013/142578 | A1 | 9/2013 |
| WO | 2013176772 | A1 | 11/2013 |
| WO | 2014/022702 | A2 | 2/2014 |
| WO | 2014/048083 | A1 | 4/2014 |
| WO | 2014/065596 | A1 | 5/2014 |
| WO | 2014/089290 | A1 | 6/2014 |
| WO | 2014/093595 | A1 | 6/2014 |
| WO | 2014/093622 | A2 | 6/2014 |
| WO | 2014/093661 | A2 | 6/2014 |
| WO | 2014/093694 | A1 | 6/2014 |
| WO | 2014/099744 | A1 | 6/2014 |
| WO | 2014/113493 | A1 | 7/2014 |
| WO | 2014/144288 | A1 | 9/2014 |
| WO | 2014/150624 | A1 | 9/2014 |
| WO | 2014/0163886 | A1 | 10/2014 |
| WO | 2014/182528 | A2 | 11/2014 |
| WO | 2014/191518 | A1 | 12/2014 |
| WO | 2014/197568 | A2 | 12/2014 |
| WO | 2015/118029 | A1 | 8/2015 |
| WO | 2015/127183 | A2 | 8/2015 |
| WO | 2016081740 | A1 | 5/2016 |
| WO | 2017/161251 | A1 | 9/2017 |

OTHER PUBLICATIONS

Carroll, "A CRISPR Approach to Gene Targeting" 20(9) Molecular Therapy 1658-1660 (Sep. 2012).

Jinek, et al. 'RNA-programmed genome editing in human cells.' eLite 2013;2:e00471. [retrieved 1-3, 6, 7, 10-12 on Jun. 3, 2014). Retrieved from the Internet. <URL: http://elife.elifesciences.org/content/2/e00471 >. entire document.

Hale et al., Essential Features and Rational Design of CRISPR RNAs That Function With the Cas RAMP Module Complex to Cleave RNAs, Molecular Cell, (20 12) vol. 45, Issue 3, 292-302.

Hatoum-Aslan, et al. 'Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. Dec. 2011. entire document.

Makarova et al., "Evolution and classification of the CRISPR-Cas systems" 9(6) Nature Reviews Microbiology 467-477 (1-23) (Jun. 2011).

Rho, Mina et al. 'Diverse CRISPRs Evolving in Human Microbiomes.' PLoS Genetics. Vol. 8, No. 6. 1-14 pp. 1-12. Jun. 2012. entire document.

Sontheimer Erik, Project 7: Establishing RNA-Directed DNA Targeting in Eukaryotic Cells; Project dates: Nov. 16, 2011 to Dec. 31, 2012 (Feb. 4, 2012).

Wiedenheft eta!., "RNA-guided genetic silencing systems in bacteria and archaea" 482 Nature 331-338 (Feb. 16, 2012).

Liu et al., Cell-Penetrating Peptide-Mediated Delivery of TALEN Proteins via Bioconjugation for Genome Engineering, PLOS ONE, 2014, vol. 9(1), pp. 1-7.

Ramakrishna et al., Gene disruption by cell-penetrating peptide-mediated delivery of Cas9 protein and guide RNA, Genome Res. published online Apr. 2, 2014, pp. 1-20 plus figures.

The Delivery Problem, Nature Biotechnology, 2006, vol. 24(3), pp. 305-306.

Ansari et al., Riboactivators: Transcription activation by non-coding RNA, Grit Rev Biochem Mol Bioi. 2009 ; 44(1 ): 50-61.

Sapranauskas et al (Nucleic Acids Research, 2011, 39:9275-9282).

U.S. Appl. No. 61/794,422, filed Mar. 15, 2013, Davis, G. et al.

U.S. Appl. No. 61/781,598, filed Mar. 14, 2013, Haurwitz, R.

Gilbert, Luke A., et al.,"CRISPR-Mediated Modular RNA-Guided Regulation of Transcription in Eukaryotes," Cell, vol. 154, No. 2, Jul. 1, 2013 (Jul. 1, 2013), pp. 442-451.

Mali, P. et al., "Supplementary Materials for RNA-Guided Human Genome Engineering via Cas9," Science, vol. 339, No. 6121, Jan. 3, 2013 (Jan. 3, 2013), pp. 1-36.

Maeder, Morgan L., et al.,"Robust, synergistic regulation of human gene expression using TALE activators," HHS Public Access Author Manuscript, vol. 10, No. 3, Feb. 10, 2013 (Feb. 10, 2013), pp. 243-245.

Perez-Pinera, Pablo, et al., "Synergistic and tunable human gene activation by combinations of synthetic transcription factors," Nature Methods, vol. 10. No. 3, Feb. 3, 2013 (Feb. 3, 2013), pp. 239-242.

Preliminary Office Action issued by Brazilian Patent Office dated Apr. 7, 2020.

Official Notification dated May 24, 2020 for IL 242959.

Jun. 2, 2020—(JP) Notice of Reasons for Rejection for App. No. 2019-039027.

Jul. 3, 2020—(AU) Examination Report for App. No. 20202039777.

Aug. 19, 2020—(MX) Office Action—App. No. MX/a/2015/016798.

Sep. 10, 2020—(CA) Office Action—App. No. 2,914,638.

Sep. 21, 2020—(NZ) First Examination Report—App. No. 715280.

Sep. 21, 2020—(NZ) First Examination Report—App. No. 753950.

Fu et al., "Improving CRISPR-Cas nuclease specificity using truncated guide RNAs," Nature Biotechnology, vol. 32, pp. 249-284 (Jan. 26, 2014).

Lin et al., "CRISPR/Cas9 systems have off-target activity with insertions or deletions between target DNA and guide RNA sequences," Nucleic Acids Research, vol. 42, No. 11, pp. 7473-7485 (May 16, 2014).

Sep. 21, 2020—(NZ) First Examination Report—App. No. 753951.

Sep. 25, 2020—(RU) Office Action—App. No. 2019114706.

DiCarlo et al., "Genome engineering in *Saccharomyces cerevisiae* using CRISPR-Cas systems," Nucleic Acids Research, vol. 41, No. 7, pp. 4336-4343 (2013).

Gusev et al. "Rolling Circle Amplification: A New Approach to Increase Sensitivity for Immunohistochemistry and Flow Cyometry" American Journal of Pathology, vol. 159, No. 1, Jul. 2001, pp. 63-69.

Nov. 10, 2020—U.S. Non-Final Office Action—U.S. Appl. No. 16/285,292.

Pihlak et al. "Rapid genome sequencing with short universal tiling probes" Nature Biotechnology, vol. 26, No. 6, Jun. 2008, pp. 676-684.

Lizardi "Next-generation sequencing-by-hybridization" Nature Biotechnology, vol. 26, No. 6, Jun. 2008, pp. 649-650.

Mignardi et al. "Fourth-generation sequencing in the cell and the clinic" Genome Medicine, 2014, 6:31.

Dec. 24, 2020—U.S. Notice of Allowance—U.S. Appl. No. 16/393,215.

Terry R, Porreca G, McCarthy K, Church GM. 2008. Polonator Instrument http://www.polonator.org; Wayback Machine (Aug. 7, 2008) "Open, Affordable, Sequencing . . .".

(56) References Cited

OTHER PUBLICATIONS

Terry R, Porreca G, McCarthy K, Church GM. 2008. Polonator Instrument http://www.polonator.org; Wayback Machine (Aug. 7, 2008) "The Vision".
Terry R, Porreca G, McCarthy K, Church GM. 2008. Polonator Instrument http://www.polonator.org; Wayback Machine (Aug. 7, 2008) "The Polonator Ecosystem".
Terry R, Porreca G, McCarthy K, Church GM. 2008. Polonator Instrument http://www.polonator.org; Wayback Machine (Aug. 7, 2008) "Instrument Overview".
Terry R, Porreca G, McCarthy K, Church GM. 2008. Polonator Instrument http://www.polonator.org; Wayback Machine (Aug. 7, 2008) "Protocols".
Terry R, Porreca G, McCarthy K, Church GM. 2008. Polonator Instrument http://www.polonator.org; Wayback Machine (Sep. 5, 2008) "PET (Paired End-Tag) Genomic Shotgun Library Construction Protocol".
Terry R, Porreca G, McCarthy K, Church GM. 2008. Polonator Instrument http://www.polonator.org; Wayback Machine (Sep. 5, 2008) "Emulsion PCR Protocol".
Terry R, Porreca G, McCarthy K, Church GM. 2008. Polonator Instrument http://www.polonator.org; Wayback Machine (Sep. 5, 2008) "Emulsion Breaking Protocol".
Terry R, Porreca G, McCarthy K, Church GM. 2008. Polonator Instrument http://www.polonator.org; Wayback Machine (Sep. 5, 2008) "Bead Enrichment Protocol".
Terry R, Porreca G, McCarthy K, Church GM. 2008. Polonator Instrument http://www.polonator.org; Wayback Machine (Sep. 5, 2008) "Bead Capping Protocol".
Terry R, Porreca G, McCarthy K, Church GM. 2008. Polonator Instrument http://www.polonator.org; Wayback Machine (Sep. 5, 2008) "Coverslip Aminosilanation and Arraying Protocol".
Weibrecht, Irene et al., "Simultaneous Visualization of Both Signaling Cascade Activity and End-Point Gene Expression in Single Cells", PLOS ONE, vol. 6, No. 5, May 25, 2011 (May 25, 2011).
Larsson, Chatarina; Grundberg, Ida; Sbderberg, Ola; Nilsson, Mats: 11 In situ detection and genotyping of individual mRNA molecules, Nature Methods, vol. 7, No. 5 Apr. 11, 2010 (Apr. 11, 2010), pp. 395-397, XP055035168, DOI: 10.1038/nmeth.1448 Retrieved from the Internet: URL:http://www.nature.com/nmeth/journal/v7/n5/pdf/nmeth.1448.pdf [retrieved on Aug. 9, 2012] * the whole document *.
Nuovo: "Co-labeling Using In Situ PCR: A Review" Journal of Histochemistry & Cytochemistry, vol. 49, No. 11, Nov. 1, 2001 (Nov. 1, 2001), pp. 1329-1339, XP055164942, ISSN: 0022-1554, DOI: 10.1177/002215540104901101 * the whole document *.
Mitra R. D. et al: 11 In situ localized amplification and contact replication of many individual DNA molecules 11 Nucleic Acids Research, Information Retrieval Ltd, GB, vol. 27, No. 24, Dec. 15, 1999 (Dec. 15, 1999), p. e34, XP002292358, ISSN: 0305-1048, DOI: 10.1093/NAR/27.24.E34 * abstract *.
Ke et al: 11 In situ sequencing for RNA analysis in preserved tissue and cells 11 Nature Methods, vol. 10, No. 9, Jul. 14, 2013 (Jul. 14, 2013), pp. 857-860, XP055163946, ISSN: 1548-7091, DOI: 10.1038/nmeth.2563 * the whole document *.
Lee et al: "Highly Multiplexed Subcellular RNA Sequencing in Situ", Science, vol. 343, No. 6177, Feb. 27, 2014 (Feb. 27, 2014), pp. 1360-1363, XP055305772, us ISSN: 0036-8075, DOI: 10.1126/science.1250212.
Clausson et al: "Compaction of rolling circle amplification products increases signal integrity and signal-to-noise ratio", Scientific Reports, vol. 5, Jul. 23, 2015 (Jul. 23, 2015), p. 12317, XP055305777, DOI: 10.1038/srep12317.
Nadji et al.,"Photochemically and Photoenzymatically Cleavable DNA," J. Am. Chem. Soc. 1992, 114, 9266-9269.
Extended European Search Report and Written Opinion dated Dec. 17, 2019 for EP 19180827.8.
Supplementary European Search Report and Written Opinion dated Mar. 18, 2020.
Chen et al., "Expansion microscopy," Science, vol. 347, No. 6221, pp. 543-548 (Jan. 30, 2015).
Chozinski et al., "Expansion microscopy with conventional antibodies and fluorescent proteins," Nature Methods, vol. 13, No. 6, pp. 485-488 (Jun. 1, 2016).
Chen et al., "Nanoscale imaging of RNA with expansion microscopy," Nature Methods, vol. 133, No. 8, pp. 679-684 (Aug. 1, 2016).
Supplementary European Search Report dated Apr. 9, 2020 for EP 17847555.
Amasino, "Acceleration of nucleic acid hybridization rate by polyethylene glycol," Analytical Biochemistry, vol. 152, No. 2, pp. 304-307 (Feb. 1, 1986).
Bouché et al., "The effect of spermidine on endonuclease inhibition by agarose contaminants," Analytical Biochemistry, vol. 115, No. 1, pp. 42-45 (Jul. 15, 1981).
Kuznetsova et al., "What Macromolecular Crowding Can Do to a Protein," Int. J. Mol. Sci., vol. 15, No. 12, pp. 23090-23140 (Dec. 1, 2014).
Oupicky et al., "Laterally stabilized complexes of DNA with linear reducible polycations: Strategy for triggered intracellular actication of DNA delivery vectors," Journal of the American Chemical Society, vol. 124, No. 1, pp. 8-9 (Jan. 9, 2002).
Nguyen, Son C., "Strategies for Studying Chromatin Regulation and Organization," Doctoral Dissertation, Harvard University (May 1, 2018); retrieved from https://dash.harvard.edu/bitstream/handle/1/33493431/NGUYEN-DISSERTATION-2016.pdf?sequence=4&isAllowed=y on Apr. 8, 2020.
Zhou et al. "In Situ Detection of Messenger RNA Using Digoxigenin-Labeled Oligonucleotides and Rolling Circle Amplification" Experimental and Molecular Pathology 70, 281-288 (2001).
May 29, 2020—Examination Report issued for EP 18173059.9.
Jun. 1, 2020—Examination Report issued for GB 1809029.0.
Wright et al., "Dynamic closed-loop system for focus tracking using a spatial light modulator and a deformable membrane mirror," Optics Express, vol. 14, No. 1, pp. 222-228 (Jan. 9, 2006).
Wang et al., "The method of axial drift compensation of laser differential confocal microscopy based on zero-tracking," Proc. of SPIE, vol. 9618, 96180X (2015).
Ohata et al., "Confocal Imaging Analysis of Intracellular Ions in Mixed Cellular Systems or in Situ Using Two Types of Confocal Microscopic Systems," Methods in Enzymology, vol. 307, pp. 425-441 (1999), particularly p. 437.
Supplemental Material for Schweitzer et al. (PNAS 2000; 97(18):10113-10119) (Year: 2000).
Aug. 3, 2020—U.S. Non-Final Office Action—U.S. Appl. No. 16/157,243.
Aug. 3, 2020—U.S. Non-Final Office Action—U.S. Appl. No. 16/393,215.
Jul. 2, 2020—U.S. Non-Final Office Action—U.S. Appl. No. 16/255,920.
Aug. 10, 2020—(GB) Examination Report—GB App. No. 1809029.0.
Sep. 24, 2020—U.S. Final Office Action—U.S. Appl. No. 15/772,652.
Markaki et al. "Fluorescence In Situ Hybridization Applications for Super-Resolution 3D Structured Illumination Microscopy" Methods in Microbiology, Jan. 2013.
Achim et al. "High-throughput spatial mapping of single-cell RNA-seq data to tissue of origin" Nature Biotechnology, Apr. 13, 2015.
Sep. 25, 2020—U.S. Non-Final Office Action—U.S. Appl. No. 16/386,337.
Aug. 25, 2020—(JP) Notice of Reasons for Rejection—App. No. 2018-522985.
Pi: Piezo Nano Positioning, 2008 (online), retrieved on Aug. 12, 2020, pp. 1-6 <https://www.pi-usa.us/fileadmin/user_upload/pi_us/files/product_datasheets/N725_Piezo_Focus_Positioner.pdf>.
Sep. 14, 2020—(CA) Examination Report—App. No. 2,850,509.
Mali, P. et al. RNA-Guided Human Genome Engineering Via Cas9. Science. Jan. 3, 2013,vol. 339; pp. 823-826; abstract; p. 823, second column, second to third paragraph; p. 823, third column, second paragraph to third paragraph; figure 1; Supplementary material, p. 4, first paragraph; p. 7, first paragraph; Supplementary figures S1, S3. DOI: 10.1126/science.1232033.

(56) References Cited

OTHER PUBLICATIONS

Tiley, LS et al. The VP16 Transcription Activation Domain Is Functional When Targeted To A Promoter-Proximal RNA Sequence. Genes and Development. 1992. vol. 6; pp. 2077-2087; abstract; p. 2077, first column, first paragraph.
Trafton, A. Editing The Genome With High Precision [online]. MIT News office. Jan. 3, 2013 [retrieved on Dec. 4, 2014). Retrieved from the Internet: <URL:http:/lnewsoffice.Trafton .edut20 13/editing-the-genome-with-high-precision-01 03 >;pp. 1-3; p. 3, third paragraph.
Leman, AR et al. The Replication Forie Understanding The Eukaryotic Replication Machinery And The Challenges To Genome Duplication. Genes Jan. 29, 2013. vol 4; pp. 1-32; figure 1; DOI: 10.3390/genes4010001.
Qi, L et al. Repurposing CRISPR As An RNA-Guided Platform For Sequence-Specific Control Of Gene Expression. Cell. Feb. 28, 2013. vol. 152; pp. 1173-1183; figures 2, 4. DOI: 10.1 016/j.cell. 2013.02.022.
Gasiunas, G et aL Cas9-crRNA Ribonucleoprotein Complex Mediates Specific DNA Cleavage For Adaptive Immunity In Bacteria. PNAS. Sep. 4, 2012. vol. 109, No. 39; pp. E2579-E2586; p. E2583, first column, first paragraph. DOI: 1 0.1073/pnas.1208507109.
Cong, Let al. Multiplex Genome Engineering Using CRISPR/Cas Systems. Science. Jan. 3, 2013, vol. 339; pp. 819-823; abstract; p. 821, third column; p. 822, first column, first paragraph; figure 4. DOI: 10.1126/science.1231143.
Jinek, M et al. A Programmable Dual-RNA-Guided DNA Endonuclease In Adaptive Bacterial Immunity. Science. Jun. 28, 2012. vol. 337; pp. 816-821; DOI: 10.1126/science.1225829.
CRISPR In The Lab: A Practical Guide [online]. Addgene. Sep. 4, 2014. Retrieved on Dec. 4, 2014. Retrieved from the Internet: <URL: https://www.addgene.org/CRISPR/guide/>.
Cheng, AW et al. Multiplexed Activation Of Endogenous Genes By CRISP R-on, An RNA-Guided Transcriptional Activator System. Cell Research Aug. 27, 2013. vol. 23; pp. 1163-1171. DOI: 10.1038/cr.2013.122.
Mali, P. et al. CAS9 Transcriptional Activators For Target Specificity Screening And Paired Nickases For Cooperative Genome Engineering. Nature Biotechnology. Aug. 1, 2013. vol. 31; pp. 833-838; entire document. DOI: 10.1038/nbt.2675.
Ran, FA et al. Double Nicking By RNA-Guided CRISPR Cas9 For Enhanced Genome Editing Specificity. Cell. Sep. 12, 2013. vol. 154; pp. 1380-1389. DOI: 10.1016/j.cell.2013.08.021.
International Search Report and Written Opinion issued in corresponding International Application No. PCT/US14/40868, dated Dec. 31, 2014.
Thisse et al. "High-Resolution in situ hybridization to whole-mount zebrafish embryos" 2008. Nature Protocols. vol. 3 No. 1 pp. 59-69. Doi:10.1038/nprot.2007.514.
Grompe (1993) Nature Genetics DOI: 10.1038/ng1093-111.
Office Action issued for corresponding European Patent Application No. 12780609.9, dated Sep. 23, 2015.
Seo, et al. Four-color DNA sequencing by synthesis on a chip using photocleavable fluorescent nucleotides. Proceeding of the National Academy of Sciences, Apr. 2005, 102 (17) 5926-5931.
Brenner, et al. "Gene expression analysis by massively parallel signature sequencing (MPSS) on microbead arrays". Nature Biotechnology vol. 18, pp. 630-634 (2000) doi:10.1038/76469.
Dec. 18, 2014 (PCT) International Preliminary Report—App PCT/US2013/044241.
Shendure Jay et al., "Accurate multiplex polony sequencing of an evolved bacterial genome," Science, American Association for the Advancement of Science, Washington, DC; US, vol. 309, No. 5741, Sep. 1, 2005, pp. 1728-1732, XP002427180, ISSN: 0036-8075, DOI: 10.1126/SCIENCE.1117839.
Extended European Seach Report issued in corresponding European Application No. 12860433.7, dated Aug. 13, 2015.
International Search Report and Written Opinion issued in corresponding International Application No. PCT/US2012/071398, dated Apr. 8, 2013.

Benner et al. "Gene Expression analysis by massively parallel signature sequencing (MPSS) on microbead arrays". Nature Biotechnology, vol. 18, pp. 630-634 (Jun. 31, 2000).
Han et al. "Quantum-dot-tagged microbeads for multiplexed optical coding of biomolecules". Nature Biotechnology, vol. 19, 99. 631-635 (Jul. 31, 2001).
Lee, JH et al. Highly Multiplexed Subcellular RNA Sequencing In Situ. Science. Mar. 21, 2014, vol. 343, No. 6177; pp. 1360-1363; abstract; p. 1360, second column, second paragraph to third column, first paragraph; p. 1361, first column, first paragraph; p. 1363, first column, second paragraph to second column, first paragraph; DOI 10.1126/science.1250212.
Ascano, M et al. Identification of RNA-Protein Interaction Networks Using PAR-CLIP. Wiley Interdiscip Rev RNA. Mar. 2012, vol. 3, No. 2; pp. 159-177; p. 3, third paragraph; p. 16, figure 1; p. 25, figure 6; DOI: 10.1002/wrna.1103.
Ginart, P et al. RNA Sequencing In Situ. Nat Biotechnol. Jun. 2014, vol. 32, No. 6; pp. 543-544; DOI: 10.1038/nbt.2921.
Saliba, AE et al. Single-Cell RNA-Seq: Advances and Future Challenges. Nucleic Acids Res. Jul. 22, 2014, vol. 42, No. 14; pp. 8845-8860; DOI: 10.1093/nar/gku555.
Eliscovich et al. mRNA on the move: The road to its biological destiny. Journal of Biological Chemistry, vol. 288, No. 28, pp. 20361-20368, Jul. 2013, in press May 2013 (Year: 2013).
Weis et al. Protein targeting to subcellular organelles via mRNA localization. Biochimica et Biophysica Acta, vol. 1833, pp. 260-273, 2013, available online Apr. 2012 (Year: 2012).
Jambhekar et al. Cis-acting determinants of asymmetric, cytoplasmic RNA transport. RNA, vol. 13, pp. 625-642, 2007 (Year: 2007).
Singer-Kruger et al. Here, there, everywhere. RNA Biology, vol. 11, No. 8, pp. 1031-1039, Aug. 2014. (Year 2014).
Matlin et al. Spatial expression of the genome: the signal hypothesis at forty. Nature Reviews. Molecular Cell Biology, vol. 12, No. 5, pp. 333-340, May 2011, Epub Apr. 2011 (Year: 2011).
Polidoros et al. Rolling circle amplification—RACE: a method for simultaneous isolation of 5' and 3' cDNA ends from amplified cDNA templates. Bio Techniques, vol. 41, No. 1, pp. 35, 36, 38 and 40, Jul. 2006, including p. 1/1 of Supplementary Material. (Year: 2006).
Tsaftaris et al. Isolation of three homologous AP1-like MADS-box genes in crocus (*Crocus sativus* L.) and characterization of their expression. Plant Science, vol. 166, No. 5, pp. 1235-1243, May 2004 (Year: 2004).
Meeks et al. Characterization of genes encoding poly(A) polymerases in plants: Evidence for duplication and functional specialization. PLoS ONE, vol. 4, No. 11, e8082, Nov. 2009, printed as pp. 1/10-10/10. (Year: 2009).
Kalivas et al. famRCA-RACE: A rolling circle amplification RACE for isolating a family of homologous cDNAs in one reaction . . . Preparative Biochemistry and Biotechnology, vol. 40, No. 3, pp. 177-187, Jul. 2010. (Year: 2010).
Thisse et al. 2008 Nature protocols vol. 3 No. 1 pp. 59-69. Doi:10.1038/nprot.2007.514.
Doilion et al. "Actin Filaments in Normal Dermis and During Wound Healing" The American Journal of Pathology, vol. 126 Issue 1 (1987): pp. 164-170; p. 164 col. 1 para 1, p. 170 col. 1 para 2, fig. 4A-C.
International Search Report and Written Opinion based on PCT/US2018/027583 dated Jun. 29, 2018.
Soderberg, Ola et al.,"Direct observation of individual endogenous protein complexes in situ by proximity ligation," Nature Methods, Dec. 2006, pp. 995-1000, vol. 3, No. 12, Nature Publishing Group.
Schweitzer, Barry et al., "Immunoassays with rolling circle DNA amplification: A versatile platform for ultrasensitive antigen detection" PNAS, Aug. 29, 2000, p. 10113-10119, vol. 97, No. 18.
Cao, Yi et al.,"In-situ immuno-PCR to detect antigens," The Lancet, Sep. 16, 2000, pp. 1002-1003, vol. 356.
Sano, Takeshi et al. "Immuno-PCR: Very Sensitive Antigen Detection by Means of Specific Antibody-DNA Conjugates," Science, Oct. 2, 1992, pp. 120-122, vol. 258.
Dasari, Vivek et al., "Platform for Spatial Molecular Data by Vivek Dasari 1-7 Sig nature redacted Thesis Supervisor", Aug. 20, 2015 (Aug. 20, 2015), XP055559164, Retrieved from the Internet: URL:http://

(56) References Cited

OTHER PUBLICATIONS dspace.mit.edu/bitstream/handle/1721.1/107103/971494098-MIT.pdf?sequence=1 [retreived on Feb. 20, 2019].
Extended European Search Report issued May 13, 2019 for EP Application No. 16862929.3.
Lee, Je Hyuk et al., "Fluorescent in situ sequencing (FISSEQ) or RNA for gene expression profiling in intact cells and tissues", Nature Protocols, vol. 10, No. 3, Feb. 12, 2015 (Feb. 12, 2015), pp. 442-458. XP055272042, GB ISSN: 1754-2189, DOI: 10.1038/nprot.2014.191.
Extended European Search Report dated May 21, 2019 for European Application No. 16862945.9.
Choi, Harry M.T. et al., "Next-Generation in Situ Hybridization Chain Reaction: Higher Gain, Lower Cost, Greater Durability" ACS NANO, vol. 8, No. 5, May 27, 2014 (May 27, 2014), pp. 4284-4294, XP055409053, US.
Ravan, Hadi, et al. "Isothermal RNA detection through the formation of DNA concatemers contiaining HRP-mimicking DNAzymes on the surface of gold nanoparticles", Biosensors and Bioelectronics, Elsevier Science Ltd. UK, Amsterdam, NL, vol. 80, Jan. 18, 2016 (Jan. 18, 2016), pp. 67-73, XP029441324.
Extended European Search Report issued for EP Application No. 17790240.0 dated Sep. 4, 2019.
Brown et al., Review Article : In situ Hybridization with Riboprobes : An Overview for Veterinary Pathologists. Veterinary Pathology 35 : 159-167 (Year: 1998).
Choi et al.,Programmable in situ amplification for multiplexed imaging of mRNA expression. Nature Biotechnology 28 (11): 1208 (Year: 2010).
Choi & Love et al., Immuno-Hybridization Chain Reaction for Enhancing Detection of Individual Cytokine-Secreting Human Peripheral Mononuclear Cells. Analytical Chemistry 83 : 6890-6895 (Year: 2011).
Hansen et al., Sensitive ligand-based protein quantification using immuno-PCR: A critical review of single-probe and proximity ligation assays. Biotechniques 56:217-228 (Year: 2014).
Kuimelis et al., Cleavage properties of an oligonucleotide containing a bridged internucleotide 5-phosphorothioate RNA linkage. Nucleic Acids Research 23 (23) : 4753-4760 (Year: 1999).
Mag et al., Synthesis and selective cleavage of an oligodeoxynucleotide containing a bridged internucleotide 5'-phosphorothioate linkage. Nucleic Acids Research 19(7): 1437 (Year: 1991).
Richardson et al., Experimental and Theoretical Studies of Light-to-Heat Conversion and Collective Heating Effects in Metal Nanoparticle Solutions. Nano Letters 9(3) : 1139-1146 (Year: 2009).
Song et al., Hybridization chain reaction-based aptameric system for the highly selective and sensitive detection of protein. Analyst 137: 1396 (Year: 2012).
Xiao et al., Single-step electronic detection of femtomolar DNA by target-induced strand displacement in an electrode-bound duplex. PNAS 103(45): 16677-16680 (Year: 2006).
Zhang et al., Dynamic DNA nanotechnology using strand-displacement reactions. Nature Chemistry 3 : 103-113 (Year: 2011).
Zhao et al., An electrochemical aptasensor based on hybridization chain reaction with enzyme-signal amplification for interferon-gamma detection. Biosensors and Bioelectronics 36: 129-134 (Year: 2012).
Srinivas et al., On the biophysics and kinetics of toehold-mediated DNA strand displacement. Nucleic Acids Research 41 (22) : 10641-10658 (Year: 2013).
Terry R, Porreca G, McCarthy K, Church GM. 2008. Polonator Instrument http://www.polonator.org; Wayback Machine (Sep. 5, 2008) "Polony Sequence by Ligation Protocol".
Terry R, Porreca G, McCarthy K, Church GM. 2008. Polonator Instrument http://www.polonator.org; Wayback Machine (Jul. 5, 2008) "Polony Sequence Protocols".
Terry R, Porreca G, McCarthy K, Church GM. 2008. Polonator Instrument http://www.polonator.org; Wayback Machine (Sep. 5, 2008) "Help Wanted".
Terry R, Porreca G, McCarthy K, Church GM. 2008. Polonator Instrument http://www.polonator.org; Wayback Machine (Aug. 7, 2008) "Software".
Terry R, Porreca G, McCarthy K, Church GM. 2008. Polonator Instrument http://www.polonator.org; Wayback Machine (Aug. 7, 2008) "Reagent Kits".
Terry R, Porreca G, McCarthy K, Church GM. 2008. Polonator Instrument http://www.polonator.org; Wayback Machine (Sep. 5, 2008) "Run Kits".
Terry R, Porreca G, McCarthy K, Church GM. 2008. Polonator Instrument http://www.polonator.org; Wayback Machine (Sep. 5, 2008) "Paired-Leg Library Kits".
Terry R, Porreca G, McCarthy K, Church GM. 2008. Polonator Instrument http://www.polonator.org; Wayback Machine (Sep. 5, 2008) "Emulsion PCR/Bead Capping Kits".
Terry R, Porreca G, McCarthy K, Church GM. 2008. Polonator Instrument http://www.polonator.org; Wayback Machine (Sep. 5, 2008) "Enrichment Kits".
Terry R, Porreca G, McCarthy K, Church GM. 2008. Polonator Instrument http://www.polonator.org; Wayback Machine (Aug. 7, 2008) "Flow Cells".
Church GM. 2006. "Genomes for all" Sci Am 294: 46-54.
De Bakker PI, Yelensky R, Pe'er I, Gabriel SB, Daly MJ, Altshuler D. 2005. "Efficiency and power in genetic association studies" Nat Genet 37: 1217-23.
Dixon AL, Liang L, Moffatt MF, Chen W, Heath S, Wong KC, Taylor J, Burnett E, Gut I, Farrall M, Lathrop GM, Abecasis GR, Cookson WO. 2007. "A genome-wide association study of global gene expression" Nat Genet 39: 1202-7.
Emilsson V, Thorleifsson G, Zhang B, Leonardson AS, Zink F, Zhu J, Carlson S, Helgason A, Walters GB, Gunnarsdottir S, Mouy M, Steinthorsdottir V, Eiriksdottir GH, Bjornsdottir G, Reynisdottir I, Gudbjartsson D, Helgadottir A, Jonasdottir A, Jonasdottir A, Styrkarsdottir U, Gretarsdottir S, Magnusson KP, Stefansson H, Fossdal R, Kristjansson K, Gislason HG, Stefansson T, Leifsson BG, Thorsteinsdottir U, Lamb JR, Gulcher JR, Reitman ML, Kong A, Schadt EE, Stefansson K. 2008; "Genetics of gene expression and its effect on disease" Nature 452: 423-8.
Risch N, Merikangas K. 1996. "The future of genetic studies of complex human diseases" Science 273: 1516-7.
Schadt EE, Monks SA, Drake TA, Lusis AJ, Che N, Colinayo V, Ruff TG, Milligan SB, Lamb JR, Cavet G, Linsley PS, Mao M, Stoughton RB, Friend SH. 2003. "Genetics of gene expression surveyed in maize, mouse and man" Nature 422: 297-302.
Altshuler D, Daly MJ, Lander ES. 2008. "Genetic mapping in human disease" Science 322: 881-8.
Cookson W, Liang L, Abecasis G, Moffatt M, Lathrop M. 2009. "Mapping complex disease traits with global gene expression" Nat Rev Genet 10: 184-94.
International HapMap C. 2005. "A haplotype map of the human genome" Nature 437: 1299-320. PMC ID: PMC1880871.
Klein RJ. 2007. "Power analysis for genome-wide association studies" BMC Genet 8: 58. PMC ID: PMC2042984.
Kwan T, Benovoy D, Dias C, Gurd S, Provencher C, Beaulieu P, Hudson TJ, Sladek R, Majewski J. 2008. "Genome-wide analysis of transcript isoform variation in humans" Nat Genet 40: 225-31.
McCarroll SA. 2008. "Extending genome-wide association studies to copy-number variation" Hum Mol Genet 17: R135-42.
Eberwine J, Kacharmina JE, Andrews C, Miyashiro K, McIntosh T, Becker K, Barrett T, Hinkle D, Dent G, Marciano P. 2001. "mRna expression analysis of tissue sections and single cells" J Neurosci 21: 8310-4.
Kolb HC, Finn MG, B. SK. 2001. "Click Chemistry: Diverse Chemical Function from a Few Good Reactions" Angew. Chem. Int. 40: 2004-21.
Kwiatkowski M, Fredriksson S, Isaksson A, Nilsson M, Landegren U. 1999. "Inversion of in situ synthesized oligonucleotides: improved reagents for hybridization and primer extension in DNA microarrays" Nucleic Acids Res 27: 4710-4. PMC ID: PMC148770.
Li JB, Gao Y, Aach J, Zhang K, Kryukov GV, Xie B, Ahlford A, Yoon J-K, Rosenbaum AM, Wait-Zaranek A, LeProust E, Sunyaev S, Church GM. 2009. "Multiplex padlock capture and sequencing reveal human hypermutable CpG variations" Genome Res in press.

(56) References Cited

OTHER PUBLICATIONS

Mitra RD, Butty VL, Shendure J, Williams BR, Housman DE, Church GM. 2003. "Digital genotyping and haplotyping with polymerase colonies" Proc Natl Acad Sci U S A 100: 5926-31. PMC ID: PMC156303.

Pan X, Urban AE, Palejev D, Schulz V, Grubert F, Hu Y, Snyder M, Weissman SM. 2008. "A procedure for highly specific, sensitive, and unbiased whole-genome amplification" Proc Natl Acad Sci U S A 105: 15499-504. PMC ID: PMC2563063.

Stougaard M, Lohmann JS, Zajac M, Hamilton-Dutoit S, Koch J. 2007. "In situ detection of non-polyadenylated RNA molecules using Turtle Probes and target primed rolling circle PRINS" BMC Biotechnol 7: 69. PMC ID: PMC2203993.

Wang Z, Gerstein M, Snyder M. 2009. "RNA-Seq: a revolutionary tool for transcriptomics" Nat Rev Genet 10: 57-63.

Wu J, Zhang S, Meng Q, Cao H, Li Z, Li X, Shi S, Kim DH, Bi L, Turro NJ, Ju J. 2007. "3'-O-modified nucleotides as reversible terminators for pyrosequencing" Proc Natl Acad Sci U S A 104: 16462-7. PMC ID: PMC2034218.

Zhang K, Li JB, Gao Y, Egli D, Xie B, Deng J, Li Z, Lee J, Aach J, Leproust E, Eggan K, Church GM. 2009. "Digital RNA Allelotyping Reveals Tissue-specific and Allele-specific Gene Expression in Human" (submitted to Nature Methods).

Bakal C, Aach J, Church G, Perrimon N. 2007. "Quantitative morphological signatures define local signaling networks regulating cell morphology" Science 316: 1753-6.

Li JB, Levanon EY, Yoon J-K, Aach J, Xie B, LeProust E, Zhang K, Gao Y, G.M. C. 2009. "Genome-wide Identification of Human RNA Editing Sites by Parallel DNA Capturing and Sequencing" Science in press.

Meng Q, Kim DH, Bai X, Bi L, Turro NJ, Ju J. 2006. "Design and synthesis of a photocleavable fluorescent nucleotide 3'-O-allyl-dGTP-PC-Bodipy-FL-510 as a reversible terminator for DNA sequencing by synthesis" J Org Chem 71: 3248-52.

Mitra RD, Shendure J, Olejnik J, Edyta Krzymanska O, Church GM. 2003. "Fluorescent in situ sequencing on polymerase colonies" Anal Biochem 320: 55-65.

Porreca GJ, Shendure J, Church GM. 2006. "Polony DNA sequencing" Curr Protoc Mol Biol Chapter 7: Unit 7 8.

Porreca GJ, Zhang K, Li JB, Xie B, Austin D, Vassallo SL, LeProust EM, Peck BJ, Emig CJ, Dahl F, Gao Y, Church GM, Shendure J. 2007. "Multiplex amplification of large sets of human exons" Nat Methods 4: 931-6.

Shendure J, Mitra RD, Varma C, Church GM. 2004. "Advanced sequencing technologies: methods and goals" Nat Rev Genet 5: 335-44.

Shendure JA, Porreca GJ, Church GM. 2008. "Overview of DNA sequencing strategies" Curr Protoc Mol Biol Chapter 7: Unit 7 1.

Tang F, Barbacioru C, Wang Y, Nordman E, Lee C, Xu N, Wang X, Bodeau J, Tuch BB, Siddiqui A, Lao K, Surani MA. 2009. "mRNA-Seq whole-transcriptome analysis of a single cell" Nat Methods 6: 377-82.

Vigneault F, Sismour AM, Church GM. 2008."Efficient microRNA capture and bar-coding via enzymatic oligonucleotide adenylation" Nat Methods 5: 777-9.

Zhang K, Martiny AC, Reppas NB, Barry KW, Malek J, Chisholm SW, Church GM. 2006. "Sequencing genomes from single cells by polymerase cloning" Nat Biotechnol 24: 680-6.

Zhang K, Zhu J, Shendure J, Porreca GJ, Aach JD, Mitra RD, Church GM. 2006. "Long-range polony haplotyping of individual human chromosome molecules" Nat Genet 38: 382-7.

Church et al.; Center for Casual Consequences of Variation (CCV) "An NHGRI Center for Excellence in Genomic Science" http://ccv.med.harvard.edu; Wayback Machine (Jul. 3, 2011).

Church et al.; Center for Casual Consequences of Variation (CCV) "Our four Specific Aims" http://ccv.med.harvard.edu/specific_aims.htm; Wayback Machine (Aug. 13, 2011).

Church; "Proposal for a Center for the determination of the Casual Transcriptional Consequences of Human Genetic Variation (CTCHGV)" http://ccv.med.harvard.edu/CEGS09_Complete_Proposal_minus_Admin_Sections.09May21.final.pdf; Wayback Machine (Aug. 13, 2011).

J. H. Lee, M.D. Ph.D. presentation entitled "Population-wide Tissue-specific Functional Analysis of Human iPS Cells Using Single-Cell In Situ Sequencing" George Church Laboratory, Wyss Institute for Biology Inspired Engineering, Harvard Medical School, Boston, Jan. 10, 2010.

Morley M, Molony CM, Weber TM, Devlin JL, Ewens KG, Spielman RS, Cheung VG. 2004. "Genetic analysis of genome-wide variation in human gene expression" Nature 430: 743-7.

Sachidanandam R, Weissman D, Schmidt SC, Kakol JM, Stein LD, Marth G, Sherry S, Mullikin JC, Mortimore BJ, Willey DL, Hunt SE, Cole CG, Coggill PC, Rice CM, Ning Z, Rogers J, Bentley DR, Kwok PY, Mardis ER, Yeh RT, Schultz B, Cook L, Davenport R, Dante M, Fulton L, Hillier L, Waterston RH, McPherson JD, Gilman B, Schaffner S, Van Etten WJ, Reich D, Higgins J, Daly MJ, Blumenstiel B, Baldwin J, Stange-Thomann N, Zody MC, Linton L, Lander ES, Altshuler D, International SNPMWG. 2001. A map of human genome sequence variation containing 1.42 million single nucleotide polymorphisms. Nature 409 928-933.

Schadt EE, Molony C, Chudin E, Hao K, Yang X, Lum PY, Kasarskis A, Zhang B, Wang S, Suver C, Zhu J, Millstein J, Sieberts S, Lamb J, GuhaThakurta D, Derry J, Storey JD, Avila-Campillo I, Kruger MJ, Johnson JM, Rohl CA, van Nas A, Mehrabian M, Drake TA, Lusis AJ, Smith RC, Guengerich FP, Strom SC, Schuetz E, Rushmore TH, Ulrich R. 2008. "Mapping the genetic architecture of gene expression in human liver" PLoS Biol 6: e107. PMC ID: PMC2365981.

Serre D, Gurd S, Ge B, Sladek R, Sinnett D, Harmsen E, Bibikova M, Chudin E, Barker DL, Dickinson T, Fan JB, Hudson TJ. 2008. "Differential allelic expression in the human genome: a robust approach to identify genetic and epigenetic cis-acting mechanisms regulating gene expression" PLoS Genet 4: e1000006. PMC ID: PMC2265535.

Ball MP, Li JB, Gao Y, Lee J, LeProust E, Park I-H, Xie B, Daley GQ, Church GM. 2009. "Targeted and whole-genome methylomics reveals gene-body signatures in human cell lines" Nat Biotechnol 27: 361-8.

Brenner S, Williams SR, Vermaas EH, Storck T, Moon K, McCollum C, Mao JI, Luo S, Kirchner JJ, Eletr S, DuBridge RB, Burcham T, Albrecht G. 2000. "In vitro cloning of complex mixtures of DNA on microbeads: physical separation of differentially expressed cDNAs" Proc Natl Acad Sci U S A 97: 1665-70. PMC ID: PMC26493.

Chiang DY, Getz G, Jaffe DB, O'Kelly MJ, Zhao X, Carter SL, Russ C, Nusbaum C, Meyerson M, Lander ES. 2009. "High-resolution mapping of copy-number alterations with massively parallel sequencing" Nat Methods 6: 99-103. PMC ID: PMC2630795.

Choy E, Yelensky R, Bonakdar S, Plenge RM, Saxena R, De Jager PL, Shaw SY, Wolfish CS, Slavik JM, Cotsapas C, Rivas M, Dermitzakis ET, Cahir-McFarland E, Kieff E, Hafler D, Daly MJ, Altshuler D. 2008. "Genetic analysis of human traits in vitro: drug response and gene expression in lymphoblastoid cell lines" PLoS Genet 4: e1000287. PMC ID: PMC2583954.

Christian AT, Pattee MS, Attix CM, Reed BE, Sorensen KJ, Tucker JD. 2001. "Detection of DNA point mutations and mRNA expression levels by rolling circle amplification in individual cells" Proc Natl Acad Sci U S A 98: 14238-43. PMC ID: PMC64666.

Church GM, Porreca GJ, Terry RC, Lares M. 2008. "High-Speed Imaging for DNA Sequencing" Biophotonics (<http://www.photonics.com/Content/ReadArticle.aspx?ArticleID=33989>).

Deng J, Shoemaker R, Xie B, Gore A, LeProust EM, Antosiewicz-Bourget J, Egli D, Maherali N, Park IH, Yu J, Daley GQ, Eggan K, Hochedlinger K, Thomson J, Wang W, Gao Y, Zhang K. 2009. "Targeted bisulfite sequencing reveals changes in DNA methylation associated with nuclear reprogramming" Nat Biotechnol 27: 353-60.

Bang D, Church GM. 2008. "Gene synthesis by circular assembly amplification" Nat Methods 5: 37-9.

Bell J. 2004. "Predicting disease using genomics" Nature 429: 453-6.

Eid J, Fehr A, Gray J, Luong K, Lyle J, Otto G, Peluso P, Rank D, Baybayan P, Bettman B, Bibillo A, Bjornson K, Chaudhuri B,

(56) References Cited

OTHER PUBLICATIONS

Christians F, Cicero R, Clark S, Dalal R, Dewinter A, Dixon J, Foquet M, Gaertner A, Hardenbol P, Heiner C, Hester K, Holden D, Kearns G, Kong X, Kuse R, Lacroix Y, Lin S, Lundquist P, Ma C, Marks P, Maxham M, Murphy D, Park I, Pham T, Phillips M, Roy J, Sebra R, Shen G, Sorenson J, Tomaney A, Travers K, Trulson M, Vieceli J, Wegener J, Wu D, Yang A, Zaccarin D, Zhao P, Zhong F, Koriach J, Turner S. 2009. Real-time DNA sequencing from single polymerase molecules. Science 323:133-138.

Harris TD, Buzby PR, Babcock H, Beer E, Bowers J, Braslavsky I, Causey M, Colonell J, Dimeo J, Efcavitch JW, Giladi E, Gill J, Healy J, Jarosz M, Lapen D, Moulton K, Quake SR, Steinmann K, Thayer E, Tyurina A, Ward R, Weiss H, Xie Z. 2008. "Single-molecule DNA sequencing of a viral genome" Science 320:106-9.

Kim JB, Porreca GJ, Song L, Greenway SC, Gorham JM, Church GM, Seidman CE, Seidman JG. 2007. "Polony multiplex analysis of gene expression (PMAGE) in mouse hypertrophic cardiomyopathy" Science 316: 1481-4.

Kurimoto K, Yabuta Y, Ohinata Y, Saitou M. 2007. "Global single-cell cDNA amplification to provide a template for representative high-density oligonucleotide microarray analysis" Nat Protoc 2: 739-52.

Wang et al. "Rapid and Sensitive Detection of Severe Acute Respiratory Syndrome Coronavirus by Rolling Circle Amplification" Journal of Clinical Microbiology, vol. 43, No. 5, May 2005, pp. 2339-2344.

Goransson et al. "A single molecule array for digital targeted molecular analyses" Nucleic Acids Research, 2009, vol. 37, No. 1, e7, doi:10.1093/nar/gkn921.

Dirks et al. "Triggered amplificaiton by hybridization chain reaction" PNAS; Oct. 26, 2004; vol. 101, No. 43, pp. 15275-15278.

Lubeck et al. "Single cell systems biology by super-resolution imaging and combinatorial labeling" Nature Methods; 9 (7); pp. 743-748; 2012.

Ho et al. "Sequencing by ligation variation with endonuclease V digestion and deoxyinosine-containing query oligonucleotides" BMC Genomics, 2011, 12:598.

Jiang et al. "Solar thermal polymerase chain reaction for smartphone-assisted molecular diagnostics" Scientific Reports, 4:4137, 2014.

Ju et al. "Four-color DNA sequencing by synthesis using cleavable fluorescent nucleotide reversible terminators" PNAS, Dec. 26, 2006, vol. 103, No. 52, p. 19635-19640.

Lubeck et al. "Single cell in situ RNA profiling by sequential hybridization" Nature Methods, Apr. 2014, 11(4), pp. 360-361.

Parinov et al. "DNA sequencing by hybridization to microchip octa- and decanucleotides extended by stacked pentanucleotides" Nucleic Acids Research, 1996, vol. 24, No. 15, pp. 2998-3004.

Schouten et al. "Relative quantification of 40 nucleic acid sequences by multiplex ligation-dependent probe amplification" Nucleic Acids Research, 2002, vol. 30, No. 12, e57.

COMPOSITIONS AND METHODS FOR ANALYTE DETECTION

RELATED APPLICATION DATA

This application is a continuation application which claims priority to U.S. patent application Ser. No. 16/941,585, filed on Jul. 29, 2020, which is a continuation-in-part application which claims priority to U.S. patent application Ser. No. 16/157,243, filed on Oct. 11, 2018, which is a continuation application that claims priority to U.S. patent application Ser. No. 14/774,282, filed on Sep. 10, 2015, which is a National Stage Application under 35 U.S.C. 371 of PCT Application No. PCT/US2014/018580 designating the United States and filed Feb. 26, 2014; which claims the benefit of U.S. Provisional Application No. 61/777,383 and filed Mar. 12, 2013 each of which are hereby incorporated by reference in their entireties.

U.S. patent application Ser. No. 16/941,585, filed on Jul. 29, 2020 is also a continuation-in-part application which also claims priority to U.S. patent application Ser. No. 16/393,215, filed on Apr. 24, 2019, which is a continuation application which claims priority to U.S. patent application Ser. No. 16/255,920, filed on Jan. 24, 2019, which is a continuation application which claims priority to U.S. patent application Ser. No. 14/366,486, filed on Jun. 18, 2014, which is a National Stage Application under 35 U.S.C. 371 of PCT Application No. PCT/US2012/071398 designating the United States and filed Dec. 21, 2012; which claims the benefit of U.S. Provisional Application No. 61/579,265 and filed Dec. 22, 2011.

STATEMENT OF GOVERNMENT INTERESTS

This invention was made with Government support under grant number 1P50HG005550 awarded by NHGRI. The Government has certain rights in the invention.

FIELD OF THE INVENTION

The present invention relates to methods of making a three-dimensional matrix of nucleic acids and amplifying, detecting and sequencing such nucleic acids within the matrix.

BACKGROUND OF THE INVENTION

Since many gene products such as RNA and proteins are enriched in regions where they function, their location provides an important clue to their function. This property has been used for in situ fluorescent hybridization, immunohistochemistry and tissue-specific reporter assays in numerous areas of biological research.

Current methods involve extracting nucleic acid molecules from their native environment or making synthetic nucleic acid molecules, amplifying them in solution and placing them on a flat array surface or beads for gene detecting via hybridization or sequencing, making it impossible to identify the cellular origin of individual nucleic acids.

SUMMARY

Embodiments of the present invention are directed to methods of making a three dimensional matrix of nucleic acids. Embodiments of the present invention are directed to methods of making a three dimensional matrix including nucleic acids covalently bound into a matrix or into or to a matrix material. The nucleic acids may be co-polymerized with the matrix material or cross-linked to the matrix material or both. According to one aspect, a plurality of nucleic acid sequences of certain length, such as DNA or RNA sequences are part of a three-dimensional copolymer. The nucleic acids may then be amplified and sequenced in situ, i.e. within the matrix. The three-dimensional matrix of nucleic acids provides, in a certain aspect, an information storage medium where the nucleic acids, i.e. a sequence of one or more nucleotides, represent stored information which can be read within the three-dimensional matrix. According to one aspect, nucleic acids such as DNA or RNA sequences of given length are covalently attached to a matrix material to preserve their spatial orientation in the x, y and z axes within the matrix. It is to be understood that the three dimensional matrix may include a matrix material and that the term copolymer, matrix and matrix material may be used interchangeably.

According to one aspect, methods described herein are directed to immobilizing naturally occurring nucleic acids within their native environment, such as within a cell or within a tissue sample. The three dimensional nucleic acid matrix can be generated in situ in a cell or tissue sample to preserve the naturally occurring nucleic acid sequence diversity (such as DNA and RNA) and spatial orientation in cells, tissues or any other complex biomaterial. According to this aspect, the location of nucleic acids and their relative position is identified as a three dimensional structure, such as within subcellular compartments, within cells, within tissues, as three dimensional nucleic acid assemblies, as three dimensional nucleic acid material, etc. The nucleic acids can be amplified and sequenced, if desired, in situ thereby providing positional information of the nucleic acids within the cell or tissue.

According to a related aspect, nucleic acids of interest, whether naturally occurring or synthetic, can be present within a three dimensional matrix material and covalently attached to the three dimensional matrix material such that the relative position of each nucleic acid is fixed, i.e. immobilized, within the three dimensional matrix material. In this manner, a three-dimensional matrix of covalently bound nucleic acids of any desired sequence is provided. Each nucleic acid has its own three dimensional coordinates within the matrix material and each nucleic acid represents information. In this manner, a large amount of information can be stored in a three dimensional matrix. Individual information-encoding nucleic acids, such as DNA or RNA can be amplified and sequenced in situ, i.e., within the matrix, thereby enabling a large amount of information to be stored and read in a suitable three dimensional material.

According to a further aspect, the nucleic acids can be amplified to produce amplicons within the three dimensional matrix material. The amplicons can then be covalently attached to the matrix, for example, by copolymerization or cross-linking. This results in a structurally stable and chemically stable three dimensional matrix of nucleic acids. According to this aspect, the three dimensional matrix of nucleic acids allows for prolonged information storage and read-out cycles. The nucleic acid/amplicon matrix allows for high throughput sequencing of a wide ranging array of biological and non-biological samples in three dimensions.

According to certain aspects, a three dimensional nucleic acid matrix is provided where a plurality of nucleic acid molecules, such as DNA or RNA, amplicons or nucleic acid structural units are immobilized, such as by covalent bonding to the matrix, in a three dimensional space relative to one another. In this context, the nucleic acid molecules are rigidly fixed to the extent that they maintain their coordinate position within the matrix. It is to be understood that even though a nucleic acid molecule may be covalently attached to the three dimensional matrix material, the nucleic acid molecule itself may be capable of movement though bound to the matrix, such as for example, when a nucleic acid sequence is bound to the matrix at a single location on the nucleic acid.

According to one aspect, the three dimensional matrix including nucleic acids is porous. According to one aspect, the three dimensional matrix including nucleic acids is porous to the extent that reagents typically used in amplification methods can diffuse or otherwise move through the matrix to contact nucleic acids and thereby amplify nucleic acids under suitable conditions.

According to one aspect, the three dimensional matrix material is chemically inert and thermally stable to allow for various reaction conditions and reaction temperatures. According to this aspect, the three dimensional matrix material is chemically inert and thermally stable to conditions used in amplification and sequencing methods known to those of skill in the art.

According to one aspect, the three dimensional matrix material is optically transparent. According to one aspect, the three dimensional matrix material is optically transparent to allow for three dimensional imaging techniques known to those of skill in the art.

According to one aspect, the nucleic acids are amplified to an extent to produce sufficient levels of amplicons for three dimensional imaging. For example, the nucleic acids are amplified and include a label sufficient for a high level of fluorescence compatible with three dimensional imaging.

According to one aspect, the material used to form the matrix is compatible with a wide range of biological and non-biological specimens in situ so as to avoid extracting the nucleic acid molecules away from their native environment.

According to one aspect, the matrix material may be a semi-solid medium that can be made from polyacrylamide, cellulose, alginate, polyamide, cross-linked agarose, cross-linked dextran or cross-linked polyethylene glycol. In certain aspects, the semi-solid medium has x, y and z axes, and the nucleic acids are present randomly or non-randomly within the three dimensional matrix.

According to one aspect, the matrix material is porous. Porosity can result from polymerization and/or crosslinking of molecules used to make the matrix material. The diffusion property within the gel matrix is largely a function of the pore size. The molecular sieve size is chosen to allow for rapid diffusion of enzymes, oligonucleotides, formamide and other buffers used for amplification and sequencing (>50-nm). The molecular sieve size is also chosen so that large DNA or RNA amplicons do not readily diffuse within the matrix (<500-nm). The porosity is controlled by changing the cross-linking density, the chain lengths and the percentage of co-polymerized branching monomers according to methods known to those of skill in the art.

In certain aspects, the semi-solid medium can be attached to a solid support such as a microscope slide or a flow cell. The solid support can be attached to the bottom surface of the semi-solid medium.

Embodiments provided herein are based on, at least in part, the development of a multiplexed biological assay and readout, in which a multitude of detection reagents comprising one or more probes and/or probe types are applied to a sample, allowing the detection reagents to bind target molecules or analytes, which can then be optically identified in a temporally-sequential manner. In some embodiments, the multitude of detection reagents comprising one or more probes and/or probe types can be applied to a sample simultaneously. Accordingly, provided herein are methods, compositions (e.g., detection reagents) and kits for detecting multiple analytes in a sample.

Accordingly, one aspect provided herein relates to a method for detecting a plurality of analytes in a sample. Exemplary analytes include, without limitations, antigens, receptors, proteins, peptides, nucleic acids, sugars, lipid, carbohydrates, glycans, glycoproteins, oligonucleotides, cells, viruses, and any combinations thereof. In some embodiments, the nucleic acids can include, e.g., cellular DNA or RNA, messenger RNA, microRNA, ribosomal RNA, and any combinations thereof. A sample amenable to the methods described herein can be a sample from any sources, e.g., but not limited to biological samples, e.g., collected from organisms, animals or subjects, environmental samples, food, food byproduct, soil, archaeological samples, extraterrestrial samples, or any combinations thereof. For example, a sample can be a protein sample immobilized on a solid support including, e.g., a blotting membrane. In alternative embodiments, a sample can comprise one or more cells, one or more tissues, one or more fluids, or any combinations thereof. In some embodiments, the sample can comprise a tissue sample. In some embodiments, the sample can comprise a fluid sample. In some embodiments, a sample can comprise blood, sputum, cerebrospinal fluid, urine, saliva, sperm, sweat, mucus, nasal discharge, vaginal fluids or any combinations thereof. In some embodiments, a sample can comprise a biopsy, a surgically removed tissue, a swap, or any combinations thereof.

The method described herein comprises: (a) contacting the sample with a plurality of detection reagents as described herein, wherein each subpopulation of the detection reagents can target at least one different analyte; and (b) detecting in a temporally-sequential manner said plurality of the pre-determined subsequences of said detection reagents, wherein said detection of the subsequences each generates a signal signature corresponding to said subsequence, and wherein a temporal order of the signal signatures corresponding to said plurality of the subsequences of said detection reagent identifies a subpopulation of the detection reagents. In some embodiments, the temporal order of the signal signatures corresponding to said plurality of the subsequences of said detection reagent can be unique for each subpopulation of the detection reagents.

In some embodiments, a detection reagent described herein can target at least two distinct analytes. In some embodiments, a first subpopulation of the detection reagents can target at least one analyte different from that of a second subpopulation of the detection reagents. Accordingly, in some embodiments, the readout of the detection reagents can be distinct but overlapping.

In some embodiments, the method can further comprise processing the sample before contacting with the plurality of detection reagents described herein.

In some embodiments, the method can further comprise removing any unbound detection reagents before detection of the pre-determined subsequences in a temporally-sequential manner.

In some embodiments, the method can further comprise comparing the temporal order of the signal signatures with different identifiers of said at least one probe reagent, wherein an agreement between the temporal order of the signal signatures and a particular identifier of said at least one probe reagent identifies the analyte in the sample. In some embodiments, the method can further comprise measuring the intensity of the signal signatures generated from each subpopulation of the detection reagents. In some embodiments, the intensity of the signal signatures generated from each subpopulation of the detection reagents can indicate an amount of the analyte. In some embodiments, the relative intensity of the signal signatures can be used in identification of each subpopulation of the detection reagents. Thus, the intensity of the signal signatures can be used as part of a coding scheme of the detection reagents described herein. The comparing and intensity measuring steps can be performed by a computer-implemented software or algorithm.

Each signal signature corresponding to individual predetermined subsequences of the detection reagent are detected in a temporally-sequential manner. In some embodiments, the detection method can include sequencing, e.g., which can be performed via any methods known in the art, including but not limited to, ligation, hybridization, synthesis, amplification, single-base extension, or any methods known in the art. In certain embodiments, the detection method can include hybridizing a decoder probe with the corresponding subsequence, wherein the decoder probe can comprise a detectable label.

In particular embodiments, the detection method can comprise: (a) hybridizing a set of decoder probes with a subsequence of the detection reagents, wherein each subpopulation of the decoder probes can comprise a detectable label, each detectable label producing a signal signature; (b) detecting said different signal signature produced by the hybridization of said set of decoder probes; (c) optionally removing said different signal signature produced by the hybridization of said set of decoder probes; and (d) repeating steps (a) through (c) for other subsequences of said detection reagents, thereby producing a temporal order of the signal signatures corresponding to said each detection reagent. In some embodiments, removal of the different signal signature produced by the hybridization can be performed by washing, heating, photo-bleaching, displacement (e.g., displacement of decoder probes with another reagent or nucleic acid sequence), cleavage, enzymatic digestion, quenching, chemical degradation, bleaching, oxidation, or any combinations thereof.

In some embodiments, each decoder probe in the set can independently have a subsequence of the detection reagents.

In some embodiments, each subpopulation of the decoder probes can comprise a different detectable label, each different detectable label producing a different signal signature.

In some embodiments, each subpopulation of the decoder probes can be complementary (e.g., partially complementary or completely complementary) to the subsequence of the detection reagents. In some embodiments, a first subpopulation and a second subpopulation of the decoder probes can be complementary (e.g., partially complementary or completely complementary) to the same subsequence of the detection reagents. In some embodiments, a first subpopulation and a second subpopulation of the decoder probes can be complementary (e.g., partially complementary or completely complementary) to distinct subsequences of the detection reagents.

In some embodiments involving decoder probes for detection purposes, the detectable label associated with each subpopulation of the decoder probes can comprise an optical label selected from the group consisting of a small-molecule dye, a fluorescent molecule or protein, a quantum dot, a colorimetric reagent, a chromogenic molecule or protein, a Raman label, a chromophore, and any combinations thereof. In some embodiments, the detectable label or optical label can be a fluorescent molecule or protein.

Types of signal signature(s) can vary upon different embodiments of detection reagents and/or decoder probes described herein. By way of example, the detection reagents and/or decoder probes can comprise an optical molecule or label, thus producing optical signatures. Examples of optical signatures can include, without limitations, signatures of fluorescent color (e.g., emission spectra under one or more excitation spectra), visible light, no-color or no-light, color (e.g., color defined by a visible light wavelength), Raman signatures, and any combinations thereof. In some embodiments, an optical signature can comprise signatures of one or more fluorescent colors, one or more visible lights, one or more no-colors or no-lights, one or more colors, one or more Raman signatures, or any combinations thereof. For example, in one embodiment, an optical signature can comprise a plurality (e.g., at least 2 or more) of fluorescent colors (e.g., fluorescent dyes). In these embodiments, the optical signatures can be detected by optical imaging or spectroscopy.

The spatial movement limit of an analyte in a sample allowed for a temporal detection of the detection reagents to occur can vary depending on a number of factors, including, but not limited to, presence of any distinguishable features within a field of detection, magnification used in detection (e.g., magnification of the microscope lens), density of the analytes in a sample, and any combinations thereof. In some embodiments, there can be no limit in the spatial movement of an analyte in a sample during a temporal detection of the detection reagents, for example, provided that the analyte stay within the field of detection and there is at least one same distinguishable feature in each image taken during a temporal detection so that the images can be aligned to each other based on the same distinguishable feature. In some embodiments where there is no such distinguishable feature, the spatial movement of an analyte in a sample can be less than 100 μm, including less than 50 μm, less than 25 μm, less than 10 μm, less than 1 μm or smaller, over a time period, during which a temporal detection of the detection reagents occurs. In some embodiments, the spatial movement of an analyte in a sample can be less than 1000 nm, including less than 500 nm, less than 250 nm, less than 100 nm, less than 50 nm, less than 10 nm or smaller, over a time period, during which a temporal detection of the detection reagents occurs. More importantly, the spatial movement limit of an analyte in a sample during a temporal detection is determined by the ability of matching distinguishable features between images taken during a temporal detection, which can be affected by imaging conditions. In some embodiments, the analyte can be fixed on a solid substrate or support.

In one aspect, embodiments provided herein relate to a detection reagent, which can be used in a multiplexing assay. The detection reagent comprises at least one probe reagent and at least one nucleic acid label, wherein said at least one nucleic acid label comprises at least one pre-determined subsequence to be detected in a temporally-sequential manner; wherein said at least one pre-determined subsequence forms an identifier of said at least one probe reagent; and wherein said at least one probe reagent and said at least one nucleic acid label are conjugated together.

In some embodiments, the probe reagent and the nucleic acid label can be conjugated together by at least one linker. The linker can be monovalent or multivalent. Exemplary linkers include, but are not limited to, a bond, a linker molecule, and/or a particle, for example, selected from a group consisting of a gold nanoparticle, a magnetic bead or nanoparticle, a polystyrene bead, a nanotube, a nanowire, a microparticle, and any combinations thereof. In some embodiments, the linker can be a nanoparticle. Examples of linker molecules can include, but are not limited to, a polymer, sugar, nucleic acid, peptide, protein, hydrocarbon, lipid, polyethelyne glycol, crosslinker, or combination thereof.

When the linker is a particle, in some embodiments, the particle can be modified by any methods known in the art. For example, the particle can be coated with streptavidin or a derivative thereof. In some embodiments, the particles can be modified or functionalized with at least one functional group. Examples of the functional groups can include, but are not limited to, amine, carboxyl, hydroxyl, aldehyde, ketone, tosyl, silanol, chlorine, hydrazine, hydrazide, photoreactive groups and any combination thereof.

The probe reagent of the detection reagent can be any targeting molecule of interest. Examples of the probe reagent can include, but are not limited to, a nucleic acid, an antibody or a portion thereof, an antibody-like molecule, an enzyme, a cell, a virus, an antigen, a small molecule, a protein, a peptide, a peptidomimetic, a sugar, a lipid, a glycoprotein, a peptidoglycan, an aptamer, and any combinations thereof. In some embodiments, the probe reagent can be modified by any means known to one of ordinary skill in the art. By way of example, the probe reagent can be genetically modified, or it can be biotinylated.

The nucleic acid label of the detection reagent can have any configuration and/or any sequence length. In some embodiments, the nucleic acid label can be single-stranded, double-stranded, partially double-stranded, a hairpin, linear, circular, branched, a concatemer (e.g., a concatemer with a 3D structure such as a colony, i.e., rolling-circle colony, or a DNA nanoball), or any combinations thereof. In various embodiments, the nucleic acid label can be designed for minimal cross-hybridization of bases with each other.

In some embodiments, the nucleic acid label can be a modified nucleic acid label. An exemplary modification of the nucleic acid label includes, without limitations, conjugation of the nucleic acid label to one or more detectable molecules. The detectable molecule can include any optical molecule, including, but not limited to, a small-molecule dye, a fluorescent protein, a quantum dot, or any combinations thereof.

In some embodiments, the nucleic acid label can comprise at least a partially double-stranded region. For example, the nucleic acid label can be pre-hybridized with at least one optically-labeled decoder probe, e.g., to produce at least the first signal of the temporal image stack. In such embodiments, additional decoder probes can be added during the detection method described herein to hybridize with other single-strand subsequences of the nucleic acid label.

In some embodiments, the nucleic acid label can comprise a plurality of pre-determined subsequences. Each of the pre-determined subsequences can be independently of any length. In some embodiments, at least one of the pre-determined subsequences can comprise one or more nucleobases. In certain embodiments, at least one of the pre-determined subsequences can comprise from 1 to 100 nucleobases.

The pre-determined subsequences with the nucleic acid label can be conjugated together by at least one sequence linker. In some embodiments, the sequence linker can be a direct bond, e.g., a phosphoester bond, which can allow conjugation of the pre-determined subsequences to form a longer, contiguous sequence. In some embodiments, the sequence linker can be a nucleotidic linker. When the pre-determined subsequences are conjugated together by a nucleotidic linker, the nucleotidic linker can have a sequence length of at least one nucleotide. The nucleotidic linker, in some embodiments, can be single-stranded, double-stranded, partially double-stranded, a hairpin, or any combinations thereof.

Depending on various applications and/or assay conditions (e.g., sensitivity, sample volume/concentration), a detection signal of a probe can be amplified by conjugating the probe to a plurality of the nucleic acid labels. In such embodiments, the detection reagent can comprise one probe reagent and a plurality of nucleic acid labels. Without wishing to be limiting, in other embodiments, the detection reagent can comprise a plurality of probe reagents and a nucleic acid label. In some embodiments, the detection reagent can comprise a plurality of probe reagents and a plurality of nucleic acid labels.

The detection reagents and methods described herein can be used in any biological assays for detection, identification and/or quantification of target molecules or analytes in a sample. In particular embodiments, the detection reagent can be present in a soluble phase for various biological assays. By way of example only, in some embodiments, the detection reagent can be adapted for use in immunofluorescence. For example, the detection reagent adapted for use in immunofluorescence can be used to identify microbes or pathogens. In alternative embodiments, the detection reagent can be adapted for use in immunohistochemistry. For example, the detection reagent adapted for use in immunohistochemistry can be used to study tissue biopsies or cultured cells. In some embodiments, the detection reagent and the method described herein can be applied to fixed cells and/or living cells. In other embodiments, the detection reagent can be adapted for use in fluorescence in situ hybridization. In some embodiments, the detection reagent can be adapted for use in western blot. Accordingly, the detection reagent described herein can be adapted for use in various applications, e.g., but not limited to, pathogen detection and/or identification, cancer-tissue analysis and other medical pathology applications, lineage tracking of differentiating stem cells, and lineage tracking and/or identification of dendritic cells.

Kits for various biological assays also provided herein. In some embodiments, a kit can comprise: (a) a plurality of the detection reagents described herein or a portion thereof; and (b) at least one reagent. Examples of a reagent include, but are not limited to, a readout reagent, a wash buffer, a signal removal buffer, and any combinations thereof.

The kits provided herein can be used for sequencing-based readout or hybridization-based readout. In some embodiments where the kit is used for hybridization-based readout, the kit can further comprise at least one set of decoder probes complementary to at least a portion of subsequences of the detection reagents, wherein each sub-population of the decoder probes comprises a different detectable label, each different detectable label producing a different signal signature.

In some embodiments, the kit can comprise a plurality of at least one component of the detection reagents, e.g., the "nucleic acid label" component of the detection reagents. In such embodiments, users can attach the provided nucleic acid labels to their probe reagents of interest to form their own detection reagents described herein. In such embodiments, the kit can further comprising at least one coupling agent that allows the user to conjugate at least one nucleic acid label to the user's probe reagents of interest. In other embodiments, the nucleic acid labels can be already attached to the pre-determined probe reagents and are thus provided to users in the form of the detection reagents that are ready to use.

In some embodiments, the detection reagents provided in the kit or formed by a user can be provided in a solution phase. In other embodiments, the detection reagents provided in the kit or formed by a user can be immobilized in a multi-well plate.

In some embodiments of any aspects described herein, the analytes or target molecules can be present in a solution phase. In some embodiments, the analytes or target molecules can be immobilized on a solid substrate or support.

To clarify, the compositions and methods described herein are different from the ones described in the US Patent Application No.: US 2007/0231824. The '824 application discusses methods of decoding a sensor array containing immobilized microspheres, wherein the microspheres are immobilized on a solid support (e.g., an array substrate), rather than designed to be in a solution phase. As such, a sample fluid is flowed over the sensor array containing immobilized microspheres. The analytes in the sample fluid then bind to the immobilized microspheres. After binding, the sample fluid is then discarded and the immobilized microspheres are analyzed. Accordingly, the compositions and the methods described in the '824 application cannot be used and detected directly on a sample (e.g., on a tissue sample) or in situ as described herein, e.g., immunofluorescence, immunohistochemistry, fluorescence in situ hybridization, or western blot.

Further, the assay methods described herein are also different from the general nanostring technology or other technologies as described in the U.S. Pat. No. 7,473,767, and the U.S. Patent Application No.: US 2010/0047924. The general nanostring technology and nanoreporter detection methods described in the '924 application are based on determination of the "spatial location of signals" emanating from the labeled nanostrings or nanoreporters. The detection methods described in the '767 patent is based on the color resulting from various ratios of different optical labels bound to the polynucleotide probes. All these previous methods will require at least a plurality of optical labels to be detected simultaneously for determination of spatial location of signals or the resultant color from various ratios of different optical labels. Accordingly, all these previous methods do not involve detection of signals in a temporally-sequential manner as described herein. Further, there are at least two disadvantages of nanostring technology based on detection of "spatial location of signals," rather than temporal detection of signals as described herein. First, compared to the methods and detection reagents described herein, the nanostring technology generally requires very high optical magnification for spatially discerning separation of colors that are typically located very close to each other within a nanostring; thus limiting a field of view/sample size, and precision, and/or increasing instrument cost. Second, unlike the methods and detection reagents described herein, the nanostring technology generally requires a thorough control of the amount of probes used in detection, because too few probes would yield a signal that is difficult to be detected, but too many probes would increase the likelihood of probes overlapping, and thus making the readout impossible.

BRIEF DESCRIPTION OF THE DRAWINGS

FIG. 8B: Readout stage 2).

Step 1: Set 1 Probes only;
Step 2: Set 1 Displacement oligonucleotides and Set 2 Probes;
Step 3: Set 2 Displacement oligonucleotides and Set 3 Probes; and
Step 4: Set 3 Displacement oligonucleotides.

SeqTag Label and corresponding colors were as follow:
Set 1: SeqTag 1—Green, SeqTag 2—Red, and SeqTag 3—Blue;
Set 2: SeqTag 4—Green, SeqTag 5—Red, and SeqTag 6—Blue;
Set 3: SeqTag 7—Green and SeqTag 8—Red.

Figure 10:
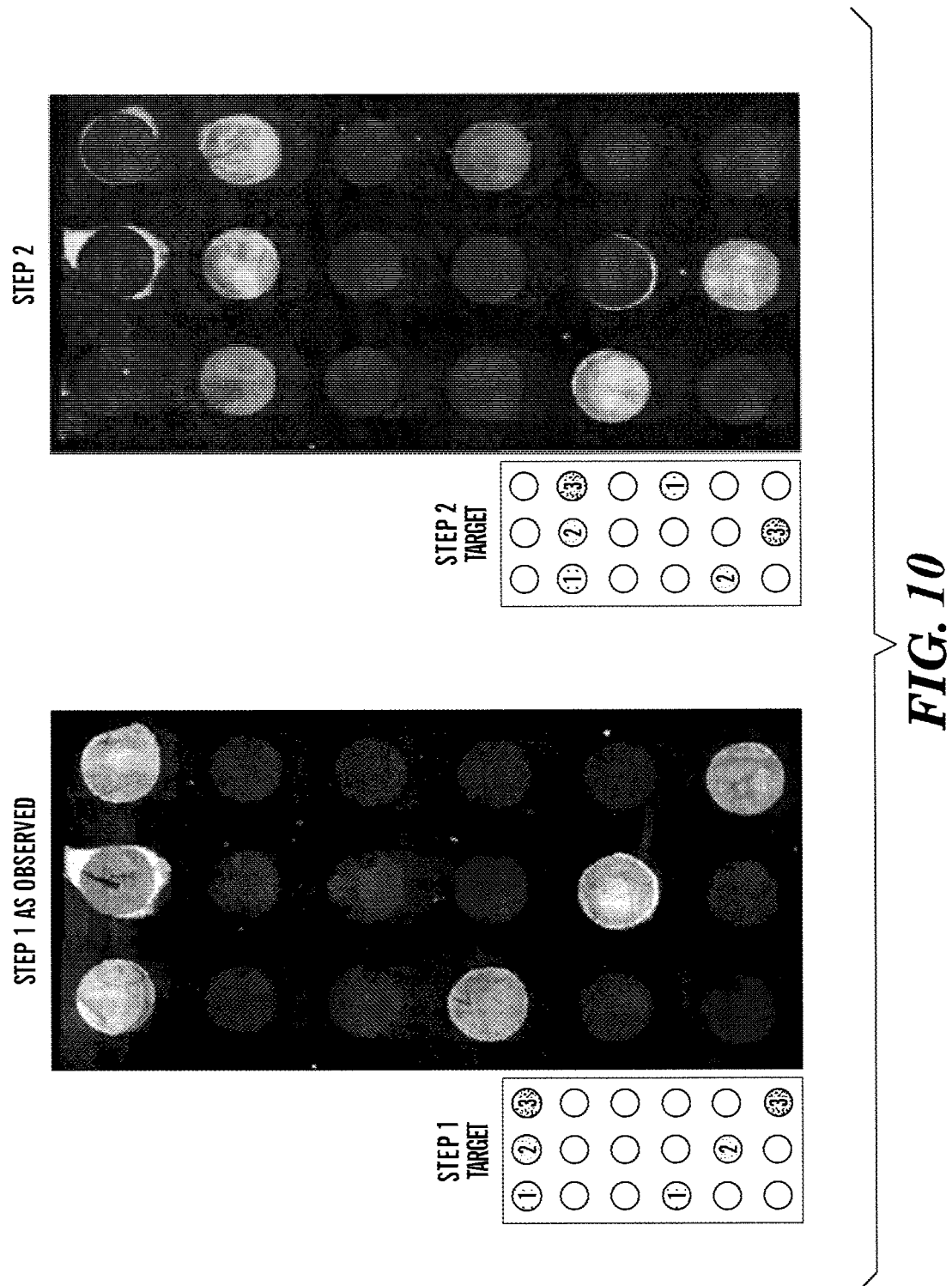

FIG. 10 shows SeqTag readout by a displacement-hybridization experiment according to an embodiment of the method described herein. SeqTag DNA labels were incubated on a streptavidin-coated microarray. This microarray was then exposed to a sequence of fluorescently labeled detection probes and displacement oligonucleotidess, as per displacement-hybridization readout. Imaging the array after each readout step demonstrated fluorescence corresponding to the expected pattern (shown next to each image).

Figure 11:
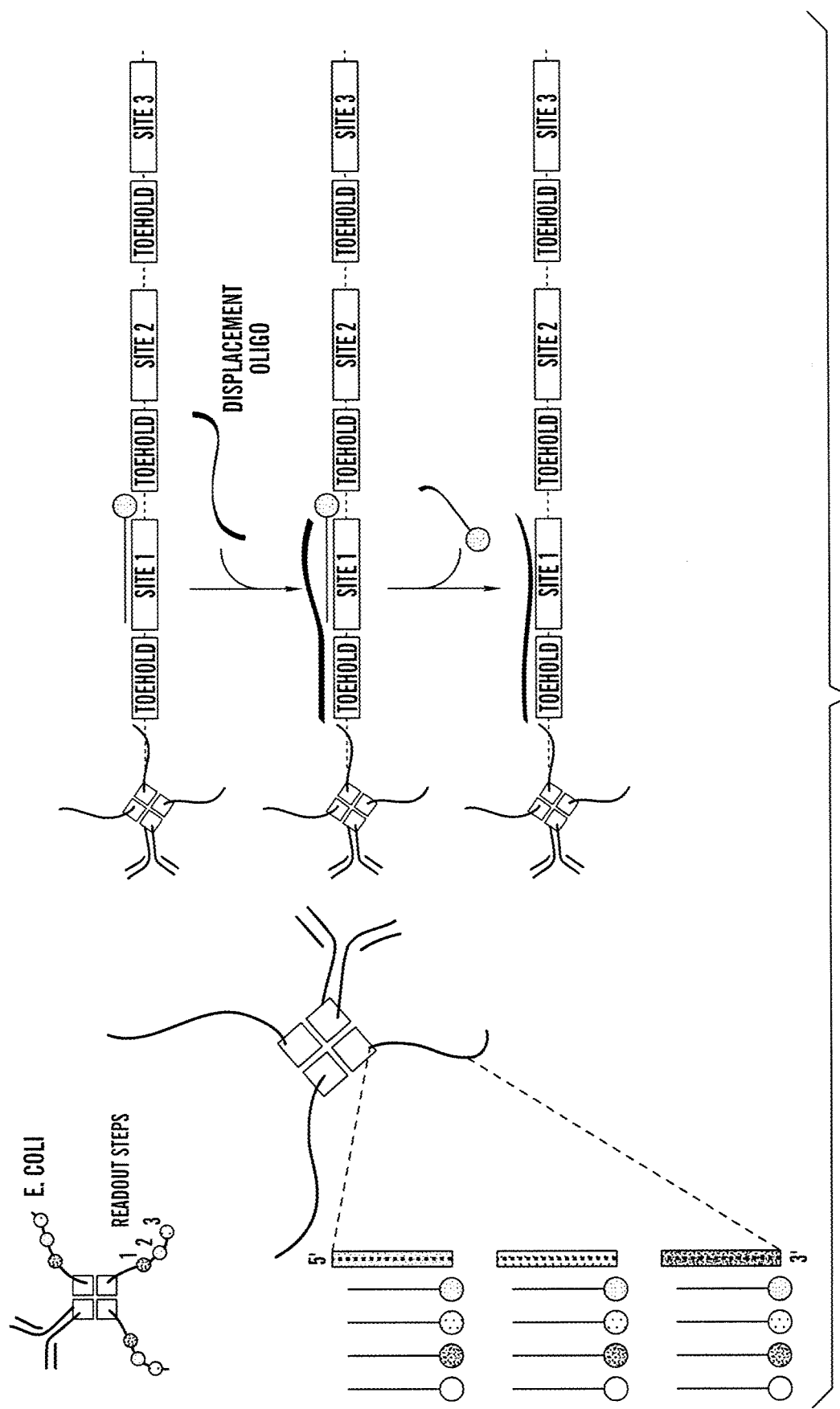

FIG. 11 is a schematic representation of displacement hybridization according to an embodiment of the method. As the readout progresses, fluorescence from prior readout steps needs to be removed so as not to obstruct the current step's signal. As illustrated in FIG. 11, this can be accomplished using a displacement-hybridization method: each of the SeqTag's hybridization sites can be preceded by a short "toehold" sequence. During each readout step, the sample is subjected to a mixture of "displacer" DNA oligonucleotides. One of these displacers is complementary to the preceding step's hybridization site and, with the help of the toehold, is capable of displacing the fluorescent probe that was bound there.

Figure 12:
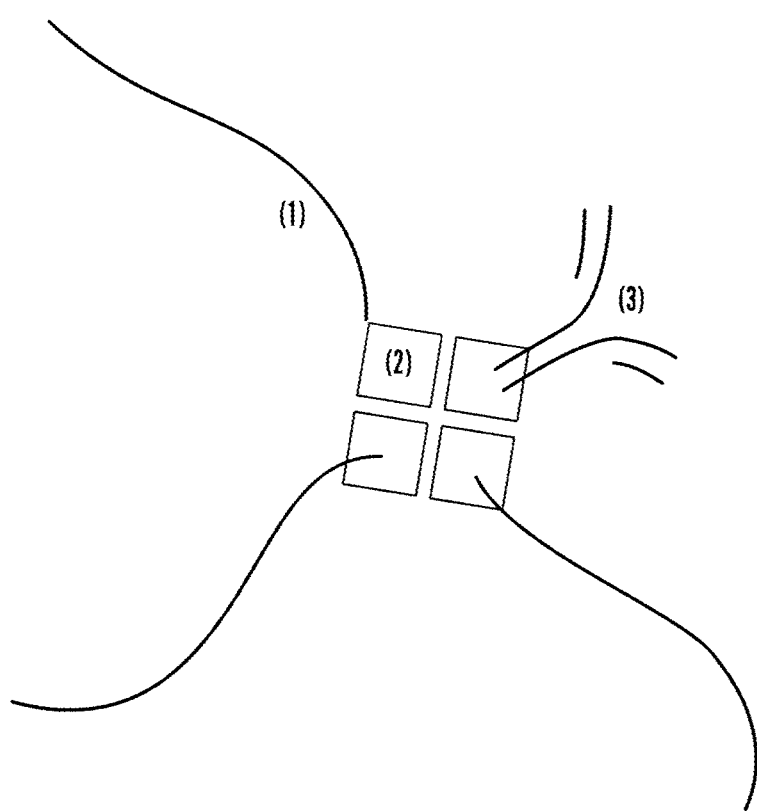

FIG. 12 is a schematic representation of a probe reagent according to an embodiment described herein. Shown is an oligonucleotide-antibody-streptavidin construct. A convenient and effective way to SeqTag-label antibodies is through a streptavidin bridge. The antibody is biotinylated and the probe DNA oligonucleotides (SeqTag) are synthesized with a 5'-biotin modification. Then, by taking advantage of streptavidin's native tetrameric form, three DNA strands are bound to each antibody. As opposed to chemical conjugation methods, which can harm the antibody, this method proves gentle enough to preserve antibody function. As shown a single streptavidin molecule (2) is bound to three of the same DNA SeqTags (1) and a single antibody (3).

Figure 13:
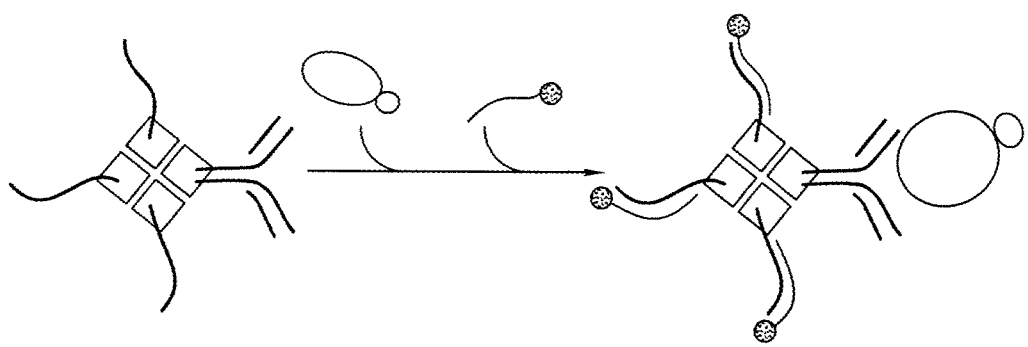

FIG. 13 is a schematic representation of detection of an analyte by the SeqTag labeled antibody shown in FIG. 12.

Figure 14:
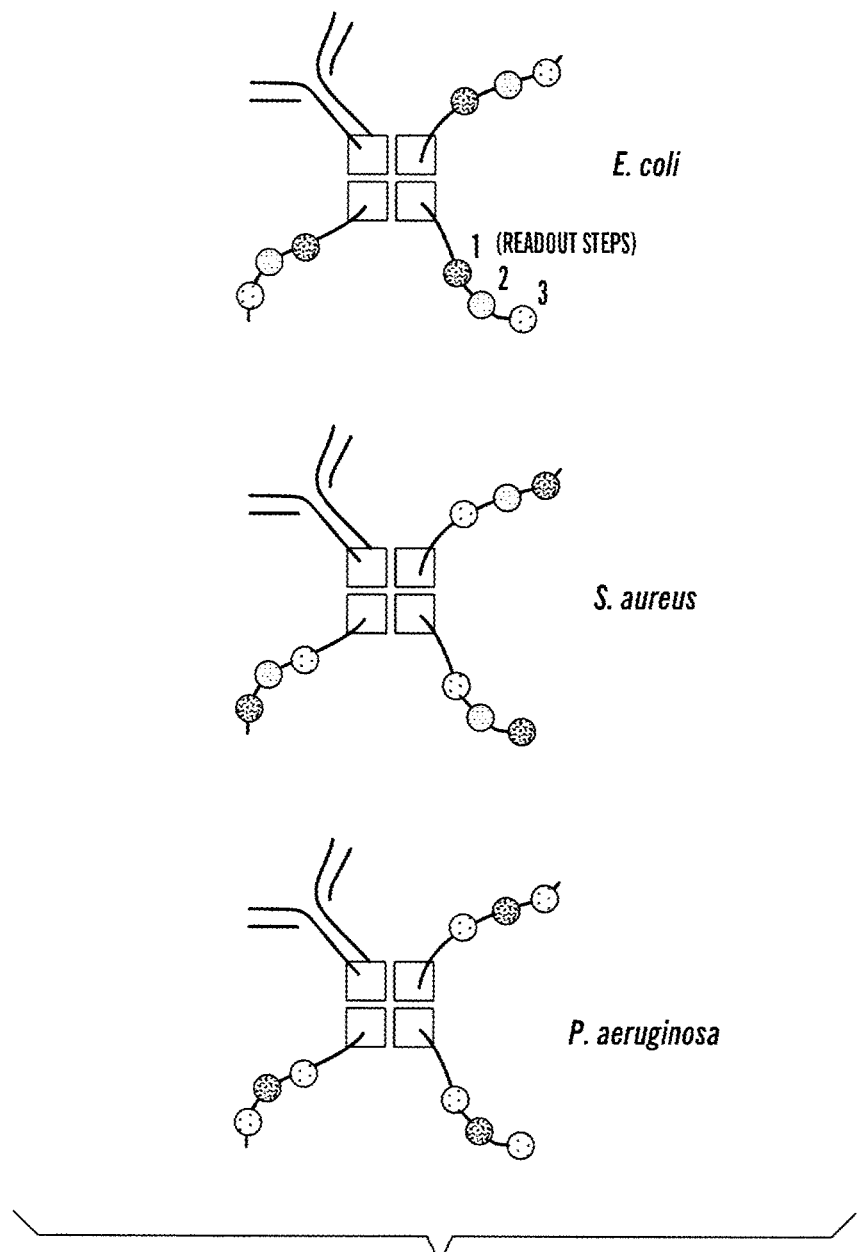

FIG. 14 is a schematic representation of detection reagents for different analytes. As shown, different infectious agent (analytes) can each be assigned their own SeqTag code to enable multiplexed detection according to an embodiment described herein.

Figure 15:

FIG. 15 is a schematic representation of detection reagents for SeqTagged Fluorescence in situ hybridization (FISH). FISH permits microbes to be identified based on their ribosomal RNA sequence. In the case of SeqTagged FISH, the FISH probe and its SeqTag can be synthesized as a single DNA oligonucleotides as shown. Sequences shown are, from top to bottom, SEQ ID NO: 1 (5'-CCTA-CACACCAGCGTGCC-3', probe for *K. pneumonia*); SEQ ID NO: 2 (5'-CCGCACTTTCATCTTCCG-3', probe for *H. influenzae*); and SEQ ID NO: 3 (GCCAAGGCT-TATACTCGC, probe for *C. albicans*).

DETAILED DESCRIPTION OF THE INVENTION

The present invention provides a three dimensional matrix of a plurality of nucleic acids. The present invention provides a three dimensional matrix including a plurality of nucleic acids bound thereto. According to one aspect, the matrix is a three dimensional nucleic acid-containing polymer. The nucleic acids may be naturally occurring nucleic acids or non-naturally occurring nucleic acids, such as nucleic acids that have been made using synthetic methods. The nucleic acids in the three dimensional matrix may be ordered or unordered. The nucleic acids in the three dimensional matrix may be present in their natural spatial relationship within a cell, tissue or organism. The nucleic acids in the three dimensional matrix may be present in rows and columns within the three dimensional matrix.

According to one aspect, the nucleic acids are modified to incorporate a functional moiety for attachment to the matrix. The functional moiety can be covalently cross-linked, copolymerize with or otherwise non-covalently bound to the matrix. The functional moiety can react with a cross-linker. The functional moiety can be part of a ligand-ligand binding pair. dNTP or dUTP can be modified with the functional group, so that the function moiety is introduced into the DNA during amplification. A suitable exemplary functional moiety includes an amine, acrydite, alkyne, biotin, azide, and thiol. In the case of crosslinking, the functional moiety is cross-linked to modified dNTP or dUTP or both. Suitable exemplary cross-linker reactive groups include imidoester (DMP), succinimide ester (NHS), maleimide (Sulfo-SMCC), carbodiimide (DCC, EDC) and phenyl azide. Cross-linkers within the scope of the present disclosure may include a spacer moiety. Such spacer moieties may be functionalized. Such spacer moieties may be chemically stable. Such spacer moieties may be of sufficient length to allow amplification of the nucleic acid bound to the matrix. Suitable exemplary spacer moieties include polyethylene glycol, carbon spacers, photo-cleavable spacers and other spacers known to those of skill in the art and the like.

According to one aspect, a matrix-forming material is contacted to a plurality of nucleic acids spatially arrange in three-dimensions relative to one another.

Matrix forming materials include polyacrylamide, cellulose, alginate, polyamide, cross-linked agarose, cross-linked dextran or cross-linked polyethylene glycol. The matrix forming materials can form a matrix by polymerization and/or crosslinking of the matrix forming materials using methods specific for the matrix forming materials and methods, reagents and conditions known to those of skill in the art.

According to one aspect, a matrix-forming material can be introduced into a cell. The cells are fixed with formaldehyde and then immersed in ethanol to disrupt the lipid membrane. The matrix forming reagents are added to the sample and are allowed to permeate throughout the cell. A polymerization inducing catalyst, UV or functional cross-linkers are then added to allow the formation of a gel matrix. The unincorporated material is washed out and any remaining functionally reactive group is quenched. Exemplary cells include any cell, human or otherwise, including diseased cells or healthy cells. Certain cells include human cells, non-human cells, human stem cells, mouse stem cells, primary cell lines, immortalized cell lines, primary and immortalized fibroblasts, HeLa cells and neurons.

According to one aspect, a matrix-forming material can be used to encapsulate a biological sample, such as a tissue sample. The formalin-fixed embedded tissues on glass slides are incubated with xylene and washed using ethanol to remove the embedding wax. They are then treated with Proteinase K to permeabilized the tissue. A polymerization inducing catalyst, UV or functional cross-linkers are then added to allow the formation of a gel matrix. The unincorporated material is washed out and any remaining functionally reactive group is quenched. Exemplary tissue samples include any tissue samples of interest whether human or non-human. Such tissue samples include those from skin tissue, muscle tissue, bone tissue, organ tissue and the like. Exemplary tissues include human and mouse brain tissue sections, embryo sections, tissue array sections, and whole insect and worm embryos.

The matrix-forming material forms a three dimensional matrix including the plurality of nucleic acids. According to one aspect, the matrix-forming material forms a three dimensional matrix including the plurality of nucleic acids while maintaining the spatial relationship of the nucleic acids. In this aspect, the plurality of nucleic acids are immobilized within the matrix material. The plurality of nucleic acids may be immobilized within the matrix material by co-polymerization of the nucleic acids with the matrix-forming material. The plurality of nucleic acids may also be immobilized within the matrix material by crosslinking of the nucleic acids to the matrix material or otherwise cross-linking with the matrix-forming material. The plurality of nucleic acids may also be immobilized within the matrix by covalent attachment or through ligand-protein interaction to the matrix.

According to one aspect, the matrix is porous thereby allowing the introduction of reagents into the matrix at the site of a nucleic acid for amplification of the nucleic acid. A porous matrix may be made according to methods known to those of skill in the art. In one example, a polyacrylamide gel matrix is co-polymerized with acrydite-modified streptavidin monomers and biotinylated DNA molecules, using a suitable acrylamide:bis-acrylamide ratio to control the cross-linking density. Additional control over the molecular sieve size and density is achieved by adding additional cross-linkers such as functionalized polyethylene glycols. According to one aspect, the nucleic acids, which may represent individual bits of information, are readily accessed by oligonucleotides, such as labeled oligonucleotide probes, primers, enzymes and other reagents with rapid kinetics.

According to one aspect, the matrix is sufficiently optically transparent or otherwise has optical properties suitable for standard Next Generation sequencing chemistries and deep three dimensional imaging for high throughput information readout. The Next Generation sequencing chemistries that utilize fluorescence imaging include ABI SoLiD (Life Technologies), in which a sequencing primer on a template is ligated to a library of fluorescently labeled nonamers with a cleavable terminator. After ligation, the beads are then imaged using four color channels (FITC, Cy3, Texas Red and Cy5). The terminator is then cleaved off leaving a free-end to engage in the next ligation-extension cycle. After all dinucleotide combinations have been determined, the images are mapped to the color code space to determine the specific base calls per template. The workflow is achieved using an automated fluidics and imaging device (i.e. SoLiD 5500 W Genome Analyzer, ABI Life Technologies). Another sequencing platform uses sequencing by synthesis, in which a pool of single nucleotide with a cleavable terminator is incorporated using DNA polymerase. After imaging, the terminator is cleaved and the cycle is repeated. The fluorescence images are then analyzed to call bases for each DNA amplicons within the flow cell (HiSeq, Illumia).

According to certain aspects, the plurality of nucleic acids may be amplified to produce amplicons by methods known to those of skill in the art. The amplicons may be immobilized within the matrix generally at the location of the nucleic acid being amplified, thereby creating a localized colony of amplicons. The amplicons may be immobilized within the matrix by steric factors. The amplicons may also be immobilized within the matrix by covalent or noncovalent bonding. In this manner, the amplicons may be considered to be attached to the matrix. By being immobilized to the matrix, such as by covalent bonding or crosslinking, the size and spatial relationship of the original amplicons is maintained. By being immobilized to the matrix, such as by covalent bonding or crosslinking, the amplicons are resistant to movement or unraveling under mechanical stress.

According to one aspect, the amplicons, such as DNA amplicons, are then copolymerized and/or covalently attached to the surrounding matrix thereby preserving their spatial relationship and any information inherent thereto. For example, if the amplicons are those generated from DNA or RNA within a cell embedded in the matrix, the amplicons can also be functionalized to form covalent attachment to the matrix preserving their spatial information within the cell thereby providing a subcellular localization distribution pattern.

As used herein, the term "nucleic acid" includes the term "oligonucleotide" or "polynucleotide" which includes a plurality of nucleotides. The term "nucleic acid" is intended to include naturally occurring nucleic acids and synthetic nucleic acids. The term "nucleic acid" is intended to include single stranded nucleic acids and double stranded nucleic acids. The term "nucleic acid" is intended to include DNA and RNA, whether single stranded or double stranded. Nucleotides of the present invention will typically be the naturally-occurring nucleotides such as nucleotides derived from adenosine, guanosine, uridine, cytidine and thymidine. When oligonucleotides are referred to as "double-stranded," it is understood by those of skill in the art that a pair of oligonucleotides exists in a hydrogen-bonded, helical array typically associated with, for example, DNA. In addition to the 100% complementary form of double-stranded oligonucleotides, the term "double-stranded" as used herein is also meant to include those form which include such structural features as bulges and loops (see Stryer, Biochemistry, Third Ed. (1988), incorporated herein by reference in its entirety for all purposes). As used herein, the term "polynucleotide" refers to a strand of nucleic acids that can be a variety of different sizes. Polynucleotides may be the same size as an oligonucleotide, or may be two-times, three-times, four-times, five-times, ten-times, or greater than the size of an oligonucleotide.

Oligonucleotides and/or polynucleotides may be isolated from natural sources or purchased from commercial sources. Oligonucleotide and/or polynucleotide sequences may be prepared by any suitable method, e.g., the phosphoramidite method described by Beaucage and Carruthers ((1981) Tetrahedron Lett. 22: 1859) or the triester method according to Matteucci et al. (1981) J. Am. Chem. Soc. 103:3185), both incorporated herein by reference in their entirety for all purposes, or by other chemical methods using either a commercial automated oligonucleotide synthesizer or high-throughput, high-density array methods described herein and known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain embodiments of the invention oligonucleotides and/or polynucleotides may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; incorporated herein by reference in their entirety for all purposes.

Nucleic acids may be obtained from libraries, e.g., genomic libraries, cDNA libraries and the like. Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233, incorporated herein by reference in their entirety for all purposes.

In certain embodiments, nucleic acids are those found naturally in a biological sample, such as a cell or tissue.

In still other aspects, a matrix is used in conjunction with a solid support. For example the matrix can be polymerized in such a way that one surface of the matrix is attached to a solid support (e.g., a glass surface), while the other surface of the matrix is exposed or sandwiched between two solid supports. According to one aspect, the matrix can be contained within a container.

Solid supports of the invention may be fashioned into a variety of shapes. In certain embodiments, the solid support is substantially planar. Examples of solid supports include plates such as slides, microtitre plates, flow cells, coverslips, microchips, and the like, containers such as microfuge tubes, test tubes and the like, tubing, sheets, pads, films and the like. Additionally, the solid supports may be, for example, biological, nonbiological, organic, inorganic, or a combination thereof.

Embodiments of the present invention are further directed to the amplification of nucleic acid sequences within the matrix, i.e. in situ, within the matrix. Methods of amplifying nucleic acids include rolling circle amplification in situ. In certain aspects, methods of amplifying nucleic acids involves the use of PCR, such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. U.S.A. 91:360-364; incorporated herein by reference in their entirety for all purposes). Alternative amplification methods include: self sustained sequence replication (Guatelli et al. (1990) Proc. Natl. Acad. Sci. USA 87:1874, incorporated herein by reference in its entirety for all purposes), transcriptional amplification system (Kwoh et al. (1989) Proc. Natl. Acad. Sci. US. 86:1173, incorporated herein by reference in its entirety for all purposes), Q-Beta Replicase (Lizardi et al. (1988) BioTechnology 6:1197, incorporated herein by reference in its entirety for all purposes), recursive PCR (Jaffe et al. (2000) J. Biol. Chem. 275:2619; and Williams et al. (2002) J. Biol. Chem. 277:7790; incorporated herein by reference in their entirety for all purposes) or any other nucleic acid amplification method using techniques well known to those of skill in the art. A variety of amplification methods are described in U.S. Pat. Nos. 6,391,544, 6,365,375, 6,294,323, 6,261,797, 6,124,090 and 5,612,199, incorporated herein by reference in their entirety for all purposes.

Embodiments of the present invention are directed to methods of amplifying nucleic acids in situ within the matrix by contacting the nucleic acids within the matrix with reagents and under suitable reaction conditions sufficient to amplify the nucleic acids. According to one aspect, the matrix is porous to allow migration of reagents into the matrix to contact the nucleic acids. In certain aspects, oligonucleotides are amplified by selectively hybridizing an amplification primer to an amplification site at the 3' end of an oligonucleotide using conventional methods. Amplification primers are 6 to 100, and even up to 1,000, nucleotides in length, but typically from 10 to 40 nucleotides, although oligonucleotides of different length are of use. Amplification primers may be present in solution to be added to the matrix or they may be added during formation of the matrix to be present therein sufficiently adjacent to nucleic acids to allow for hybridization and amplification.

Typically, selective hybridization occurs when two nucleic acid sequences are substantially complementary, i.e., at least about 65% 75%, 80%, 85%, 90%, 91%, 92%, 93%, 94%, 95%, 96%, 97%, 98% 99%, 99.1%, 99.2%, 99.3%, 99.4%, 99.5%, 99.6%, 99.7%, 99.8%, 99.9% or 100% complementary over a stretch of at least 14 to 25 nucleotides. See Kanehisa, M., 1984, Nucleic Acids Res. 12: 203, incorporated herein by reference in its entirety for all purposes.

Overall, five factors influence the efficiency and selectivity of hybridization of the primer to a second nucleic acid molecule. These factors, which are (i) primer length, (ii) the nucleotide sequence and/or composition, (iii) hybridization temperature, (iv) buffer chemistry and (v) the potential for steric hindrance in the region to which the primer is required to hybridize, are important considerations when non-random priming sequences are designed.

There is a positive correlation between primer length and both the efficiency and accuracy with which a primer will anneal to a target sequence; longer sequences have a higher Tm than do shorter ones, and are less likely to be repeated within a given target sequence, thereby cutting down on promiscuous hybridization. Primer sequences with a high G-C content or that comprise palindromic sequences tend to self-hybridize, as do their intended target sites, since unimolecular, rather than bimolecular, hybridization kinetics are generally favored in solution; at the same time, it is important to design a primer containing sufficient numbers of G-C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g., formamide, that might be included in a hybridization mixture, while increases in salt concentration facilitate binding. Under stringent hybridization conditions, longer probes hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of any one alone. Hybridization conditions are known to those skilled in the art and can be found in Current Protocols in Molecular Biology, John Wiley & Sons, N.Y. (1989), 6.3.1-6.3.6, incorporated herein by reference in its entirety for all purposes.

Primers are designed with the above first four considerations in mind. While estimates of the relative merits of numerous sequences are made mentally, computer programs have been designed to assist in the evaluation of these several parameters and the optimization of primer sequences (see, e.g., Hoover et al. (2002) Nucleic Acids Res. 30:e43, and Rouillard et al. (2004) Nucleic Acids Res. 32:W176, incorporated by reference herein in their entirety for all purposes).

In accordance with certain examples, methods of sequencing nucleic acid in situ within a matrix are provided. General sequencing methods known in the art, such as sequencing by extension with reversible terminators, fluorescent in situ sequencing (FISSEQ), pyrosequencing, massively parallel signature sequencing (MPSS) and the like (described in Shendure et al. (2004) Nat. Rev. 5:335, incorporated herein by reference in its entirety), are suitable for use with the matrix in which the nucleic acids are present. Reversible termination methods use step-wise sequencing-by-synthesis biochemistry that coupled with reversible termination and removable fluorescence (Shendure et al. supra ands U.S. Pat. Nos. 5,750,341 and 6,306,597, incorporated herein by reference. FISSEQ is a method whereby DNA is extended by adding a single type of fluorescently-labelled nucleotide triphosphate to the reaction, washing away unincorporated nucleotide, detecting incorporation of the nucleotide by measuring fluorescence, and repeating the cycle. At each cycle, the fluorescence from previous cycles is bleached or digitally subtracted or the fluorophore is cleaved from the nucleotide and washed away. FISSEQ is described further in Mitra et al. (2003) Anal. Biochem. 320:55, incorporated herein by reference in its entirety for all purposes. Pyrosequencing is a method in which the pyrophosphate (PPi) released during each nucleotide incorporation event (i.e., when a nucleotide is added to a growing polynucleotide sequence). The PPi released in the DNA polymerase-catalyzed reaction is detected by ATP sulfurylase and luciferase in a coupled reaction which can be visibly detected. The added nucleotides are continuously degraded by a nucleotide-degrading enzyme. After the first added nucleotide has been degraded, the next nucleotide can be added. As this procedure is repeated, longer stretches of the template sequence are deduced. Pyrosequencing is described further in Ronaghi et al. (1998) Science 281:363, incorporated herein by reference in its entirety for all purposes. MPSS utilizes ligation-based DNA sequencing simultaneously on microbeads. A mixture of labelled adaptors comprising all possible overhangs is annealed to a target sequence of four nucleotides. The label is detected upon successful ligation of an adaptor. A restriction enzyme is then used to cleave the DNA template to expose the next four bases. MPSS is described further in Brenner et al. (2000) Nat. Biotech. 18:630, incorporated herein by reference in its entirety for all purposes.

According to certain aspects, the nucleic acids within the matrix can be interrogated using methods known to those of skill in the art including fluorescently labeled oligonucleotide/DNA/RNA hybridization, primer extension with labeled ddNTP, sequencing by ligation and sequencing by synthesis. Ligated circular padlock probes described in Larsson, et al., (2004), Nat. Methods 1:227-232 can be used to detect multiple sequence targets in parallel, followed by either sequencing-by-ligation, -synthesis or -hybridization of the barcode sequences in the padlock probe to identify individual targets.

According to one aspect, methods described herein produce a three dimensional nucleic acid amplicon matrix which is stable, long-lasting and resistant, substantially resistant or partially resistant to enzymatic or chemical degradation. The three dimensional nucleic acid amplicon matrix can be repeatedly interrogated using standard probe hybridization and/or fluorescence based sequencing. The three dimensional nucleic acid amplicon matrix can be repeatedly interrogated with little or no signal degradation, such as after more than 50 cycles, and with little position shift, such as less than 1 µm per amplicon.

According to one aspect, a plurality of circular DNA molecules are covalently linked to one another. The circular DNA molecules are then amplified using methods known to those of skill in the art, such as isothermal enzymatic amplification one example of which is rolling circle amplification. According to this aspect, the amplicons are localized near the circular DNA. According to this aspect, the amplicons form a shell around the circular DNA or otherwise assemble around the circular DNA. Each circular DNA may have more than 1000 amplicons surrounding or otherwise associated therewith. According to this aspect, the amplicons surrounding a particular circular DNA provide a high signal intensity, due in part to the number of amplicons and/or detectable labels associated with the amplicons. The amplicons may be functionalized and cross-linked or otherwise covalently bound together around their associate circular DNA to form a series or network of tightly bound DNA amplicon shells around each circular DNA. The series or network of tightly bound DNA amplicon shells around each circular DNA may be assembled onto a three-dimensional support. According to one aspect, the series or network of tightly bound DNA amplicon shells around each circular DNA may be assembled onto a three-dimensional support producing a three dimensional DNA polymer with defined overall shape, size and amplicon position.

According to one aspect, amplicons are covalently linked without the need for separate cross-linkers, such as bis-N-succinimidyl-(nonaethylene glycol) ester. An acrydite moiety, such as a catalyst activated acrydite moiety is introduced at the end of a long carbon spacer (i.e., about C6 to about C12) at position 5 of a uracil base a representative formula of which is shown below.

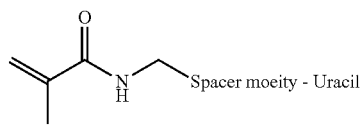

In the formula below, R represents the acrydite spacer moiety attached to the 5 position of the uracil base.

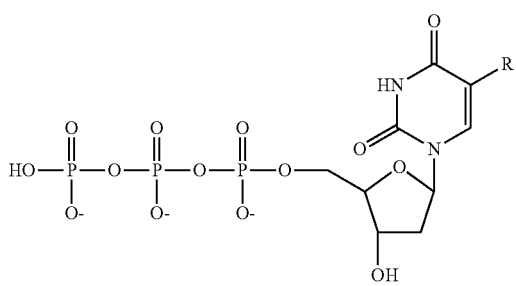

When copolymerized with bis-acrylamide in the presence of a catalyst, a polymerization reaction takes place, encapsulating the circular DNA with the amplicons and fixing the amplicons in position. The chemically inert nature of the polymerized mixture allows various downstream applications. The spacer can be a carbon chain of between about 2 carbons to about 200 carbons. The spacer can be polyethylene glycol. The length of the spacer can vary from about 30 angstroms to about 100 angstroms and can be of various molecular weights. The spacer can be permanent or reversible, such as by using UV light, enzymes, chemical cleavage, etc. A three dimensional matrix, such as a polyacrylamide gel matrix, can be used to embed a variety of biological structures containing enzymatically or chemically modified DNA or RNA molecules containing an acrydite functional moiety or moieties. The non-nucleic acid component is selectively dissolved using detergents, proteases, organic solvents or denaturants to create a three dimensional matrix that preserves individual DNA or RNA molecules and their relative spatial location. Examples include embedding cells, healthy and diseased tissues and tissue sections, small model organisms such as worms and insects, bacterial colonies or biofilm, environmental samples containing other DNA or RNA containing materials or organisms.

Described herein are methods, detection reagents (or detection molecules as used interchangeably herein) and kits for detecting a plurality of analytes in a sample. In accordance with embodiments of various aspects described herein, a probe reagent (e.g., antibody or aptamers) can be directly or indirectly labeled with a nucleic acid label. The nucleic acid information present on the nucleic acid label can then be decoded and/or detected in a temporally-sequential manner. The detection reagents and methods described herein significantly increase the number of different probes (and corresponding analytes) that can be simultaneously detected in a multiplex assay, as compared to an traditional assay where each probe is labeled with only fluorescent labels or quantum dots, and thus multiplexing is limited by the number of available and practically usable colors. Furthermore, because the detection reagents described herein are detected and/or imaged in a temporal series of steps, the number of probes (and corresponding analytes) that can be detected in a multiplex assay grows multiplicatively with the number of detection steps in a time series and the number of optical labels being used. By way of example only, 3 set of images in which 4 distinct optical labels are used can encode 4×4×4=64 distinct probe reagents (e.g., antibodies).

Methods of Detecting a Plurality of Analytes in a Sample

One aspect of the inventions provides the methods for detecting a plurality of analytes in a sample, using the detection reagents described herein. The method includes (a) contacting the sample with a composition comprising a plurality of detection reagents (which will be described in detail later), wherein each subpopulation of the detection reagents targets at least one different analyte; and (b) detecting in a temporally-sequential manner said plurality of the pre-determined subsequences of said detection reagents, wherein said detection of the subsequences each generates a signal signature corresponding to said subsequence, and wherein a temporal order of the signal signatures corresponding to said plurality of the subsequences of said detection reagent identifies a subpopulation of the detection reagents. In some embodiments, the signal signature is a temporal signature. In some embodiments, the signal signature can further comprise a spatial signature. A non-limiting example of a spatial signature includes spatial location of a signal signature.

In some embodiments, the temporal order of the signal signatures corresponding to the plurality of the subsequences of the detection reagent can be unique for each subpopulation of the detection reagents. In some embodiments, at least two or more signal signatures can be used to identify the same subpopulation of the detection reagents.

In some embodiments, a detection reagent described herein can target at least two (e.g., at least two, at least three or more) distinct analytes. In some embodiments, a first subpopulation of the detection reagents can target at least one analyte different from that of a second subpopulation of the detection reagents. By way of example only, a first subpopulation of the detection reagents can target at least analyte A and analyte B, whereas a second subpopulation of the detection reagents can target at least analyate B and analyte C. The readout of these detection reagents can be distinct but overlapping. Thus, different analytes can be identified by sampling them combinatorially and determining which one binds.

As used herein, the term "temporal order of the signal signatures" refers to a sequence of signal signatures determined in a temporally-sequential manner, i.e., the sequence of signal signatures is progressed through by a number of active operations performed in a temporally-sequential manner, e.g., using a different set of decoding reagents or decoder probes in each active operation. In some embodiments, using a set of decoder probes in each active operation can yield one signal signature corresponding to one subsequence of the detection reagents.

The composition comprising a plurality of detection reagents can exist in any format. In some embodiments, the composition comprising a plurality of detection reagents can be in a form of a solution or suspension comprising the detection reagents. In such embodiments, the composition can further comprise at least one agent. For example, without wishing to be bound, the agent can be a blocking buffer, a surfactant, unconjugated probe reagents, a stabilizer, an enzyme inhibitor, or any combinations thereof. In some embodiments where the compositions are administered in vivo, the composition can further comprise a pharmaceutically-acceptable carrier. In other embodiments, the composition comprising a plurality of detection reagents can be contained or immobilized in a device (e.g., a syringe, or a microfluidic device) or an assay or reaction vessel (e.g., solid supports such as vials, and multi-well plates).

As used therein, the term "contacting" refers to any suitable means for delivering, or exposing, a sample to a plurality of the detection reagents described herein. In some embodiments, the term "contacting" refers to adding the detection reagents (e.g., suspended in a solution) directly to the sample. In some embodiments, the term "contacting" can further comprise mixing the sample with the detection reagents by any means known in the art (e.g., vortexing, pipetting, and/or agitating). In some embodiments, the term "contacting" can further comprise incubating the sample together with the detection reagents for a sufficient amount of time, e.g., to allow binding of the probe reagents to the target analytes. The contact time can be of any length, depending on the binding affinities and/or concentrations of the probe reagents and/or the analytes, concentrations of the detection reagents, and/or incubation condition (e.g., temperature). For example, the contact time can be reduced if the sample and detection reagents are incubated at a higher temperature. In some embodiments, the contact time between the sample and the detection reagents can be at least about 30 seconds, at least about 1 minute, at least about 5 minutes, at least about 10 minutes, at least about 15 minutes, at least about 30 minutes, at least about 1 hour, at least about 2 hours, at least about 3 hours, at least about 4 hours, at least about 6 hours, at least about 8 hours, at least about 10 hours, at least about 12 hours, at least about 24 hours, at least about 48 hours or longer. One of skill in the art can adjust the contact time accordingly.

For in vivo applications, the term "contacting" can refer to administering the detection reagents to a subject, e.g., by oral administration or by injection.

The sample can be contacted with at least one kind of the detection reagents. In some embodiments, the sample can be contacted with at least 2, at least 3, at least 4, at least 5, at least 6, at least 7, at least 8, at least 9, at least 10, at least 15, at least 20, at least 30, at least 40, at least 50, at least 60, at least 70, at least 80, at least 90, at least 100 or more different kinds of the detection reagents. In some embodiments, the sample can be contacted with at least 100, at least 500, at least 1000, at least 5000, at least 10,000, at least 50,000, at least 100,000 or more different kinds of the detection reagents. Various kinds of the detection reagents described herein can differ in types of probe reagents (e.g., nucleic acids vs. antibodies), target binding domains, and/or target analytes.

In some embodiments, the method described herein can further comprise processing the sample before contacting with the composition comprising a plurality of detection reagents described herein. Depending on the types and/or natures of the samples and/or analytes, different sample processing techniques can be used with the methods described herein. Exemplary sample processing techniques include, but are not limited to, mechanical processing of a sample (e.g., without limitations, homogenizing, centrifuging, vortexing, sectioning and shearing), addition of at least one reagent to a sample (e.g., without limitations, lysis buffers, RNA or DNA extraction reagents, RNA or DNA digestion reagents, enzyme inhibitors, fixing agents, organic solvents, antibodies, permeabilizing agents and immunohistochemistry agents), separation of a sample (e.g., without limitations, filtering, centrifuging, electrophoresis, western blot, and Northern blot), mounting a sample on a solid support (e.g., a microscopic slide), and any combinations thereof.

By way of example only, if a sample is a tissue from a subject (e.g., a biopsy for immunostaining), sample processing can include, but are not limited to, tissue sectioning, mounting on a solid support, fixing the tissue, permeabilizing the tissue (if intracellular proteins are to be detected), blocking non-specific reactions with the detection reagents. In some embodiments, proteins or nucleic acids can be isolated from a tissue or fluid sample and then separated electrophoretically on a separation medium (e.g., electrophoresis gel), followed by transferring the proteins or nucleic acids to a blotting membrane. The blotting membranes containing proteins or nucleic acids can then be contacted with the detection reagents described herein. Methods of processing samples before addition of various types of probe reagents for different kinds of assays are well established in the art, and any of those methods can be performed prior to the contacting step of the methods described herein.

In some embodiments, the method described herein can further comprise removing any unbound detection reagents before detection of the pre-determined subsequences in a temporally-sequential manner. The term "unbound detection reagents" as used herein refers to detection reagents that have not bound to or interacted with target analytes. The unbound detection reagents can be removed from the sample by any methods known in the art, e.g., rinsing with the sample with a buffered solution at least once, at least two times, at least three times or above.

After the detection reagents bind to the target analytes in a sample, the nucleic acid labels of the detection reagents carrying nucleic-acid information can be decoded to allow identification of respective probe reagent(s) conjugated to them, as opposed to traditional optical labeling technologies, where an optical signature such as a fluorophore is detected in the absence of providing any nucleic acid information. In embodiments of various aspects described herein, the pre-determined subsequences within the nucleic acid labels are detected in a temporally-sequential manner. The term "temporally-sequential manner" is used in reference to detecting or decoding in a time series a plurality of the pre-determined subsequences within the nucleic acid labels of any detection reagents that are bound to target analytes in a sample. In some embodiments, one or more pre-determined subsequences within at least one nucleic acid label of each detection reagent can be detected or decoded at each time point or detection step of a time series. In some embodiments, one pre-determined subsequence within at least one nucleic acid label of each detection reagent can be detected or decoded at each time point or detection step of a time series. In some embodiments, at least one pre-determined subsequence (e.g., 1, 2, 3, 4, 5, 6, or more pre-determined subsequences) at the same corresponding location within the nucleic acid label of each detection reagent can be detected or decoded at each time point or detection step of a time series. The time period between any two time points or detection steps can be of any length, e.g., seconds, minutes and hours. For example, the time period between any two time points or detection steps can vary from about 5 seconds to about 2 hours, from about 10 seconds to about 1 hour, from about 30 seconds to about 30 mins, or from about 1 min to about 15 mins. In some embodiments, the time period between any two time points or detection steps can be less than 5 seconds. In other embodiments, the time period between any two time points or detection steps can be longer than 2 hours, longer than 4 hours, longer than 6 hours, longer than 12 hours, longer than 1 day. For example, a sample containing the detection reagents can be maintained at room temperature, at a fridge temperature (e.g., between about 0° C. and about 10° C.) or at sub-zero temperatures (e.g., between −80° C. or lower and 0° C.) during the time period between detection steps. In some embodiments, each subsequent detection step is performed substantially immediately one after another (e.g., within less than 2 seconds, less than 1 second).

In some embodiments, the pre-determined subsequences can be detected in any temporal orders. In some embodiments, the next pre-determined subsequence to be detected after the previous one can be located closest to the previous one. In some embodiments, the next pre-determined subsequence to be detected after the previous one can be located at least one, at least two, at least three, at least four, at least five or more pre-determined subsequences apart from the previous one. In such embodiments, any pre-determined subsequences that were bypassed in a previous detection step can be detected afterward. In some embodiments of the methods described herein, a computer-implemented software can be used to facilitate an analysis of the temporal readouts from the detection steps, e.g., re-arranging the temporal readouts in an order corresponding to their spatial locations within the nucleic acid label before further comparison and quantification analyses.

Figure 1:
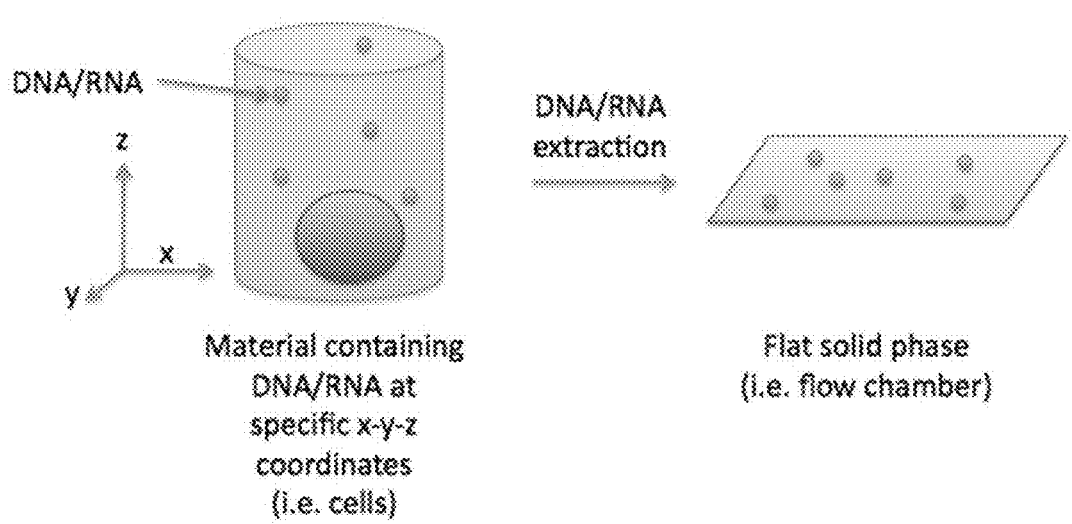
FIG. 1 depicts a schematic of nucleic acids at relative positions within a three dimension environment and extraction and placement onto a two dimensional environment, such as a glass slide or flow chamber.
Figure 2:
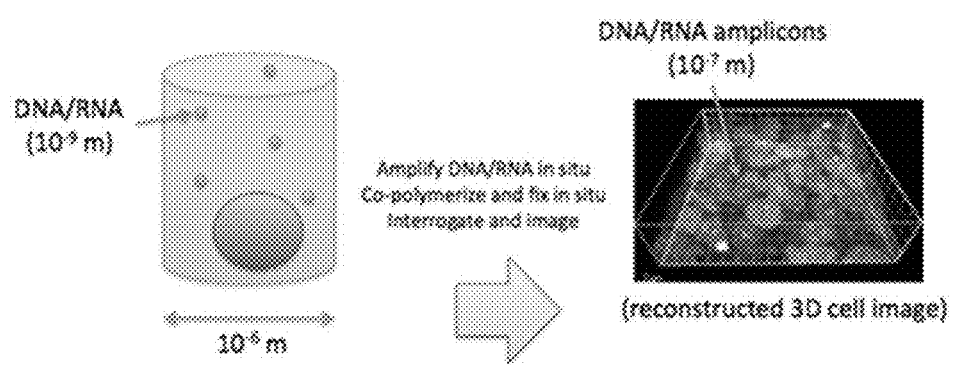
FIG. 2 depicts in schematic the process of creating a matrix of nucleic acids within cells in situ, followed by amplifying the nucleic acids, such as DNA or RNA, in situ, co-polymerizing the amplicons in situ, covalently attaching the amplicons to the matrix material, interrogating the amplicons and imaging the amplicons along with a reconstructed 3D cell image with DNA/RNA amplicons on the order of 10-7 m.
Figure 3:
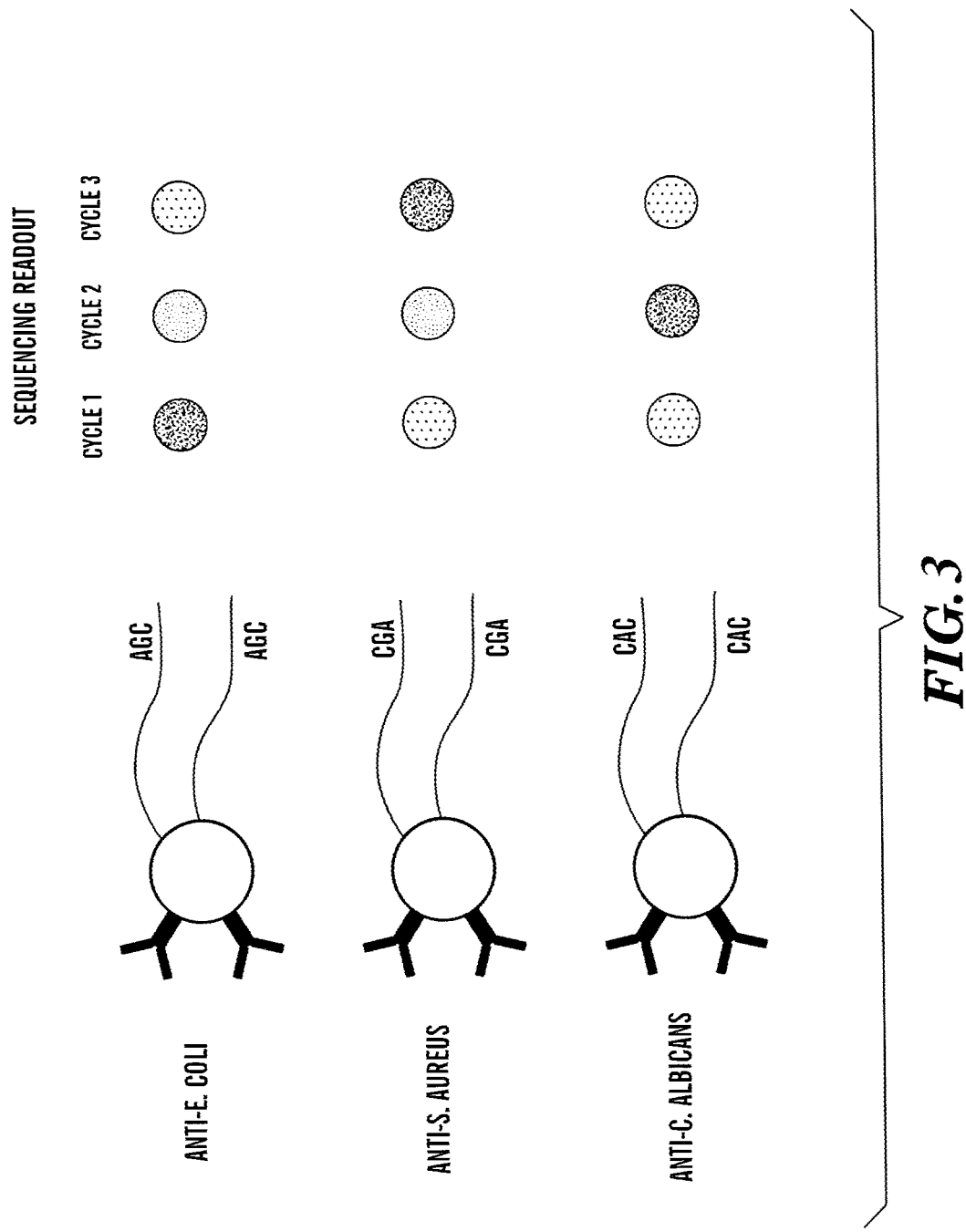
FIG. 3 shows three different embodiments of the detection reagents described herein producing distinct sequencing readout. Pathogen-specific antibodies (e.g., anti-$E.$ $coli$, anti-$S.$ $aureus$, and anti-$C.$ $albicans$) are individually conjugated to a nanoparticle with at least one nucleic acid label as described herein. In accordance with one or more embodiments, the readout of the nucleic acid label can take the form of a set of optical images or spot-readings of, e.g., fluorescent or visible colors; the temporal sequence of optical images or spot-readings can then be computationally analyzed to determine the identity of the corresponding probe reagent, e.g., a pathogen-specific antibody.
Figure 4:
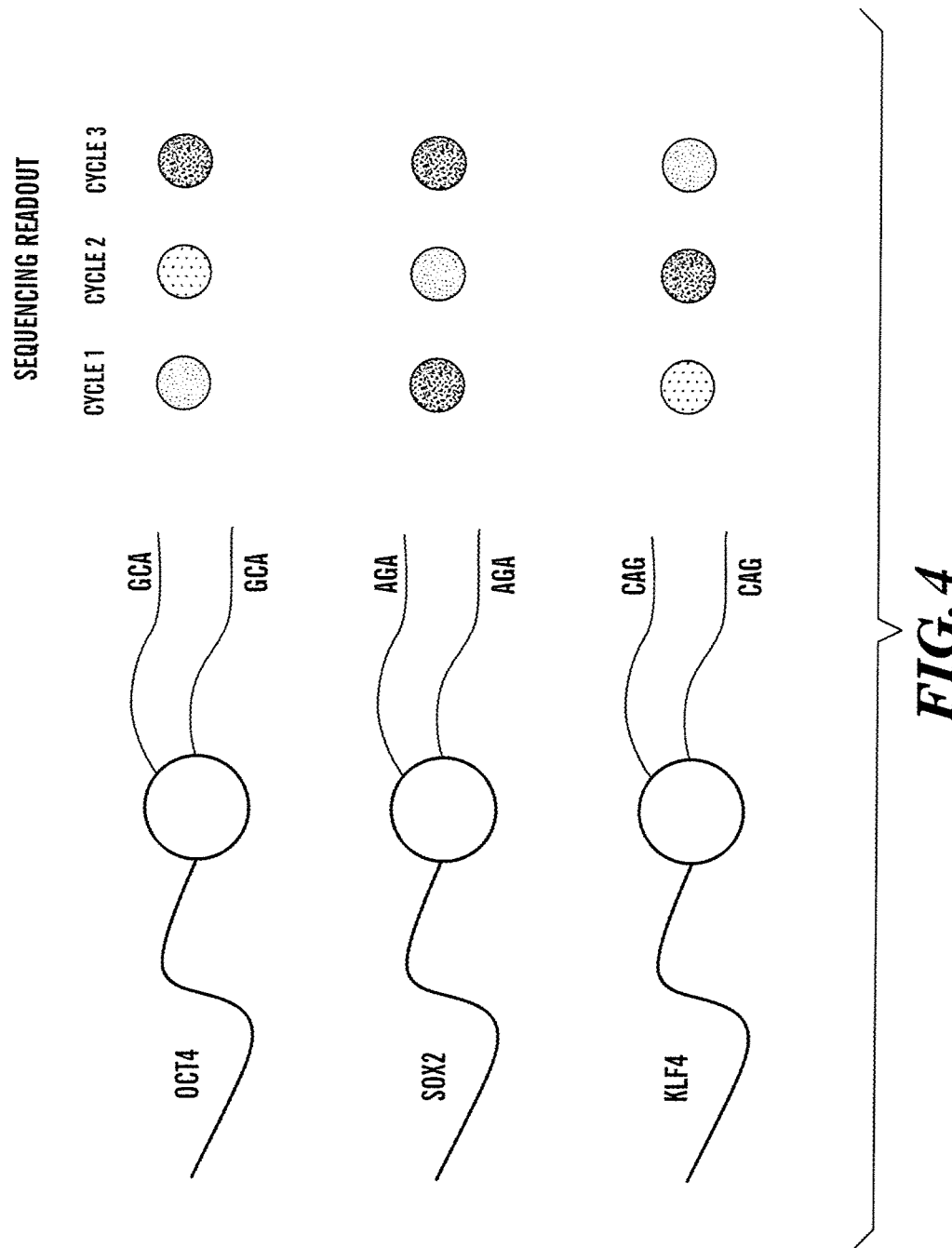
FIG. 4 shows three different embodiments of the detection reagents described herein producing distinct sequencing readout. DNA oligonucleotides complementary to target RNA expression (e.g., OCT4, SOX2, or KLF4) are individually conjugated to a nanoparticle with at least one nucleic acid label as described herein. In accordance with one or more embodiments, the readout of the nucleic acid label can take the form of a set of optical images or spot-readings of, e.g., fluorescent or visible colors; the temporal sequence of optical images or spot-readings can then be computationally analyzed to determine the identity of the corresponding probe reagent, e.g., a DNA aptamer specific for a RNA expression.
Figure 5:
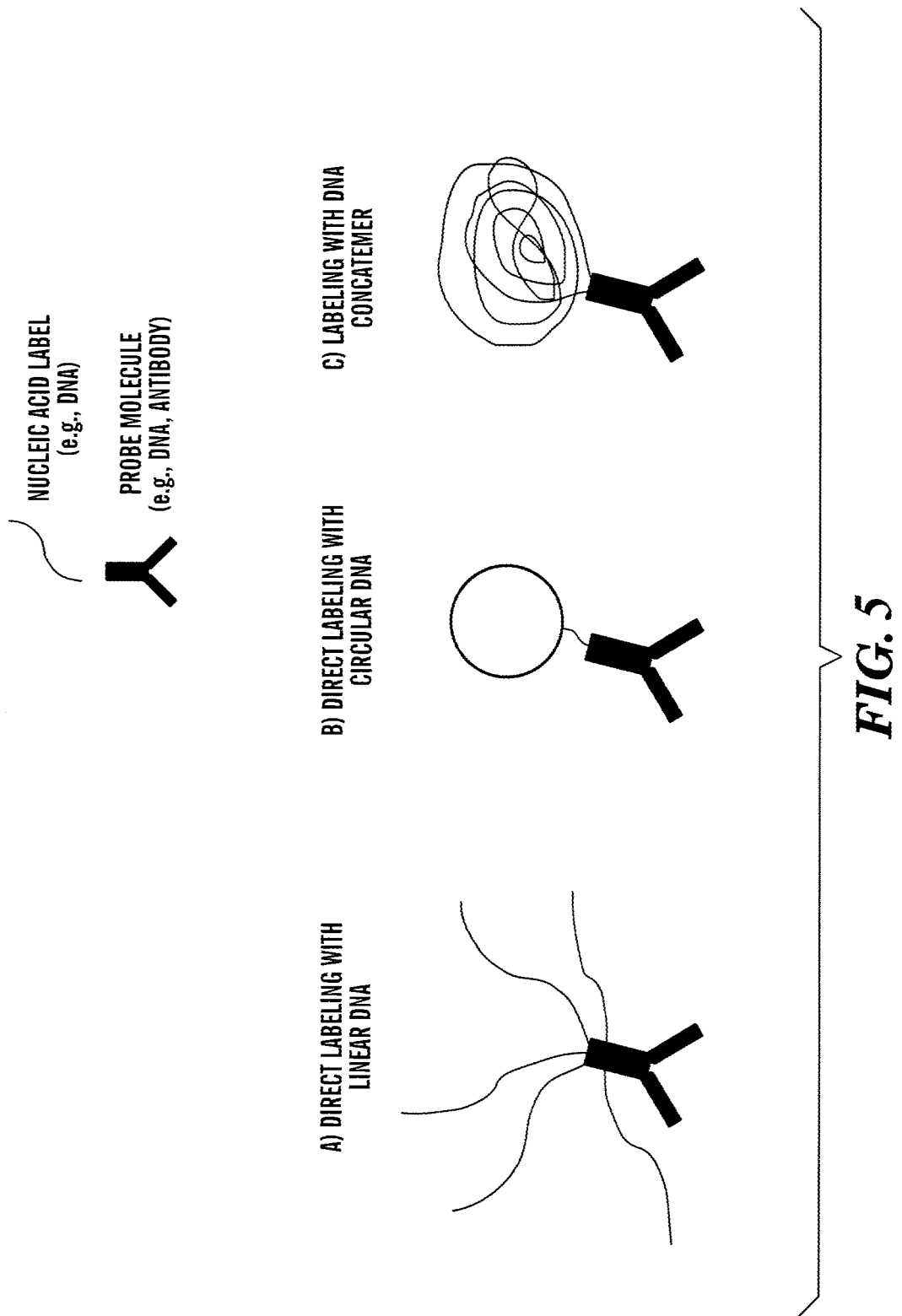
FIG. 5 shows exemplary forms of a nucleic acid label of the detection reagent according to one or more embodiments described herein.

In some embodiments, the detection or decoding of the pre-determined subsequences can comprise nucleic acid sequencing. Methods for sequencing nucleic acids are well established to a skilled artisan, e.g., but not limited to ligation, hybridization, synthesis, amplification or single-base extension, or any combinations thereof. By way of example only, as shown in FIG. 3 or FIG. 4, the nucleic acid labels each contain three pre-determined subsequences (each of one nucleotide) conjugated together by a direct bond such as a phosphodiester bond. Each sequencing step decodes or determines one nucleotide, wherein each nucleobase (A, G, C or T) generates a distinct signal signature corresponding to the nucleobase. Consequently, a temporal order or time series of the signal signatures generated from each sequencing step corresponds to the respective probe reagent, and thus identify the target analyte. Without wishing to be bound, in this embodiment, the number of sequencing steps performed is not necessarily equal to the number of the pre-determined sequences. In some embodiments, the number of sequencing steps performed can be less than the number of the pre-determined sequences. For example, as shown in FIG. 3, two sequencing steps could be sufficient to identify the three different probe reagents, where each base is associated with a different color. However, additional nucleic acid information can increase the accuracy of identifying different probe reagents. Further, if the sequencing of each base can yield one of 4 colors, the n-base subsequences (e.g., 3-base subsequences shown in FIG. 3 or FIG. 4) can produce $4^n$ possible unique readouts, i.e., $4^n$ possible distinct probe reagents can be distinguished using such detection reagents described herein.

While sequencing methods can convey single base difference, other detection or decoding methods that convey information by the presence or absence of entire hybridization "sites" or pre-determined subsequences on the nucleic acid label can also be used for the methods described herein. In some embodiments, the detection step can comprise hybridizing a decoder probe with a subsequence on the nucleic acid label of the detection reagent, wherein the decoder probe can comprise a detectable label. In particular embodiments, the detection method can comprise: (a) hybridizing a set of decoder probes with a subsequence of the detection reagents, wherein each subpopulation of the decoder probes can comprise a detectable label, each detectable label producing a signal signature; (b) detecting said signal signature produced by the hybridization of said set of decoder probes; and (d) repeating steps (a) and (b) for other subsequences of said detection reagents.

In some embodiments, each subpopulation of the decoder probes can comprise a different detectable label, each different detectable label producing a different signal signature. In these embodiments, the different signal signature produced by the hybridization of the set of decoder probes can be detected.

In some embodiments, each subpopulation of the decoder probes can be complementary (e.g., partially complementary or completely complementary) to the subsequence of the detection reagents. In some embodiments, a first subpopulation and a second subpopulation of the decoder probes can be complementary (e.g., partially complementary or completely complementary) to distinct subsequences of the detection reagents. In some embodiments, at least two or more subpopulations of the decoder probes can bind to the same subsequence of the detection reagents. For example, a first subpopulation and a second subpopulation of the decoder probes can be complementary (e.g., partially complementary or completely complementary) to the same subsequence of the detection reagents.

Figure 7:
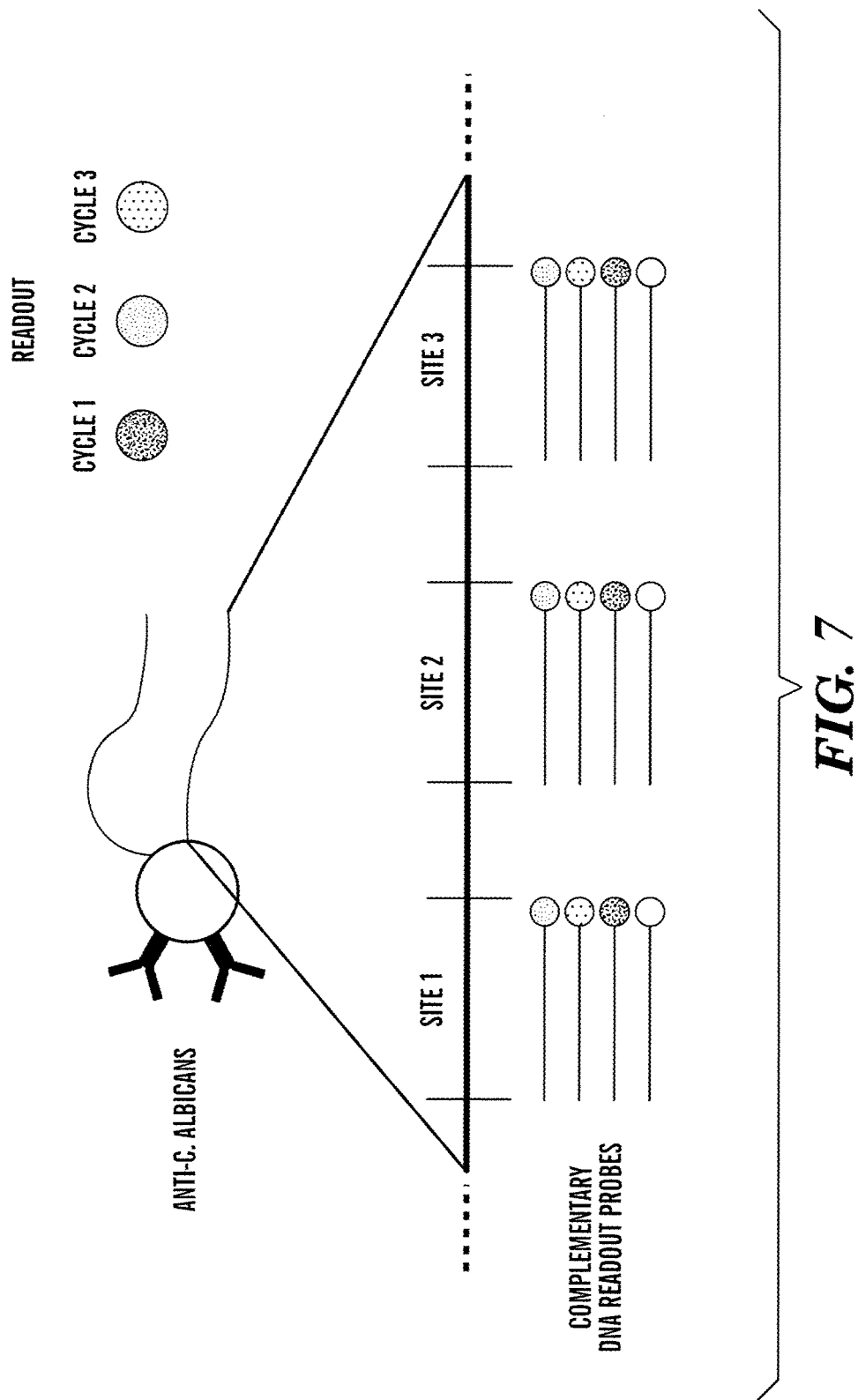
FIG. 7 shows one embodiment of the detection reagents for an exemplary hybridization-based readout method, in accordance with one or more embodiments described herein. Pathogen-specific antibodies (e.g., anti-$C.$ $albicans$) are individually conjugated to a nanoparticle comprising at least one nucleic acid label as described herein. In accordance with one or more embodiments, the readout of the nucleic acid label can be determined by hybridizing it with a small number of, e.g., fluorescently-labeled decoder probes, imaging, and then advancing to the next set of decoder probes. In order to allow the SeqTag to be read out quickly and without the use of enzymes or chemical reactions, the DNA oligonucleotide (SeqTag) is designed to include several hybridization sites, each corresponding to a particular readout step. At each readout step, the sample is subjected to a mixture of fluorescently labeled DNA probes that could potentially bind that step's hybridization site. Each of the sites, however, is designed to bind only one of these probes, thus revealing the SeqTag's identifying code.

By way of example only, FIG. 7 shows an exemplary detection reagent comprising anti-*C. albicans* probe reagents and nucleic acid labels containing three hybridization sites or pre-determined subsequences conjugated together by sequence linkers. In the first hybridization step, a first set of decoder probes each comprising a distinct detectable label (e.g., complementary DNA readout probes shown in FIG. 7, each comprising a distinct optical label) is hybridized with a first pre-determined subsequence (e.g., Site 1 in FIG. 7), followed by detection of a first signal signature produced by the hybridization. In the second hybridization step, a second set of decoder probes each comprising a distinct detectable label is hybridized with a second pre-determined subsequence (e.g., Site 2 in FIG. 7), followed by detection of a second signal signature produced by the hybridization. The second pre-determined subsequence can be the same or different from the first pre-determined subsequence. However, in preferred embodiments, the second pre-determined subsequence is different from the first pre-determined subsequence, e.g., to minimize cross-hybridization with each other. Accordingly, the hybridization and signal detection steps are repeated for other subsequences of the detection reagents with a different set of decoder probes, thereby producing a temporal order or time series of the signal signatures corresponding to the respective probe reagent (and detection reagent).

As used herein, the term "decoder probe" refers an oligonucleotide with a sequence complementary to a pre-determined sequence of the nucleic acid label. By "complementary" is meant that a nucleic acid can form hydrogen bond(s) with another nucleic acid sequence by either traditional Watson-Crick or other non-traditional types. The decoder probe sequence can be completely or partially complementary to a pre-determined sequence. In some embodiments, partial complementarity is indicated by the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "completely complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other.

The decoder probe can have a sequence of any length. In some embodiments, the decoder probe can have a sequence length of about 1 to about 100 nucleotides, about 1 to about 50 nucleotides, about 2 to about 50 nucleotides, about 5 to about 30 nucleotides, or about 5 to about 20 nucleotides.

In some embodiments, the decoder probe can comprise at least one detectable label described herein. In some embodiments, the detectable label can be an optical label selected from the group consisting of a small-molecule dye, a fluorescent molecule or protein, a quantum dot, a colorimetric reagent, a chromogenic molecule or protein, a Raman label, and any combinations thereof. In some embodiments, the detectable label or optical label can be a fluorescent molecule or protein.

In some embodiments, the decoder probe can be modified, e.g., base modification or activated with a functional group for linkage to a detectable label.

The number of decoder probes in each set can vary, depending on the number of distinct subsequences in each hybridization. In some embodiments, there can be about 1 to about 100 decoder probes, about 2 to about 50 decoder probes, about 4 to about 20 decoder probes in each set. In some embodiments, there can be about 1, 2, 3, 4, 5, 6, 7, 8, 9, 10, 11, 12, 13, 14, 15, 16, 17, 18, 19, 20, 30, 40, 50 or more decoder probes in each set. In some embodiments, while each subsequence site can hybridize with a large number of decoder probes, each set of decoder probes added in each readout step to hybridize with the subsequence site within the detection reagents can generally have as many as the number of available fluorescent colors. For example, each set of the decoder probes added in each readout step to hybridize with the subsequence site of the detection reagents can contain about 3-4 decoder probes, each of which is labeled with a distinct fluorescent color. In the case of using quantum dots or Raman labels as detection labels, there can be more than 3-4 decoder probes in each set added during each readout step.

Without wishing to be bound, an example of "non-overlapping nucleic acid labels" or "non-overlapping SeqTag labels" (i.e., no two decoder probes will hybridize with the same spatial site of the nucleic acid label) is shown herein for illustrative purposes. Assuming there are 12 pre-determined subsequences (e.g., nucleic acid sequences) designed for minimal cross-hybridization with each other and each others' complements (e.g., A1, A2, A3, A4, B1, B2, B3, B4, C1, C2, C3, and C4). Consider a detection reagent comprising a nucleic acid label of the form:

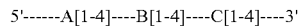

5'------A[1-4]----B[1-4]----C[1-4]----3' where each position (e.g., A[1-4]) holds only one of the subsequences (e.g., A2). Now, this subsequence is decoded or detected by using decoder probes or complementary probes A1*-A4* each labeled in one of four fluorescent colors. After readout, the signal produced by the fluorophore can be removed (e.g., denaturing to undo the hybridization (and thus removing the fluorophore)) before continuing with B1*-B4*. Since each step yields one of four outcomes, this coding scheme can provide 4×4×4=64 unique readouts. These hybridization-based probes can be used to label 64 different probe reagents that can be read out in three cycles.

In the case where two decoder probes can overlap, a single site (e.g., A in the above nucleic acid label form), which can accept one of the different decoder probes, can be used. This single site can be read out by subjecting it to the different decoder probes, e.g., in sets of 4 using the nucleic acid label form as shown above. When the correct set is reached, the nucleic acid label, e.g., SeqTag label, should be dark (no-color). This example is not construed to be limiting and any modifications apparent to one of skill in the art is also within the scope of the inventions.

The advantage of readout by hybridization is that it can be quick: hybridization can take place in minutes or less. Furthermore, no chemistry or enzymes are required during the readout process, as the readout process can be performed by similar methods as used in nucleic acid sequencing, microscopy, spectroscopy, or any combinations thereof. Thus, hybridization-based readout method can reduce cost, reduce reagent storage and/or simplify the process.

In some embodiments of the methods described herein, there can be no limit in the spatial movement of an analyte in a sample during a temporal detection of the detection reagents, for example, provided that the analyte stay within the field of detection and there is at least one same distinguishable feature in each image taken during a temporal detection so that the images can be aligned to each other based on the same distinguishable feature. In some embodiments where there is no such distinguishable feature, the spatial movement of an analyte in a sample can be less than 100 µm, including less than 50 µm, less than 25 µm, less than 10 µm, less than 1 µm or smaller, over a time period, during which a temporal detection of the detection reagents occurs. In some embodiments, the spatial movement of an analyte in a sample can be less than 1000 nm, including less than 500 nm, less than 250 nm, less than 100 nm, less than 50 nm, less than 10 nm or smaller, over a time period, during which a temporal detection of the detection reagents occurs. More importantly, the spatial movement limit of an analyte in a sample during a temporal detection is determined by the ability of matching distinguishable features between images taken during a temporal detection, which can be affected by imaging conditions. In some embodiments, the analyte can be fixed on a solid substrate or support. In some embodiments where there is or expects to be a spatial movement of an analyte during temporal detection, the location of the analyte with respect to a sample during each detection step can be determined and registered. Such spatial shift can then be corrected afterward during signal analysis using any art-recognized computer-implemented algorithms.

The length of time required to perform a temporal detection of the detection reagents (e.g., the length of time it takes to obtain a temporal sequence of signal signatures for the detection reagents) can vary, depending on the number of pre-determined subsequences to be detected or read and/or the number of available detection signals (e.g., fluorescent color and/or brightfield) to be read. In some embodiments, the length of time required to perform a temporal detection of the detection reagents can be, for example, but not limited to, 5 seconds, 10 seconds, 15 seconds, 20 seconds, 30 seconds, 1 mins, 2 mins, 3 mins, 4 mins, 5 mins, 15 mins, 30 mins, 1 hour, 2 hours, 4 hours, 6 hours, or longer.

The detection reagents can be detected by any means available in the art that is capable of detecting the specific signals on a given detection reagent generated during sequencing- or hybridization-based methods. Where the detection reagents (e.g., hybridized with decoder probes) are fluorescently labeled, suitable consideration of appropriate excitation sources can be readily determined. Possible sources can include but are not limited to arc lamp, xenon lamp, lasers, light emitting diodes or some combination thereof. The appropriate excitation source is used in conjunction with an appropriate optical detection system, for example an inverted fluorescent microscope, an epi-fluorescent microscope or a confocal microscope. Preferably, a microscope is used that can allow for detection with enough spatial resolution to separate distinct signals from individual detection reagents.

Exemplary methods for detection of the detection reagents that are applicable to the methods described herein include, without limitations, the methods described in U.S. Pat. No. 7,473,767, US patent publication no. 2007/0166708, and US application number US 2010/0261026, all of which are incorporated by reference herein in its entirety.

Additional methods that can be used to detect optical signatures include, but are not limited to, any spectroscopic techniques, flow cytometry, or any art-recognized methods involving an optical scanner and/or a photodetector (e.g., without limitations, a charge-coupled devices, active pixel sensors, photodiode light sensors (e.g., LEDs), optical detectors, and any combinations thereof). Non-limiting examples of spectroscopic techniques can include absorption spectroscopy, emission spectroscopy, elastic scattering spectroscopy, reflection spectroscopy, impedance spectroscopy, inelastic spectroscopy, coherent or resonance spectroscopy, surface plasmon fluorescence spectroscopy, Raman spectroscopy, and any combinations thereof. Spectroscopy techniques can be used to detect light of any wavelengths, including, but not limited to, microwave, terahertz, infrared, near infrared, visible, ultraviolet, x-ray, gamma, and any combinations thereof.

Without wishing to be limited, in some embodiments, at least one pre-determined subsequence (e.g., individual bases or hybridization regions) can correspond to no optical signature; that is the absence of color can be considered as an additional color. In other embodiments, at least one pre-determined subsequence (e.g., individual bases or hybridization regions) can correspond to a compound optical signature, e.g., two or more simultaneous fluorescence in multiple channels during detection (e.g., by microscopy).

While a single area of a sample can interact with more than one probe reagents, the nucleic acid label can be designed such that any known or potential overlaps could be teased apart from the signal output. In the case where any probe may potentially overlap with all others, one can use the readout-by-hybridization variation and assign each probe a single unique hybridization sequence. Such approach can avoid multiple lengthy probe incubations and damaging stripping steps.

In some embodiments of the methods described herein, the signal signatures produced during any readout step (e.g., sequencing-based or hybridization-based) should be removed before advancing to the next pre-determined subsequence of the detection reagents. The removal of the signal signatures can be done by any methods known in the art, including, but not limited to, washing, heating, photobleaching, displacement, cleavage, enzymatic digestion, quenching, chemical degradation, bleaching, oxidation, and any combinations thereof.

In some embodiments, the decoder probes can be designed such that they can be simply washed out either with a plain buffer, or they can be modified by varying salt concentrations or using detergents or denaturants such as formamide or dimethyl sulfoxide (DMSO).

In other embodiments, the fluorescence or color signature of a readout step can be attenuated or eliminated by photobleaching the signal using sufficient optical exposure. In alternative embodiments, the fluorescence or color signature of a readout step can be attenuated or eliminated by subjecting the fluorescence or color signature to chemical degradation under appropriate conditions, e.g., using a reducing agent or oxidizing solution such as 0.01 M sodium periodate.

In some embodiments, the decoder probes can be displaced from their hybridization sites by introducing other reagents or probe displacers that have stronger binding affinities to those same sites. This can be done, for example, by using nucleic acid sequences that are longer than and/or have better complementarity than the decoder probe sequences. For example, to create "better complementarity" of the probe displacers, in some embodiments, mismatches can be seeded in the hybridization region. In other embodiments, the hybridization region can be preceded and/or post-ceded with a "toe-hold" of around 3-8 bases (e.g., 6 bases). In such embodiments, the "better complementarity" of the probe displacer can be outside of the hybridization region, which can make the design of the hybridization regions easier.

In some embodiments, enzymes can be used to displace, digest, cut and/or cleave the detectable labels, the decoder probe sequence, the hybridized complex (formed by the decoder probe and pre-determined subsequence), and/or the cleavable sequence linker to the hybridized complex, in order to remove the signal signatures. One example is to introduce a deoxyuridine into the decoder probe. This modified base can be cleaved using the enzyme mix known as USER, thereby cutting the decoder probe sequence into two parts. Since each part is now shorter, it is characterized by a lower melting temperature and can melt off the hybridization sites of the detection reagents. Alternatively, one of skill in the art can employ one of numerous art-recognized sequence-specific nucleases or restriction enzymes, which can cut either the decoder probe sequence, the pre-determined subsequence that has been hybridized with decoder probes, the cleavable sequence linker attached to the hybridized subsequence and/or the hybridized complex thereof, thereby removing the signal signature.

In some embodiments, thermal denaturing can be used to remove the signal signature from a previous readout. In some embodiments where sequencing is involved, thermal denaturing can be reduced or avoided by using a sequencing-by-ligation approach and by setting the nucleic acid label base that immediately follows the sequencing primer (in the direction of ligation) to an adenine. Correspondingly, the ligation probes should then include a (deoxy-)uracil in the primer-proximal position. Without wishing to be bound by theory, an enzyme such as USER, which cleaves DNA at uracils can be used to remove the ligation probe and ready the system for the next sequencing step. These fragments will have lower melting temperatures than their parent probes, and these temperatures can be designed to fall below the operating temperature (or require an acceptable denaturing temperature).

After detection of the pre-determined subsequences is completed in a temporally-sequential manner, in some embodiments, the method described herein can further comprise comparing the temporal order of the signal signatures with different identifiers of said at least one probe reagent, wherein an agreement between the temporal order of the signal signatures and a particular identifier of said at least one probe reagent identifies the analyte in the sample. In some embodiments, the method can further comprise measuring the intensity of the signal signatures generated from each subpopulation of the detection reagents. In some embodiments, the intensity of the signal signatures generated from each subpopulation of the detection reagents can indicate an amount of the analyte. In some embodiments, the relative intensity of the signal signatures can be used in identification of each subpopulation of the detection reagents. Thus, the intensity of the signal signatures can be used as part of a coding scheme of the detection reagents described herein. The comparing and intensity measuring steps can be performed, e.g., by a computer-implemented software or algorithm.

Types of signal signature(s) can vary upon different embodiments of detection reagents and/or decoder probes described herein. As used herein, the term "signal signature" refers to a change in, or occurrence of, a response or indicator that is detectable either by observation or instrumentally. In certain instances, the signal signature is fluorescence or a change in fluorescence, e.g., a change in fluorescence intensity, fluorescence excitation or emission wavelength distribution, fluorescence lifetime, and/or fluorescence polarization. By way of example only, the fluorescence can be produced by binding a fluorophore to a decoder probe, and/or by detecting the hybridization using a fluorescent dye, e.g., SYBR Gold, that lights up when nucleic acid sequence becomes double-stranded. In certain other instances, the signal signature can be radioactivity (i.e., radiation), including alpha particles, beta particles, nucleons, electrons, positrons, neutrinos, and gamma rays emitted by a radioactive substance such as a radionuclide. By way of example, the detection reagents and/or decoder probes can comprise an optical molecule or label, thus producing optical signatures. Examples of optical signatures can include, without limitations, signatures of fluorescent color, visible light, no-color, and any combinations thereof. In such embodiments, the optical signatures can be detected by optical imaging or spectroscopy.

Detection Reagents (Or Detection Molecules as used Interchangeably Herein)

Another aspect provided herein is a detection reagent, which can be, for example, used in the methods described herein for any multiplexing assays. The detection reagent comprises at least one probe reagent and at least one nucleic acid label, wherein said at least one nucleic acid label comprises at least one pre-determined subsequence to be detected in a temporally-sequential manner; wherein said at least one pre-determined subsequence forms an identifier of said at least one probe reagent; and wherein said at least one probe reagent and said at least one nucleic acid label are conjugated together.

The detection reagents described herein can exist in different forms. By way of example only, in some embodiments, the detection reagent can be a detection molecule. In some embodiments, the detection reagent can be a detection particle. In some embodiments, the detection reagent can be multi-molecular.

As used herein, the term "conjugated" refers to two molecules being linked to each other, e.g., attaching a probe reagent to a nucleic acid label. The conjugation process can be performed, e.g., via a chemical reaction, or via a linker, which will be described later.

Depending on various applications and/or assay conditions (e.g., sensitivity, sample volume/concentration), a readout signal of a detection reagent can be amplified by increasing the number of the nucleic acid labels present in the detection reagent, e.g., by conjugating at least one probe reagent to a plurality of nucleic acid labels. In such embodiments, a plurality of the nucleic acid labels present in the detection reagent can range from about 2 to about 100,000, about 2 to about 10,000, about 2 to about 1,000, or about 2 to about 100. In some embodiments where the detection reagent comprises a particle as a hub, the number of possible nucleic acid labels present in the detection reagent can depend on the size of a particle. Generally, the larger the particle it is, the more nucleic acid labels can be incorporated into the detection reagent. For example, a particle of about 1-2 µm in size can allow incorporation of about 100,000 nucleic acid labels into the detection reagent. In some embodiments, there can be 2, 3, 4, 5, 6, 7, 8, 9, 10, 11, 12, 13, 14, 15, 16, 17, 18, 19, 20, 50, 100, 500, 1000, 5000, 10000, 50000, 100000 nucleic acid labels present in the detection reagent. One of skill in the art can determine the optimum number of nucleic acid labels present the detection reagent without any undue experimentation.

The detection reagents described herein can be used in any biological assays for detection, identification and/or quantification of target molecules or analytes, including counting marked cells such as bacteria or cancer cells, in a sample. By way of example only, in some embodiments, the detection reagent can be adapted for use in immunofluorescence. In alternative embodiments, the detection reagent can be adapted for use in immunohistochemistry. In other embodiments, the detection reagent can be adapted for use in fluorescence in situ hybridization. In some embodiments, the detection reagent can be adapted for use in western blot. Depending on the nature of the sample and/or applications, the detection reagent can be adapted to be in any format, e.g., immobilized on a solid support, or in a solution or suspension phase. In certain embodiments, the detection reagent can be adapted to be present in a solution or suspension phase. The phrase "in a solution or suspension phase" as used herein generally refers to suspending the detection reagents in a liquid fluid, e.g., an aqueous buffer solution. Additional applications of the detection reagents and/or methods described herein will be discussed.

Probe Reagents (Or Probe Molecules as used Interchangeably Herein)

Each of the detection reagents described herein can comprise any number of probe reagents. In some embodiments, the detection reagent can comprise one or more probe reagents, e.g., at least 1, at least 2, at least 3, at least 4, at least 5, at least 6, at least 7, at least 8, at least 9, at least 10 or more probe reagents. In one embodiment, the detection reagent can comprise one probe reagent. In other embodiments, the detection reagent can comprise a plurality of probe reagents, e.g., ranging from about 2 to about 100,000 probe reagents, about 2 to about 10,000 probe reagents, about 2 to about 1,000 probe reagents, or about 2 to about 100 probe reagents. In some embodiments where the detection reagent comprises a particle as a hub, the number of possible probe reagents present in the detection reagent can depend on the size of a particle. Generally, the larger the particle it is, the more probe reagents can be incorporated into the detection reagent. For example, a particle of about 1-2 µm in size can allow incorporation of about 100,000 probe reagents into the detection reagent. In some embodiments, there can be about 2, 3, 4, 5, 6, 7, 8, 9, 10, 11, 12, 13, 14, 15, 16, 17, 18, 19, 20, 50, 100, 500, 1000, 5000, 10000, 50000, 100000 probe reagents present in the detection reagent. One of skill in the art can determine the optimum number of probe reagents present the detection reagent without any undue experimentation.

As used interchangeably herein, the term "probe," "probe reagent" or "probe molecule" refers to an entity (e.g., but not limited to, a molecule, a particle, a composite entity, or a multi-molecular entity) that interacts with or binds to a target molecule or an analyte for the analysis of the target or the analyte. Typically the nature of the interaction or binding is noncovalent, e.g., by hydrogen, electrostatic, or van der Waals interactions, however, binding can also be covalent. Probe reagents can be entities (e.g., but not limited to, molecules, a particles, composite entities, or multi-molecular entities) capable of undergoing binding or molecular recognition events with target molecules. Probe reagents can be naturally-occurring, recombinant or synthetic. Examples of the probe reagent can include, but are not limited to, a nucleic acid, an antibody or a portion thereof, an antibody-like molecule, an enzyme, a cell, an antigen, a small molecule, a protein, a peptide, a peptidomimetic, an aptamer, and any combinations thereof. By way of example only, in immunohistochemistry, the probe reagent can include an antibody specific to the target antigen to be analyzed. An ordinary artisan can readily identify appropriate probe reagents for the target molecules or analytes of interest to be detected in various bioassays. In some embodiments, the probe reagent can be multi-molecular. For example, in one embodiment, the probe reagent can comprise a particle, an antibody, biotin and/or streptavidin, or any combinations thereof.

In some embodiments, the probe reagents can be modified by any means known to one of ordinary skill in the art. Methods to modify each type of probe reagents are well recognized in the art. Depending on the types of probe reagents, an exemplary modification includes, but is not limited to genetic modification, biotinylation, labeling (for detection purposes), chemical modification (e.g., to produce derivatives or fragments of the probe reagent), and any combinations thereof. In some embodiments, the probe reagent can be genetically modified. In some embodiments, the probe reagent can be biotinylated.

As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

As used herein, the term "peptidomimetic" refers to a molecule capable of folding into a defined three-dimensional structure similar to a natural peptide The term "nucleic acids" used herein refers to polymers (polynucleotides) or oligomers (oligonucleotides) of nucleotide or nucleoside monomers consisting of naturally occurring bases, sugars and intersugar linkages. The term "nucleic acid" also includes polymers or oligomers comprising non-naturally occurring monomers, or portions thereof, which function similarly. Exemplary nucleic acids include, but are not limited to, deoxyribonucleic acid (DNA), ribonucleic acid (RNA), locked nucleic acid (LNA), peptide nucleic acids (PNA), and polymers thereof in either single- or double-stranded form. Locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo conformation. LNA nucleotides can be mixed with DNA or RNA residues in the oligonucleotide whenever desired. Such LNA oligomers are generally synthesized chemically. Peptide nucleic acid (PNA) is an artificially synthesized polymer similar to DNA or RNA. DNA and RNA have a deoxyribose and ribose sugar backbone, respectively, whereas PNA's backbone is composed of repeating N-(2-aminoethyl)-glycine units linked by peptide bonds. PNA is generally synthesized chemically. Unless specifically limited, the term "nucleic acids" encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer, et al., Nucleic Acid Res. 19:5081 (1991); Ohtsuka, et al., J. Biol. Chem. 260:2605-2608 (1985), and Rossolini, et al., Mol. Cell. Probes 8:91-98 (1994)). The term "nucleic acid" should also be understood to include, as equivalents, derivatives, variants and analogs of either RNA or DNA made from nucleotide analogs, and, single (sense or antisense) and double-stranded polynucleotides.

In some embodiments, the term "nucleic acid" described herein can include a modified nucleic acid. Modified nucleic acids are well known in the art. Thus, a nucleic acid described herein can comprise one or more nucleic acid modifications known in the art. For example, the nucleic acid can comprise one or more nucleic acid modifications selected from the group consisting of internucleotide linkage modifications (intersugar linkage modifications), sugar modifications, nucleobase modifications, backbone modifications/replacements, and any combinations thereof. Exemplary internucleotide linkage modifications include, but are not limited to, phosphorothioate, phosphorodithioate, phosphotriester (e.g. alkyl phosphotriester), aminoalkylphosphotriester, alkyl-phosphonate (e.g., methyl-phosphonate), selenophosphate, phosphoramidate (e.g., N-alkylphosphoramidate), boranophosphonate, and the like. Exemplary sugar modifications include, but are not limited to, 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA), 2'-O—CH$_2$CH$_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), arabinose sugar, and the like. Exemplary nucleobase modifications include, but are not limited to, inosine, xanthine, hypoxanthine, nubularine, isoguanisine, tubercidine, 5-methylcytosine (5-me-C); 5-hydroxymethyl cytosine; xanthine; hypoxanthine; 2-aminoadenine; 6-methyl and other 6-alkyl derivatives of adenine and guanine; 2-propyl and other 2-alkyl derivatives of adenine and guanine; 2-thiouracil; 2-thiothymine; 2-thiocytosine; 5-propynyl uracil; 5-propynyl cytosine; 6-azouracil; 6-azocytosine; 6-azothymine; 5-uracil (pseudouracil); 4-thiouracil; 8-halo, 8-amino, 8-thiol, 8-thioalkyl, 8-hydroxyl and other 8-substituted adenines and guanines; 5-halo particularly 5-bromo, 5-trifluoromethyl and other 5-substituted uracils and cytosines; 7-methyl and other 7-alkyl derivatives of adenine and guanine; 8-azaguanine; 8-azaadenine; 7-deazaguanine; 7-deazaadenine; 3-deazaguanine; 3-deazaadenin; universal base; and any combinations thereof. Exemplary backbone modifications include, but are not limited to, morpholino, cyclobutyl, pyrrolidine, peptide nucleic acid (PNA), aminoethylglycyl PNA (aegPNA), backnone-extended pyrrolidine PNA (bepPNA), and the like.

The term "enzymes" as used here refers to a protein molecule that catalyzes chemical reactions of other substances without it being destroyed or substantially altered upon completion of the reactions. The term can include naturally occurring enzymes and bioengineered enzymes or mixtures thereof. Examples of enzyme families include kinases, dehydrogenases, oxidoreductases, GTPases, carboxyl transferases, acyl transferases, decarboxylases, transaminases, racemases, methyl transferases, formyl transferases, and α-ketodecarboxylases.

As used herein, the term "aptamers" means a single-stranded, partially single-stranded, partially double-stranded or double-stranded nucleotide sequence capable of specifically recognizing a selected non-oligonucleotide molecule or group of molecules. In some embodiments, the aptamer recognizes the non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and non-nucleotide residues, groups or bridges. Methods for selecting aptamers for binding to a molecule are widely known in the art and easily accessible to one of ordinary skill in the art.

As used herein, the term "antibody" or "antibodies" refers to an intact immunoglobulin or to a monoclonal or polyclonal antigen-binding fragment with the Fc (crystallizable fragment) region or FcRn binding fragment of the Fc region. The term "antibodies" also includes "antibody-like molecules", such as fragments of the antibodies, e.g., antigen-binding fragments. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies, and polypeptides that contain at least a portion of an immunoglobulin that is sufficient to confer specific antigen binding to the polypeptide. Linear antibodies are also included for the purposes described herein. The terms Fab, Fc, pFc', F(ab') 2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop.

The expression "linear antibodies" refers to the antibodies described in Zapata et al., Protein Eng., 8(10):1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The expression "single-chain Fv" or "scFv" antibody fragments, as used herein, is intended to mean antibody fragments that comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. (Plückthun, The Pharmacology of Monoclonal Antibodies, vol. 113, Rosenburg and Moore eds., Springer-Verlag, New York, pp. 269-315 (1994)).

The term "diabodies," as used herein, refers to small antibody fragments with two antigen-binding sites, which fragments comprise a heavy-chain variable domain (VH) Connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. (EP 404,097; WO 93/11161; Hollinger et ah, Proc. Natl. Acad. Sd. USA, P0:6444-6448 (1993)).

As used herein, the term "small molecules" refers to natural or synthetic molecules including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "cells" used herein refers to any cell, prokaryotic or eukaryotic, including plant, yeast, worm, insect and mammalian. Mammalian cells include, without limitation; primate, human and a cell from any animal of interest, including without limitation; mouse, hamster, rabbit, dog, cat, domestic animals, such as equine, bovine, murine, ovine, canine, feline, etc. The cells may be a wide variety of tissue types without limitation such as; hematopoietic, neural, mesenchymal, cutaneous, mucosal, stromal, muscle spleen, reticuloendothelial, epithelial, endothelial, hepatic, kidney, gastrointestinal, pulmonary, T-cells etc. Stem cells, embryonic stem (ES) cells, ES-derived cells and stem cell progenitors are also included, including without limitation, hematopoeitic, neural, stromal, muscle, cardiovascular, hepatic, pulmonary, gastrointestinal stem cells, etc. Yeast cells may also be used as cells in some embodiments of the methods described herein. In some embodiments, the cells can be ex vivo or cultured cells, e.g. in vitro. For example, for ex vivo cells, cells can be obtained from a subject, where the subject is healthy and/or affected with a disease. Cells can be obtained, as a non-limiting example, by biopsy or other surgical means know to those skilled in the art.

As used herein, the term "antigens" refers to a molecule or a portion of a molecule capable of being bound by a selective binding agent, such as an antibody, and additionally capable of being used in an animal to elicit the production of antibodies capable of binding to an epitope of that antigen. An antigen may have one or more epitopes. The term "antigen" can also refer to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

In some embodiments, the probe reagent can be an antibody or a portion thereof, or an antibody-like molecule. In such embodiments, the probe reagents can be used to, for example, detect and/or identify pathogen type or species, the presence of cell or disease markers, cellular protein expression levels, phosphorylation or other post-translation modification state, or any combinations thereof. By way of example only, FIG. 3 shows three different embodiments of the detection reagents comprising at least one (e.g., 1, 2, 3, 4, 5 or more) pathogen-specific antibodies (e.g., anti-*E. coli*, anti-*S. aureus*, and anti-*C. albicans*).

In some embodiments, the probe reagent can be a nucleic acid (e.g., DNA, RNA, LNA, PNA, or any combinations thereof). In such embodiments, the nucleic acids can be used to determine, for example, the existence of characteristic cellular DNA or RNA sequences (such as in fluorescent in situ hybridization), RNA expression levels, miRNA presence and expression, and any combinations thereof, in various applications, e.g., for pathogen detection and/or identification.

In some embodiments, the probe reagent can be a protein or a peptide. In such embodiments, the protein or peptide can be essentially any proteins with known binding targets. Examples include, but are not limited to, innate-immune proteins (e.g., without limitations, MBL, Dectin-1, TLR2, and TLR4 and any proteins disclosed in U.S. Provisional Application No. 61/508,957, the content of which is incorporated herein by reference in its entirety) and proteins comprising the chitin-binding domain. Such innate-immune proteins and chitin-binding domain proteins can be used to detect their corresponding pattern-recognition targets (e.g., microbes such as bacteria) and fungus, respectively. By way of example only, instead of using pathogen-specific antibodies as probe reagents in the detection reagents as shown in FIG. 3, innate-immune proteins (e.g., MBL) or chitin-binding domain proteins can be used as probe reagents for detection of pathogens. While such detection reagents can be used to detect pathogens, they may not be pathogen-specific, as compared to the ones using pathogen-specific antibodies as probes molecules.

In some embodiments, the probe reagent can be an aptamer. In some embodiments, the probe reagent can be a DNA or RNA aptamer. The aptamers can be used in various bioassays, e.g., in the same way as antibodies or nucleic acids described herein. By way of example only, FIG. 4 shows some exemplary embodiments of the detection reagents comprising at least one (e.g., 1, 2, 3, 4, 5 or more) DNA aptamers (e.g., with a nucleotide sequence complementary to nuclear reprogramming factors, such as Oct4, Sox2, and Klf4). Such detection reagents can be used to determine RNA expression level of nuclear reprogramming factors in somatic cells for detecting, screening, or identifying stem cells (e.g., induced pluripotency stem cells).

In some embodiments, the probe reagent can be a cell surface receptor ligand. As used herein, a "cell surface receptor ligand" refers to a molecule that can bind to the outer surface of a cell. Exemplary, cell surface receptor ligand includes, for example, a cell surface receptor binding peptide, a cell surface receptor binding glycopeptide, a cell surface receptor binding protein, a cell surface receptor binding glycoprotein, a cell surface receptor binding organic compound, and a cell surface receptor binding drug. Additional cell surface receptor ligands include, but are not limited to, cytokines, growth factors, hormones, antibodies, and angiogenic factors.

When the detection reagents described herein are used as targeted delivery vehicles, e.g., for a diagnostic agent, in some embodiments, the probe reagent can be an endosomolytic ligand. As used herein, the term "endosomolytic ligand" refers to molecules having endosomolytic properties. Endosomolytic ligands can promote the lysis of and/or transport of the composition described herein, or its components, from the cellular compartments such as the endosome, lysosome, endoplasmic reticulum (ER), Golgi apparatus, microtubule, peroxisome, or other vesicular bodies within the cell, to the cytoplasm of the cell. Some exemplary endosomolytic ligands include, but are not limited to, imidazoles, poly or oligoimidazoles, linear or branched polyethyleneimines (PEIs), linear and branched polyamines, e.g. spermine, cationic linear and branched polyamines, polycarboxylates, polycations, masked oligo or poly cations or anions, acetals, polyacetals, ketals/polyketals, orthoesters, linear or branched polymers with masked or unmasked cationic or anionic charges, dendrimers with masked or unmasked cationic or anionic charges, polyanionic peptides, polyanionic peptidomimetics, pH-sensitive peptides, natural and synthetic fusogenic lipids, natural and synthetic cationic lipids.

In other embodiments, the probe reagent for use in delivery of an agent (e.g., a diagnostic agent) encapsulated within the detection reagents described herein can be a PK modulating ligand. As used herein, the terms "PK modulating ligand" and "PK modulator" refers to molecules which can modulate the pharmacokinetics of the composition described herein. Some exemplary PK modulator include, but are not limited to, lipophilic molecules, bile acids, sterols, phospholipid analogues, peptides, protein binding agents, vitamins, fatty acids, phenoxazine, aspirin, naproxen, ibuprofen, suprofen, ketoprofen, (S)-(+)-pranoprofen, carprofen, PEGs, biotin, and transthyretia-binding ligands (e.g., tetraiidothyroacetic acid, 2,4,6-triiodophenol and flufenamic acid).

In various embodiments, the detection reagent described herein can comprise one kind/species of probe reagents or different kinds/species of probe reagents. In some embodiments, the kind/species of the probe reagents present in the detection reagent can be the same. In other embodiments, the detection reagent can include at least one different kind/species of the probe reagents (e.g., 1, 2, 3, 4, 5, or 6 probe reagent species). In such embodiments, the distinct probe reagent species can be different from the others by types (e.g., antibodies vs. DNA aptamers), binding domains, and/or target analytes.

Nucleic Acid Labels

In accordance with embodiments of various aspects described herein, the nucleic acid label or nucleic acid tag comprises at least one pre-determined nucleic acid subsequence, which is used to identify an analyte or target. In some embodiments, the nucleic acid label or nucleic acid tag can comprise any number of the pre-determined nucleic acid subsequences, e.g., ranging from about 1 to about 100, from about 2 to about 80, or from about 3 to about 50. In some embodiments, the nucleic acid label or nucleic acid tag can comprise at least about 1, at least about 2, at least about 3, at least about 4, at least about 5, at least about 6, at least about 7, at least about 8, at least about 9, at least about 10, at least about 15, at least about 20, at least about 30, at least about 40, at least about 50, at least about 60, at least about 70 or more pre-determined nucleic acid subsequences. In some embodiments, the nucleic acid label or nucleic acid tag can comprise 1, 2, 3, 4, 5, 6, 7, 8, 9, 10, 15, 20, 30, 40, 50, 60, 70 or more pre-determined nucleic acid subsequences. Without wishing to be bound, the minimum number of pre-determined nucleic acid subsequences (n) required in the detection reagent can vary upon the number of distinct probes to be detected (X) and/or the number of distinct detectable labels (e.g., optical labels such as fluorescent labels or quantum dots) available to be used (Y), and n can be determined by the equation:

$$n = \text{ceiling}\left(\frac{\ln X}{\ln Y}\right),$$

where the mathematical function "ceiling" refers to rounding up a non-integer number to the nearest integer, when needed. For example, if 4 distinct detectable labels (Y) are used to distinguish 62 distinct probe reagents (X), n=ceiling (2.98)~3. Therefore, at least three pre-determined nucleic acid subsequences are required in this example.

In some embodiments where the detectable labels include no-color (dark), the number of distinct detectable label available to be used can become Y+1. In such embodiments, n can be determined by the equation:

$$n = \text{ceiling}\left(\frac{\ln X}{\ln (Y+1)}\right),$$

and thus fewer pre-determined nucleic acid subsequences can be used. However, the combination in which all readout cycles are dark should not be allowed.

Further, the pre-determined nucleic acid subsequences can be designed such that each readout cycle can light up in multiple colors. Thus, $2^Y$ instead of Y is used in the equation for n above and fewer pre-determined nucleic acid subsequences can thus be required. However, the combination in which all readout cycles are dark should not be allowed.

Additionally, while colors are generally used in a binary fashion, i.e., whether the color is present or not, in the above examples, the color intensity can also be used as a parameter of a signal signature. For example, if one detectable label is allowed to light up twice as brightly in a different color than another, the multiplexing capacity can be even further expanded.

The pre-determined nucleic acid subsequences can be constructed from any types of nucleic acids, including, but not limited to, DNA, RNA, PNA, LNA and any combinations thereof.

Each of the pre-determined subsequences of the nucleic acid label can be independently of any length. In certain embodiments, the pre-determined subsequences can each independently comprise a length of about 1 nucleobase to about 100 nucleobases, from about 1 nucleobase to about 50 nucleobases, from about 2 nucleobases to about 50 nucleobases, from about 5 nucleobases to about 30 nucleobases, or from about 5 nucleobases to about 20 nucleobases. In some embodiments, the pre-determined subsequences can each independently comprise one or more nucleobases, e.g., 1, 2, 3, 4, 5, 6, 7, 8, 9, 10, 11, 12, 13, 14, 15, 16, 17, 18, 19, 20 or more nucleobases.

The achievable length of the pre-determined subsequences can affect the degree of multiplexibility. In some embodiments, the achievable length of the pre-determined subsequences can be a function of the decreasing fluorescence intensity over many cycles of stripped and rehybridization (i.e. diffusion of the sequenceable particles, degradation, increasing background noise). In the case of DNA or RNA based nucleic acid labels that are amplified in situ, modified base is incorporated during its synthesis (i.e., dUTP, biotin, Acrydite, aminoallele), enabling these detection reagents to be permanently embedded in a film (regardless of the film thickness) of functionalized polyacrylamide (i.e. Acrydite streptavidin, NHS ester Acrydite). The embedded material can then be stripped and rehybridized for many more cycles without altering its spatial architecture and minimizing the background noise.

Two or more pre-determined subsequences can be conjugated together within a nucleic acid label using any methods known in the art. In some embodiments, two or more pre-determined subsequences can be conjugated together by a sequence linker. The term "sequence linker" as used herein generally refers to an entity that connects two sequences or subsequences as described herein together.

In some embodiments, the sequence linker can be a direct bond or an atom such as nitrogen, oxygen or sulfur; a unit such as $NR_1$, $C(O)$, $C(O)NH$, $SO$, $SO_2$, $SO_2NH$; or a chain of atoms. If needed, the two ends of the pre-determined subsequences can be linked together by providing on the two ends of the pre-determined subsequences complementary chemical functionalities that undergo a coupling reaction. In particular embodiments, the sequence linker is a direct bond, including, but not limited to, a phosphodiester bond. For example, a 3' carbon atom of a sugar base at the 5' end nucleotide of a first pre-determined subsequence can interact with the 5' carbon atom of another sugar base at the 3' end nucleotide of a second pre-determined subsequence to form a covalent bond, e.g., a phosphodiester bond. As such, two or more pre-determined subsequences can be bonded together to form a longer and contiguous pre-determined subsequence.

In some embodiments, the sequence linker can be a nucleotidic linker. The term "nucleotidic linker" as used herein refers to a linker of one nucleotide long or a sequence substantially comprising a plurality of nucleotides. In some embodiments, the nucleotidic linker can have a sequence length of at least 1, at least 2, at least 3, at least 4, at least 5, at least 6, at least 7, at least 8, at least 9, at least 10, at least 15, at least 20, at least 30 or more nucleotides. The sequence length of the nucleotidic linker can vary with a number of factors, e.g., detection methods, and/or properties of optical labels. Without wishing to be bound by theory, in some embodiments, increasing the length of the nucleotidic linker can increase the flexibility of the nucleic acid label, e.g., to increase the binding frequency between a pre-determined sequence and a decoder probe, the term of which will be discussed later. However, too long a nucleotidic linker can result in a too long nucleic acid label, which could overlap with other nucleic acid labels of the detection reagents during an assay and thus reduce the quality and/or accuracy of the signal detection. One of skill in the art can determine the optimum length of the nucleotidic linker without undue experimentations.

The nucleotidic linker can be in any structure or conformation. In some embodiments, the nucleotidic linker can be in a structure selected from the group consisting of single-stranded, double-stranded, partially double-stranded, a hairpin, or any combinations thereof.

In some embodiments, the sequence linker can be a bead or a nanoparticle acting as a hub. Accordingly, two or more pre-determined subsequences can be independently conjugated together via a bead or a nanoparticle.

Without wishing to be bound, while the sequence linker can be a direct bond, an atom, a nucleotidic linker, or any combinations thereof, the sequence linker can also include a sequence of amino acids, a polymer chain, a microbead, a nanobead, or any combinations thereof. To provide for the linkages between sequence linker, in some embodiments, different functionalities can be introduced to the ends of sequence linker and/or the pre-determined subsequences. Examples of functionalities include, but are not limited to, amide groups, including carbonic acid derivatives, ethers, esters, including organic and inorganic esters, amino, urethane, urea and any combinations thereof.

In some embodiments, the nucleic acid label is substantially a polynucleotide sequence containing one or more pre-determined subsequences. In such embodiments, any two pre-determined subsequences are either joined or conjugated together by a direct bond such as a phosphodiester bond (to produce longer contiguous subsequence), a nucleotidic linker of any desirable length, or any combinations thereof.

In such embodiments, the nucleic acid label of the detection reagent can be adapted to any configuration or structure. In some embodiments, the nucleic acid label can be single-stranded, double-stranded, partially double-stranded, a hairpin, linear, circular, branched, a concatemer, or any combinations thereof. In some embodiments, the nucleic acid label can be a linear polynucleotide sequence.

In some embodiments, the nucleic acid label can be a circular polynucleotide sequence. The advantage of using a circular nucleic acid label is that it can be amplified using rolling-circle amplification or hyperbranched rolling-circle amplification to generate a long continuous nucleic acid molecule that contains multiple copies of the same nucleic acid label sequences linked in series (also known as concatemer), thus resulting in an amplified signal. In some embodiments, instead of pre-forming the detection reagents comprising the circular nucleic acid label(s) and the probe reagent(s), detection reagents comprising linear polynucleotide(s) and the probe reagent(s) can be first synthesized. The circular nucleic acid labels can then added to hybridize with the linear polynucleotide(s) before or after the probe reagent(s) bind to the analytes. In such embodiments, while requiring an extra step, this approach can have the advantage over direct attachment of circular nucleic acid labels in that it does not require chemical modification of the nucleic acid label for conjugation with the probe reagents, thus resulting in a circular nucleic acid label that is compatible with a broader range of amplification enzymes. Furthermore, the linear polynucleotides can be smaller than the secondary circular nucleic acid labels, facilitating diffusion of the probe reagents (and the detection reagents) to their targets. In other embodiments, the linear polynucleotides can be circularized using a suitable double-stranded or single-stranded ligase, with or without the addition of a suitable ligation template. Without wishing to be bound by theory, such embodiments can avoid the extra hybridization that is required when a pre-circularized oligonucleotide is used instead.

When the detection reagents described herein are used as FISH probes, the nucleic acid labels and the FISH probes can be part of the same nucleic acid sequence construct, and thus the circularization can encompass the entire construct (e.g., both the nucleic acid labels and FISH probes). A schematic representation of exemplary FISH probes for SeqTagged FISH is shown in FIG. 15.

In some embodiments, the method described herein can be used to identify a class an analyte, e.g., a pathogen belongs to. For example, the method can be used to identify if a pathogen is a Gram-negative, Gram-positive, or some other class of pathogen, e.g., yeast. Thus, the method described herein can be used to as Gram test to determine whether a suspected pathogen is Gram positive, Gram negative or yeast. This can be useful for quickly identifying the type of infection in a subject and administering appropriate therapy. By way of example only, this can be accomplished using a detection reagent comprising a class-specific probe, also referred to as "Gram-stain like probe" herein. Again by way of example only, the probe can be a DNA probe for FISH.

In some embodiment, the FISH probe for identifying eubacteria can comprise the nucleotide sequence of SEQ ID NO: 4 (GCTGCCTCCCGTAGGAGT). An exemplary SeqTag labeled FISH-probe for identifying eubacteria can comprise the nucleotide sequence of SEQ ID NO: 5 (CTGCCTCCCGTAGGAGTTTTTTCGCTT-TAGCCTAAGTGAAATC).

In some embodiments, the FISH probe for identifying yeast can comprise the nucleotide sequence of SEQ ID NO: 6 (CTCTGGCTTCACCCTATTC. An exemplary SeqTag labeled FISH-probe for identifying yeast can comprise the nucleotide sequence of SEQ ID NO: 7 (CTCTGGCTT-CACCCTATTCTTTTTCGCTTTTTTGGGGAAAA-GACA).

In some embodiments, the FISH probe for identifying firmicutes can comprise the nucleotide sequence of SEQ ID NO: 8 (CGGAAGATTCCCTACTGC). An exemplary SeqTag labeled FISH-probe for identifying yeast can comprise the nucleotide sequence of SEQ ID NO: 9 (CGGAA-GATTCCCTACTGCTTTTTCGCTTTCTGTAATG-GAGTGGA).

In the SeqTag labeled FISH probes discussed above, each probe can be assigned a particular "signal signature" for each of the three readout steps. For example, colors can be labeled at B, C, and D. In some embodiments, each color can be from a different fluorophore, such as FAM, Cy3 and Cy5. Each signal signature can take advantage of multiple fluorophores simultaneously or even the same fluorophore multiple times, e.g., a SeqTag with signal signature corresponding to "DDDC."

An exemplary signal signature for identifying eubacteria, yeast or firmicutes is shown in Table 1. As shown, each class has a different assigned code for the first readout step. For example, for the first readout, eubacteria are assigned color C' yeast color D and firmicutes color B. On readout, eubacteria will show up as color C, yeast as color D, firmicutes as both colors B and C.

TABLE 1

| Name | Assigned code | | | Effective code | | |
|---|---|---|---|---|---|---|
|  | S1 | S2 | S3 | S1 | S2 | S3 |
| Eubacteria-Kempf | C | | | C | | |

TABLE 1-continued

| Name | Assigned code | | | Effective code | | |
|---|---|---|---|---|---|---|
|  | S1 | S2 | S3 | S1 | S2 | S3 |
| All_yeast-Kempf | D | | | D | | |
| Firmicutes-pB-00196 | B | | | BC | | |

After identifying the class of pathogens, the pathogens can be further probed for identifying the specific pathogen or genus using the method described herein. For example, the detection reagent can comprise a pathogen specific probe that binds to a specific pathogen or genus of pathogens. For example, the probe can be a FISH probe that specifically binds to a specific pathogen. Some exemplary pathogen specific FISH probes are shown in Table 2.

TABLE 2

| SEQ ID NO: | Name | probeBase FISH Sequence | Assigned code | Effective code |
|---|---|---|---|---|
| | | Gram+ | | |
| 10 | Staph_spp-Kempf | TCCTCCATATCTCTGCGC | DD B | BC DD B |
| 11 | S_Aureus-Kempf | GAAGCAAGCTTCTCGTCCG | CD B | BC CDDD BB |
| 12 | Streptococcus_spp-Kempf | CACTCTCCCCTTCTGCAC | DD D | BC DD D |
| 13 | S_Pneumoniae-Kempf | GTGATGCAAGTGCACCTT | B DC | BC DDB DDC |
| 14 | S_Pyogenes-Kempf | TTCCAAAGCGTACATTGGTT | C DB | BC DDC DDB |
| 15 | S_Agalactiae-Kempf | GTAAACACCAAACMTCAGCG | D DC | BC DDD DDC |
| 16 | B_subtilis-pB-00401 | CGA AGG GGA CGT CCT ATC T | C DD | BC C DD |
| 17 | L_acidophilus-pB-00711 | CAG GCT TGC TCC TCG TTG | DD C | BC DD C |
| | | Gram- | | |
| 18 | P_Aeruginosa-Kempf | TCTCGGCCTTGAAACCCC | B B | C B B |
| 19 | K_Pneumoniae-Kempf | CCTACACACCAGCGTGCC | B DD | C B DD |
| 20 | H_influenzae-pB-00348 | CCG CAC TTT CAT CTT CCG | B BC | C B BC |
| 21 | B_cepacia-pB-00346 | CTG TGC GCC GGT TCT CTT | DD B | C DD B |
| 22 | K_oxytoca-pB-01681 | CTA CAA GAC TCC AGC CTG CC | DD C | C DD C |
| 23 | E_coli-pB-02569-compl | ATG AGC AAA GGT ATT AAC TTT ACT CCC | B C | C B C |
| 24 | Shewanella_spp-pB-01191-mod | AGC TAA TCC CAC CTA GGT TCA TC | BC B | C BC B |
| 25 | H_pylori-pB-00361 | CACACCTGACTGACTATCCCG | C B | C C B |
| | | Yeast | | |

TABLE 2-continued

| SEQ ID NO: | Name | probeBase FISH Sequence | Assigned code | Effective code |
|---|---|---|---|---|
| 26 | C_Albicans-Kempf | GCCAAGGCTTATACTCGCT | C BC | D C BC |
| 27 | C_Glabrata_Kempf | CCGCCAAGCCACAAGGACT | C CD | D C CD |
| 28 | C_Krusei-Kempf | GATTCTCGGCCCCATGGG | BC C | D BC C |
| 29 | C_Parapsflosis-Kempf | CCTGGTTCGCCAAAAGGC | CD C | D CD C |

Exemplary SeqTag labeled FISH-probe for identifying a specific pathogen are shown in Table 3. As shown in Table 3, each specific pathogen can be assigned a specific signal signature based on an assigned color for each readout step and identity of a pathogen can be decoded using this table when the method is carried out using this set of assigned coding.

TABLE 3

| SEQ ID NO: | Name | SeqTag-labeled FISH-probe Sequence |
|---|---|---|
| | | Gram+ |
| 30 | Staph_spp-Kempf | TCCTCCATATCTCTGCGCTTTTTCGCTTTCTGGAGAAAGGGCCATTTTTCGCTTTCGGTTCCAAAGACACTTTTTCGCTTTCTGGAGAAAGGGCCA |
| 31 | S_Aureus-Kempf | GAAGCAAGCTTCTCGTCCGTTTTTCGCTTTCTGGAGAAAGGGCCATTTTTCGCTTTCGGTTCCAAAGACACTTTTTCGCTTTGGAAGCACCTATTCC |
| 32 | Streptococcus_spp-Kempf | CACTCTCCCCTTCTGCACTTTTTCGCTTTCTGGAGAAAGGGCCATTTTTCGCTTTTCACGATCCCATGTATTTTTCGCTTTCTGGAGAAAGGGCCA |
| 33 | S_Pneumoniae-Kempf | GTGATGCAAGTGCACCTTTTTTCGCTTTGAAGCCGGTTATAGCTTTTTCGCTTTTAGGCATTAGCATTGTTTTTCGCTTTTCACGATCCCATGTA |
| 34 | S_Pyogenes-Kempf | TTCCAAAGCGTACATTGGTTTTTTCGCTTTCGGTTCCAAAGACACTTTTTCGCTTTGGAAGCACCTATTCCTTTTTCGCTTTTCACGATCCCATGTA |
| 35 | S_Agalactiae-Kempf | GTAAACACCAAACMTCAGCGTTTTTCGCTTTGAAGCCGGTTATAGCTTTTTCGCTTTCTGGAGAAAGGGCCATTTTTCGCTTTTCACGATCCCATGTA |
| 36 | B_subtilis-pB-00401 | CGA AGG GGA CGT CCT ATC TTTTTTCGCTTTTCACGATCCCATGTATTTTTCGCTTTGGAAGCACCTATTCCTTTTTCGCTTTTCACGATCCCATGTA |
| 37 | L_acidophilus-pB-00711 | CAG GCT TGC TCC TCG TTGTTTTTCGCTTTCTGGAGAAAGGGCCATTTTTCGCTTTGAAGCCGGTTATAGCTTTTTCGCTTTCTGGAGAAAGGGCCA |
| | | Gram- |
| 38 | P_Aeruginosa-Kempf | TCTCGGCCTTGAAACCCTTTTTCGCTTTTAGGCATTAGCATTGTTTTTCGCTTTCGGTTCCAAAGACAC |
| 39 | K_Pneumoniae-Kempf | CCTACACACCAGCGTGCCTTTTTCGCTTTTCACGATCCCATGTATTTTTCGCTTTTAGGCATTAGCATTGTTTTTCGCTTTTCACGATCCCATGTA |
| 40 | H_influenzae-pB-00348 | CCG CAC TTT CAT CTT CCGTTTTTCGCTTTCGGTTCCAAAGACACTTTTTCGCTTTTAGGCATTAGCATTGTTTTTCGCTTTGAAGCCGGTTATAGC |
| 41 | B_cepacia-pB-00346 | CTG TGC GCC GGT TCT CTTTTTTCGCTTTCTGGAGAAAGGGCCATTTTTCGCTTTCGGTTCCAAAGACACTTTTTCGCTTTCTGGAGAAAGGGCCA |
| 42 | K_oxytoca-pB-01681 | CTA CAA GAC TCC AGC CTG CCTTTTTCGCTTTCTGGAGAAAGGGCCATTTTTCGCTTTGAAGCCGGTTATAGCTTTTTCGCTTTCTGGAGAAAGGGCCA |

TABLE 3-continued

| SEQ ID NO: | Name | SeqTag-labeled FISH-probe Sequence |
|---|---|---|
| 43 | E_coli-pB-02569-compl | ATG AGC AAA GGT ATT AAC TTT ACT CCCTTTTTCGCTTTTAGGCATTAGCATTGTTTTTCGCTTTGAAGCCGG TTATAGC |
| 44 | Shewanella_spp-pB-01191-mod | AGC TAA TCC CAC CTA GGT TCA TCTTTTTCGCTTTTAGGCATTAGCATTGTTTTTCGCTTTCGGTTCCAA AGACACTTTTTCGCTTTGGAAGCACCTATTCC |
| 45 | H_pylori-pB-00361 | CACACCTGACTGACTATCCCGTTTTTCGCTTTGGAAGCACCTATTCC TTTTTCGCTTTCGGTTCCAAAGACAC |
| Yeast | | |
| 46 | C_Albicans-Kempf | GCCAAGGCTTATACTCGCTTTTTTCGCTTTCGGTTCCAAAGACACTT TTTCGCTTTGGAAGCACCTATTCCTTTTTCGCTTTGAAGCCGGTTATA GC |
| 47 | C_Glabrata_Kempf | CCGCCAAGCCACAAGGACTTTTTCGCTTTGAAGCCGGTTATAGCTT TTTCGCTTTGGAAGCACCTATTCCTTTTTCGCTTTTCACGATCCCATG TA |
| 48 | C_Krusei-Kempf | GATTCTCGGCCCCATGGGTTTTTCGCTTTTAGGCATTAGCATTGTTTT TCGCTTTGAAGCCGGTTATAGCTTTTTCGCTTTGGAAGCACCTATTC C |
| 49 | C_Parapsilosis-Kempf | CCTGGTTCGCCAAAAAGGCTTTTTCGCTTTCTGGAGAAAGGGCCATT TTTCGCTTTGAAGCCGGTTATAGCTTTTTCGCTTTGGAAGCACCTAT TCC |

As shown in Table 3, the "signal signature" can comprise multiple fluorescence "colors" in each step. For example, E. coli can be marked as red in step 1 and red+green in step 2 and blue in step 3. The "signal signature" can also be encoded in the brightness of the color at each step. For example, E. coli could be marked as red in step 1 and 3 times brighter red in step 2.

Exemplary hybridization sites for generating the different signal signatures at different steps using the exemplary SeqTag labeled FISH-probes described above are shown in Table 4.

TABLE 4

| SEQ ID NO. | Assigned "Color" | |
|---|---|---|
| Set 1 | | |
| 50 | B | CGCTTTCTGTAATGGAGTGGA |
| 51 | C | CGCTTTAGCCTAAGTGAAATC |
| 52 | D | CGCTTTTTTGGGGAAAAGACA |
| Set 2 | | |
| 53 | B | CGCTTTTAGGCATTAGCATTG |
| 54 | C | CGCTTTGGAAGCACCTATTCC |
| 55 | D | CGCTTTCTGGAGAAAGGGCCA |
| Set 3 | | |
| 56 | B | CGCTTTCGGTTCCAAAGACAC |
| 57 | C | CGCTTTGAAGCCGGTTATAGC |
| 58 | D | CGCTTTTCACGATCCCATGTA |

In some embodiments, multiple detection reagents can be used to identify a specific analyte. For example, a first set of probes can be used to identify whether the potential pathogen is gram-position, gram-negative and then another set of probes to identify it more specifically. Both probes would need to produce a detectable signal, allowing one to use, for example, Table 3 to uniquely identify the pathogen.

In some embodiments, the nucleic acid label can be a concatemer, including a colony or a DNA nanoball that is large enough to act as a particle rather than simply a strand of nucleic acid. Using a concatemer as a nucleic acid label can eliminate the need for in-situ enzymatic treatment of circular nucleic acid amplification, but it can also increase the overall molecular weight of the detection reagent and thus retard diffusion. Similar to the circular nucleic acid labels as described above, an exemplary approach of hybridizing concatemers with the linear polypeptides of the detection reagents after probe reagents bind to the analytes can be used to facilitate diffusion of the probe reagents (and the detection reagents) to their targets.

To increase the accuracy and/or specificity of the methods described herein, in various embodiments, the nucleic acid label can be designed for minimal cross-hybridization of bases with each other. Various art-recognized computational programs or algorithms are available to design nucleic acid sequences with minimal cross-hybridization. Thus, one of skill in the art can optimize the nucleic acid label sequence using any methods or algorithms known in the art.

In some embodiments, the nucleic acid labels described herein can be synthetic nucleic acid molecules (e.g., DNA, RNA, or DNA/RNA hybrids), and can be rationally-designed to have features that optimize labeling and detection of the detection reagents, and that prevent secondary structure formation. In some embodiments, a nucleic acid label is a designed polynucleotide sequence from about 50 to 50,000 bases long.

In some embodiments, the nucleic acid labels described herein can be designed to minimize predictable secondary structures, and/or be designed such that each nucleic acid label can hybridize only against its own target. In some embodiments, the nucleic acid labels described herein can be designed to be devoid of any secondary structure. Putative secondary structures (e.g. hairpins, folding, or internal base pairing) can be predicted by methods known in the art such as MFOLD. Without intending to be limited to any theory, in some embodiments, predictable secondary structure in the nucleic acid label can be minimized by avoiding inverted repeats and by skewing the backbone-specific content such that the backbone of the nucleic acid label is CT or GA-rich. Any art-recognized methods, e.g., MFOLD, can be used to verify if each nucleic acid label can hybridize only against its own target.

Sequences can also be screened to avoid common six-base-cutter restriction enzyme recognition sites. Selected sequences can be additionally subjected to predicted secondary structure analysis, and those with the least secondary structure may be chosen for further evaluation. Any program known in the art can be used to predict secondary structure, such as the MFOLD program (Zuker, 2003, Nucleic Acids Res. 31 (13):3406-15; Mathews et al., 1999, J. Mol. Biol. 288:911-940).

In some embodiments, the nucleic acid label can comprise only a subset of the A, G, C, T (and/or U) nucleotides or modified nucleotides thereof. In some embodiments, the nucleic acid label can comprise only one of the A, G, C, T (and/or U) nucleotides or modified nucleotides thereof. In some embodiments, the nucleic acid can comprise two of the A, C, T (and/or U) nucleotides or modified nucleotides thereof. In some embodiments, the nucleic acid label can comprise only three of the A, G, C, and T (and/or U) nucleotides or modified nucleotides thereof. In some embodiments, the nucleic acid label can comprise only four of the A, G, C, and T (and/or U) nucleotides or modified nucleotides thereof. The subset of the A, G, C and T (and/or U) nucleotides or modified nucleotide thereof can be selected from the group consisting of A; G; C; T; U; (A,G); (A,C); (G,T); (G,U); (C,T); (C,U); (G,T,U); (C,T,U); (A,C, G); (A,G,T); (A,G,U); (A,C,T); (A,C,U); (C,G,T); (C,G,U); (A,C,T,U); and (C,G,T,U).

Without wishing to be bound, the nucleic acid label can be a modified nucleic acid label. An exemplary modification of the nucleic acid label includes, without limitations, attaching one or more detectable molecules to the nucleic acid label (either to one end of or along the nucleic acid label sequence). The detectable molecule can be any optical molecule, including, but not limited to, a small-molecule dye, a fluorescent protein, a quantum dot, or any combinations thereof. In another embodiment, at least one end of the nucleic acid label can be modified to include a chemical functional group and/or a protein or peptide to facilitate the conjugation between the nucleic acid label and the probe reagent.

In some embodiments, at least one (including, e.g., at least two, at least three, at least four, at least five, at least six or more) nucleic acids or nucleotides present in the nucleic acid label can be modified. For example, the nucleic acid can comprise one or more nucleic acid modifications as described herein, e.g., selected from the group consisting of internucleotide linkage modifications (intersugar linkage modifications), sugar modifications, nucleobase modifications, backbone modifications/replacements, and any combinations thereof.

Conjugation Between a Nucleic Acid Label and a Probe Reagent

In accordance with embodiments of various aspects described herein, the detection reagent comprises at least one probe reagent and at least one nucleic acid label, wherein the probe reagent and the nucleic acid label can be conjugated together by any methods known in the art.

In some embodiments, the probe reagent and the nucleic acid label can be attached or conjugated together by a linker. As used herein, the term "linker" generally refers to an entity that connects the probe reagent and the nucleic acid label together. The linker can be monovalent or multivalent. The term "monovalent" as used herein refers to the capacity of a linker to join one probe reagent to one nucleic acid label. The term "multivalent" as used herein refers to the capacity of a linker to bind with one or more probe reagents and/or nucleic acid labels. In some embodiments, a multivalent linker can join at least one probe reagent to a plurality of nucleic acid labels (e.g., 2, 3, 4, 5, 6, 7, 8, 9, 10 or more nucleic acid labels).

In some embodiments, the term "linker" means an organic moiety that connects two parts of a compound. Such linkers typically comprise a direct bond or an atom such as oxygen or sulfur, a unit such as NH, C(O), C(O)NH, SO, SO$_2$, SO$_2$NH, SS, or a chain of atoms, such as substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_6$-C$_{12}$ aryl, substituted or unsubstituted C$_5$-C$_{12}$ heteroaryl, substituted or unsubstituted C$_5$-C$_{12}$ heterocyclyl, substituted or unsubstituted C$_3$-C$_{12}$ cycloalkyl, where one or more methylenes can be interrupted or terminated by O, S, S(O), SO$_2$, NH, C(O).

In some embodiments, the linker is a branched linker. The branchpoint of the branched linker may be at least trivalent, but can be a tetravalent, pentavalent or hexavalent atom, or a group presenting such multiple valencies. In some embodiments, the branchpoint is —N, —N(R)—C, —O—C, —S—C, —SS—C, —C(O)N(R)—C, —OC(O)N(R)—C, —N(R)C(O)—C, or —N(R)C(O)O—C; wherein R is independently for each occurrence H or optionally substituted alkyl. In some embodiments, the branchpoint is glycerol or derivative thereof.

In some embodiments, linker comprises a cleavable linking group. As used herein, a "cleavable linking group" is a chemical moiety which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. For example, for liver targeting, cleavable linking groups can include an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or C$_1$-C$_6$ alkyl and at least one R is C$_1$-C$_6$ alkyl such as CH$_3$ or CH$_2$CH$_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched C$_1$-C$_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleaveable in an acidic environment with a pH of about 6.5 or lower (e.g., about 6.0, 5.5, 5.0, or lower), or by agents such as enzymes that can act as a general acid.

In addition to covalent linkages, two parts of a compound can be linked together by an affinity binding pair. The term "affinity binding pair" or "binding pair" refers to first and second molecules that specifically bind to each other. One member of the binding pair is conjugated with first part to be linked while the second member is conjugated with the second part to be linked. As used herein, the term "specific binding" refers to binding of the first member of the binding pair to the second member of the binding pair with greater affinity and specificity than to other molecules.

Exemplary binding pairs include any haptenic or antigenic compound in combination with a corresponding antibody or binding portion or fragment thereof (e.g., digoxigenin and anti-digoxigenin; mouse immunoglobulin and goat antimouse immunoglobulin) and nonimmunological binding pairs (e.g., biotin-avidin, biotin-streptavidin, biotin-neutravidin, hormone [e.g., thyroxine and cortisol-hormone binding protein, receptor-receptor agonist, receptor-receptor antagonist (e.g., acetylcholine receptor-acetylcholine or an analog thereof), IgG-protein A, IgG-protein G, IgG-synthesized protein AG, lectin-carbohydrate, enzyme-enzyme cofactor, enzyme-enzyme inhibitor, and complementary oligonucleotide pairs capable of forming nucleic acid duplexes), and the like. The binding pair can also include a first molecule which is negatively charged and a second molecule which is positively charged.

One example of using binding pair conjugation is the biotin-avidin, biotin-streptavidin or biotin-neutravidin conjugation. In this approach, one of the molecule or the peptide is biotinylated and the other is conjugated with avidin or streptavidin. Many commercial kits are also available for biotinylating molecules, such as proteins.

Another example of using binding pair conjugation is the biotin-sandwich method. See, e.g., example Davis et al., Proc. Natl. Acad. Sci. USA, 103: 8155-60 (2006). The two molecules to be conjugated together are biotinylated and then conjugated together using at least one tetravalent avidin-like molecule (e.g., avidin, streptavidin, or neutravidin) as a linker.

Accordingly, in some embodiments, both the nucleic acid label(s) and probe reagent(s) can be biotinylated and then linked together using an avidin-like molecule (e.g., avidin, streptavidin, or neutravidin). In one embodiment, neutravidin and/or streptavidin is used as a linker to bridge together the biotinylated nucleic acid label(s), e.g., DNA sequence(s), and biotinylated probe reagent(s), e.g., antibody. Without wishing to be bound by theory, each avidin-like molecule (e.g., avidin, streptavidin, or neutravidin) generally has four binding sites, so at most four molecules can be linked together. For example, one biotinylated probe reagent can be linked, via an avidin-like molecule (e.g., avidin, streptavidin or neutravidin), to three biotinylated nucleic acid labels, or in any other combinations (e.g., two biotinylated probe reagents linked to two biotinylated nucleic acid labels).

Biotinylation of a nucleic acid label (i.e., attaching a biotin to a nucleic acid label) can occur at any location of the nucleic acid label. In some embodiments, the nucleic acid label can by synthesized or modified with a terminal biotin, i.e., the nucleic acid label can have a biotin at its 5' end and/or 3' end. In other embodiments, the nucleic acid label can by synthesized or modified with an internal biotin, i.e., the nucleic acid label can have a biotin anywhere between its 5' and 3' ends, but not at its 5' and/or 3' ends. Such internal biotinylation can leave at least one end (e.g., both ends) of the nucleic acid label accessible, allowing the nucleic acid label to be circularized after the nucleic acid label has bound, which can in turn, for example, enable rolling circle amplification as described earlier. Chemical modification of the nucleic acid label, e.g., to attach a terminal and/or an internal biotin to the nucleic acid label after synthesis, is within one of skill in the art.

For some embodiments where the probe reagent is a nucleic acid, an example of using binding pair conjugation is double-stranded nucleic acid conjugation. In this approach, the first part to be linked is conjugated is with linked a first strand first strand of the double-stranded nucleic acid and the second part to be linked is conjugated with the second strand of the double-stranded nucleic acid. Nucleic acids can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges.

In some embodiments, the linker can be a linker molecule. Examples of linker molecules can include, but are not limited to, a polymer, sugar, nucleic acid, peptide, protein, hydrocarbon, lipid, polyethelyne glycol, crosslinker, or combination thereof.

Non-limiting examples of crosslinkers that can be used as linker molecules can include, but are not limited to, amine-to-amine crosslinkers (e.g., but are not limited to the ones based on NHS-ester and/or imidoester reactive groups), amine-to-sulfhydryl crosslinkers, carboxyl-to-amine cross-linkers (e.g., but are not limited to, carbodiimide crosslinking agents such as DCC, and/or EDC (EDAC); and/or N-hydroxysuccinimide (NHS)), photoreactive crosslinkers (e.g., but not limited to, aryl azide, diazirine and any art-recognized photo-reactive (light-activated) chemical crosslinking reagents), sulfhydryl-to-carbohydrate cross-linkers (e.g., but are not limited to the ones based on malemide and/or hydrazide reactive groups), sulfhydryl-to hydroxyl crosslinkers (e.g., but are not limited to the ones based on maleimide and/or isocyanate reactive groups), sulfhydryl-to-sulfhydryl crosslinkers (e.g., but are not limited to, maleimide and/or pyridyldithiol reactive groups), sulfo-SMCC crosslinkers, sulfo-SBED biotin label transfer reagents, sulfhydryl-based biotin label transfer reagents, photoreactive amino acids (e.g., but are not limited to diazirine analogs of leucine and/or methionine), NHS-azide Staudinger ligation reagents (e.g., but are not limited to, activated azido compounds), NHS-phosphine Staudinger ligation reagents (e.g., but are not limited to, activated phosphine compounds), and any combinations thereof.

In some embodiments, any commercially available cross-linkers (e.g., but not limited to the ones from Thermo Scientific or Piercenet, Rockford, Ill.) can be used as a linker molecule herein.

In some embodiments, the term "linker" as used herein can be a physical substrate. In some embodiments, the physical substrate is a particle. The particle can be of any shape, e.g., spheres; rods; shells; beads, tubes, wires, and prisms; and these particles can be part of a network.

The particles can be made of any materials. In some embodiments, the particle can comprise a material selected from the group consisting of metal (e.g., gold, or iron), metal oxides (e.g., iron oxide), plastic, glass, polymer (e.g., polystyrene), and any combinations thereof.

For in vivo purposes, e.g., disease and/or pathogen diagnosis and/or targeted drug delivery, the polymer can be biocompatible and/or biodegradable. The term "biocompatible polymer" refers to polymers which, in the amounts employed, are non-toxic and substantially non-immunogenic when used internally in the patient and which are substantially insoluble in the body fluid of the mammal. Examples of non-biodegradable biocompatible polymers include, by way of example, cellulose acetates (including cellulose diacetate), ethylene vinyl alcohol copolymers, hydrogels (e.g., acrylics), polyacrylonitrile, polyvinylacetate, cellulose acetate butyrate, nitrocellulose, copolymers of urethane/carbonate, copolymers of styrene/maleic acid, and any combinations thereof. Biodegradable polymers are known in the art, e.g., without limitations, linear-chain polymers such as polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosa, and copolymers, terpolymers and any combinations thereof. Other biodegradable polymers include, for example, fibrin, gelatin, collagen, and any combinations thereof.

The particles can be of any size for the purpose of various aspects described herein, provided that the particle size does not significantly affect the diffusion property of the detection reagent. For example, the particle size can range from 5 nm to 1 mm, from about 10 nm to about 500 µm, or from about 50 nm to about 250 µm. In some embodiments, a particle described herein is a nanoparticle or a microparticle. As used herein, the term "nanoparticle" refers to particles that are on the order of $10^{-9}$ or one billionth of a meter and below $10^{-6}$ or 1 millionth of a meter in size. The term "microparticle" as used herein refers to particles that are on the order of $10^{-6}$ or one millionth of a meter and below $10^{-3}$ or 1 thousandth of a meter in size. In some embodiments, the particle can be selected from a group consisting of a gold nanoparticle or microparticle, a paramagnetic nanoparticle or microparticle, a magnetic nanoparticle or microparticle, a polystyrene nanoparticle or microparticle, a nanotube or a microtube, a nanowire or a microwire, and any combinations thereof.

The particles can be adapted to possess at least one additional property, depending on various applications. In some embodiments, the particles can be adapted to be magnetic responsive or paramagnetic-responsive, e.g., magnetic or paramagnetic particles. In some embodiments, the particles can be adapted to be a delivery vehicle. For example, in some embodiments, the particles can be encapsulated with a therapeutic agent, e.g., for targeted drug delivery to treat a disease or disorder.

In some embodiments, the particles can be modified. For example, the particles can be conjugated with proteins, peptides, nucleic acids, or any combinations thereof. In one embodiment, the particles can be surface-conjugated or coated with one member of the binding pair as described above (e.g., for biotin-streptavidin interaction, streptavidin-coated particles can be used for the purpose of various aspects described herein). In some embodiments, the particles can be surface-activated with functional groups (e.g., but not limited to, amine, carboxylic acid, epoxy, tosyl, silane, and any combinations thereof), e.g., to provide binding sites for probe reagents and/or nucleic acid labels. Methods for surface modifications of particles, such as nanoparticles or microparticles, are well known in the art. One of skill in the art can readily modify or activate the surface of particles using any art-recognized reactions, e.g., covalently through crosslinkers, or through protein interaction.

The particles described herein can be used in conjunction with the organic linker described above, to form a conjugate linker, or the particles can be used alone as a linker. Both the nucleic acid labels and the probe reagents can be coupled to the particles using a multitude of methods. These include, but are not limited to, direct covalent attachment such as using chemical crosslinkers based on chemistries such as NHS, maleimide, tosyl, isocyanide, etc.; chemical linkage such as using EDC chemistry, thiol adsorption to gold, vinyl/acrylate radical reaction, acrylate-based addition (of e.g., thiols); and protein mediated couplings based on proteins such as streptavidin (and its relatives such as avidin, neutravidin, etc.), protein A, and secondary antibodies, and any combinations thereof.

The particles can act as hubs that facilitate a conjugation of multiple nucleic acid labels to single or multiple probes. Depending on applications and/or properties of nucleic acid labels and/or probe reagents, particles can be used as hubs for multi-conjugation. For example, in some embodiments, by acting as a hub, the particles can allow multiple nucleic acid labels to be present at each location (e.g., location of a target molecule or analyte) where the probe binds. Accordingly, the signal generated from the detection reagent can be amplified and thus greater than if only a single label was present. This is especially desirable where antigens/targets or analytes are sparse in a sample.

In some embodiments, the particles can allow multiple probes to be arranged in proximity to each other. Thus, the particles can allow several weaker binding events to combine into strong binding. This "avidity action" can transform probe reagents with individually weak affinities into effective sensors.

In some embodiments, by acting as a hub, the particles can allow each probe reagent to conjugate to multiple nucleic acid labels. This capability can eliminate the need for other amplification methods (e.g., rolling circle amplification) as multiple nucleic acid labels corresponding to a probe reagent can be used as a form of signal amplification. In some embodiments, this capability can also be used to separate the detection reagents with one nucleic acid label from the ones with different nucleic acid labels, which can, in turn, enable, for example, sequencing by single-base extension. Furthermore, different nucleic acid labels can be conjugated to the particles at controlled ratios, and the ratios can encode additional information. By way of example only, to capture in situ information of one or more enzymes' behavior (e.g., relative enzyme concentration) in the presence of an analyte, two or more different nucleic acid labels can be conjugated to the particles, wherein a subpopulation of the nucleic acid labels corresponding to the probe reagent is not cleavable, while other subpopulations of the nucleic acid labels are each adapted to be cleavable in the presence of their respective enzymes. In such embodiments, the cleavable nucleic acid labels can be conjugated to the particles by cleavable peptide bonds specific for corresponding enzymes. By comparing the ratios of signals generated from the various nucleic acid labels, one would be able to determine the relative enzyme concentrations in the presence of an analyte.

Figure 6:
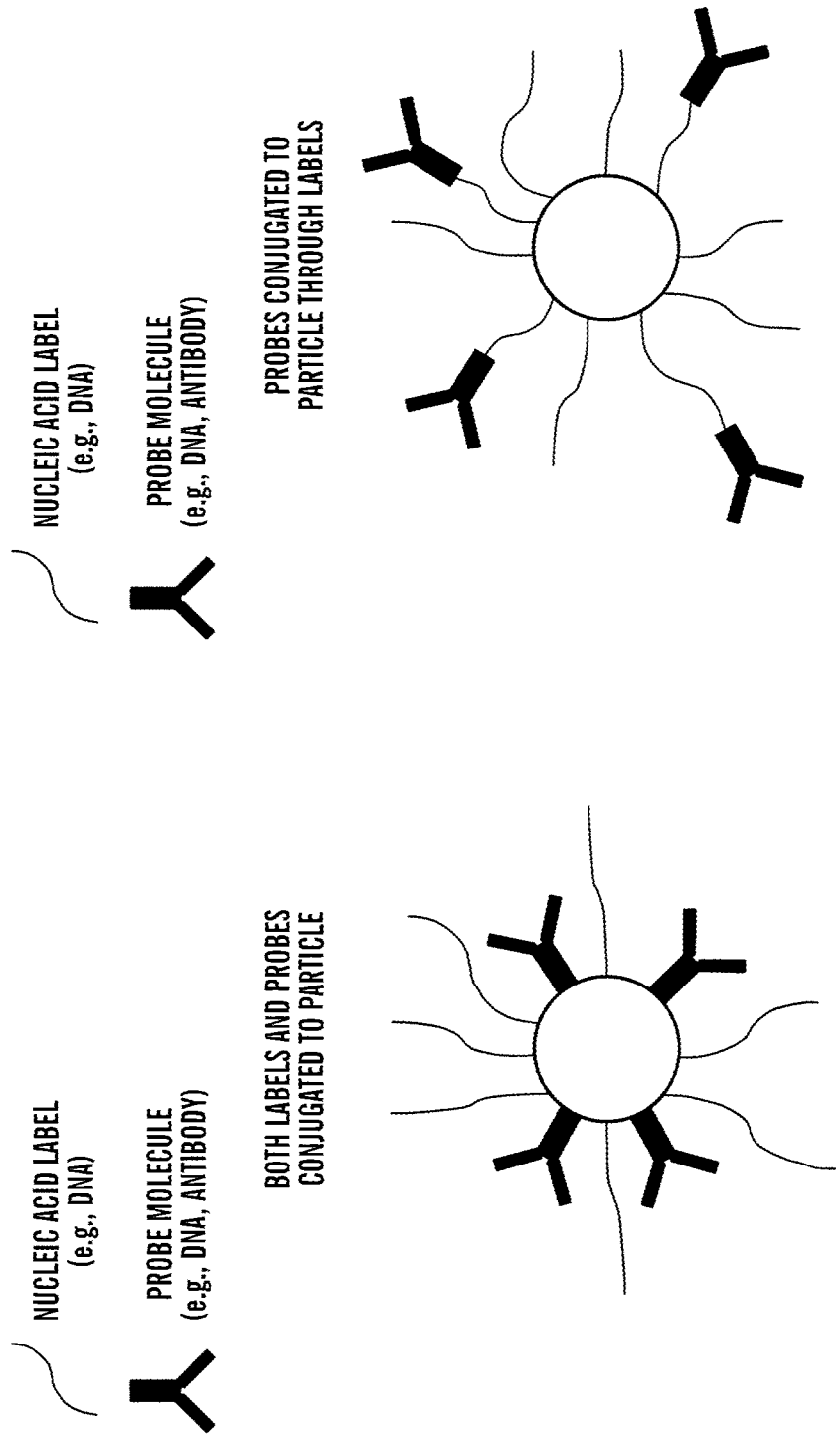
FIGS. 6A and 6B shows two exemplary configurations of probe reagents and nucleic acid labels on particles, in accordance with one or more embodiments described herein.

The arrangement of the probe reagent(s) and/or nucleic acid label(s) on the particles can vary with a number of factors, e.g., applications, properties of probe reagents and/or nucleic acid labels, sample properties, and/or analytes of interests. In some embodiments, the probe reagents and nucleic acid labels can be conjugated to the particle directly (see, e.g., FIG. 6A). In some embodiments, one component can be linked to the particle through the other. In such embodiments, the probe reagents can be conjugated or linked to the particle through the nucleic acid labels (see, e.g., FIG. 6B), e.g., to allow the probe reagents being more accessible by the corresponding analytes in a sample.

In some embodiments, the detection reagents can further comprise at least one substrate linker conjugated to the particle. In such embodiment, the substrate linker can allow the detection reagents to be immobilized to a solid support or substrate.

Detectable Molecules or Detectable Labels

A detectable molecule or detectable label can be covalently attached to a decoder probe or complementary nucleobase before or after the decoder probe or the complementary nucleobase is attached to the pre-determined subsequences or hybridization sites of a nucleic acid label. For example, in attaching a detectable label to a decoder probe, the label can be covalently attached by incorporation of a nucleotide containing a detectable label into the nucleic acid during its synthesis, but before it is hybridized the pre-determined subsequence of the nucleic acid label. Alternatively, during the synthesis of a decoder probe sequence, a nucleotide containing a detectable label acceptor group can be included, and the detectable label can be added to the decoder probe after its synthesis, either before or after it is hybridized to the pre-determined subsequences of the nucleic acid label. Alternatively, the detectable label can be indirectly attached to the decoder probe, for example, by incorporating a nucleotide containing a ligand-binding molecule (e.g., biotin) into the decoder probe during synthesis, and by adding a ligand (e.g., streptavidin) that is covalently attached to the detectable molecule, or vice versa.

In some embodiments, the ratios of a detectable label to a decoder probe can range from about 1:1 to about 100:1, from 1:1 to about 50:1, from about 1:1 to about 25:1, from about 1:1 to about 10:1, or from about 1:1 to about 5:1. When a decoder probe comprises more than one detectable label, each detectable label can be attached to a nucleotide of the decoder probe.

A detectable label or a detectable molecule can be attached to any nucleotide including both natural and non-natural nucleotides. A nucleotide contains three parts, a phosphate group, a pentose five-carbon sugar molecule, and an organic base. In RNA, the pentose is ribose and in DNA it is deoxyribose and so nucleotides for incorporation into RNA are called ribonucleotides and nucleotides for incorporation into DNA are called deoxyribonucleotides. Three bases adenine, guanine, and cytosine are found in both DNA and RNA while thymine is normally found only in DNA and uracil is normally found only in RNA. Nucleotides can have one, two or three attached phosphate groups and are sometimes referred to as nucleoside phosphates. Nucleotides can contain modified nucleosides having modified bases (e.g., 5-methyl cytosine) and modified sugar groups (e.g., 2'O-methyl ribosyl, 2'O-methoxyethyl ribosyl, 2'fluoro ribosyl, 2'amino ribosyl, and the like). An example of non-natural bases that are used in the art are isocytidine and isoguanine.

A detectable label or a detectable molecule as used herein is intended to mean an individual measurable moiety, such as a radioisotope, fluorochrome, dye, enzyme (including its effect on a substrate), nanoparticle, chemiluminescent marker, biotin, or other moiety known in the art that is measurable by analytical methods. A detectable label or a detectable molecule can be attached to a nucleotide using methods well known in the art and exemplified herein.

Without limitations, examples of a detectable label or a detectable molecule that can be utilized by some aspects described herein can include optical reporters or optical labels. Suitable optical reporters or optical labels include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Suitable fluorescent reporters include xanthene dyes, such as fluorescein or rhodamine dyes, including, but not limited to, Alexa Fluor® dyes (InvitrogenCorp.; Carlsbad, Calif.), fluorescein, fluorescein isothiocyanate (FITC), Oregon Green™, rhodamine, Texas red, tetrarhodamine isothiocynate (TRITC), 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N,N'-tetramefhyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylamino-naphthyl-5-sulfonate, 1-anilino-8-naphthalene sulfonate, 2-p-toluidinyl-6-naphthalene sulfonate, and 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p(2-benzoxazolyl)phenyl)maleimide; cyanines, such as Cy2, indodicarbocyanine 3 (Cy3), indodicarbocyanine 5 (Cy5), indodicarbocyanine 5.5 (Cy5.5), 3-(-carboxy-pentyl)-3'ethyl-5,5'-dimethyloxacarbocyanine (CyA); 1H,5H,11H, 15H-Xantheno[2,3,4-ij:5,6,7-i'j']diquinolizin-18-ium, 9-[2 (or 4)-[[[6-[2,5-dioxo-1-pyrrolidinyl)oxy]-6-oxohexyl] amino]sulfonyl]-4(or 2)-sulfophenyl]-2,3,6,7,12,13,16, 17octahydro-inner salt (TR or Texas Red); BODIPY™ dyes; benzoxadiazoles; stilbenes; pyrenes; and the like. Many suitable forms of these fluorescent compounds are available and can be used.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403, 374, 6,800,733, and 7,157,566). Specific examples of GFP variants include, but are not limited to, enhanced GFP (EGFP), destabilized EGFP, the GFP variants described in Doan et al, Mol. Microbiol, 55:1767-1781 (2005), the GFP variant described in Crameri et al, Nat. Biotechnol., 14:315319 (1996), the cerulean fluorescent proteins described in Rizzo et al, Nat. Biotechnol, 22:445 (2004) and Tsien, Annu. Rev. Biochem., 67:509 (1998), and the yellow fluorescent protein described in Nagal et al, Nat. Biotechnol., 20:87-90 (2002). DsRed variants are described in, e.g., Shaner et al, Nat. Biotechnol., 22:1567-1572 (2004), and include mStrawberry, mCherry, morange, mBanana, mHoneydew, and mTangerine. Additional DsRed variants are described in, e.g., Wang et al, Proc. Natl. Acad. Sci. U.S.A., 101:16745-16749 (2004) and include mRaspberry and mPlum. Further examples of DsRed variants include mRFPmars described in Fischer et al, FEBS Lett., 577:227-232 (2004) and mRFPruby described in Fischer et al, FEBS Lett, 580:2495-2502 (2006).

Amine-reactive and thiol-reactive fluorophores are available and generally used for labeling nucleotides and biomolecules. In some embodiments, nucleotides are fluorescently labeled during chemical synthesis, for example, incorporation of amines or thiols during nucleotide synthesis permit addition of fluorophores. Fluorescently labeled nucleotides are commercially available. For example, uridine and deoxyuridine triphosphates are available that are conjugated to ten different fluorophores that cover the spectrum.

In some embodiments, radioisotopes can be utilized as detectable molecules or detectable molecules for labeling nucleotides including, for example, $^{32}P$, $^{33}P$, $^{35}S$, $^{3}H$, and $^{125}I$. These radioisotopes have different half-lives, types of decay, and levels of energy which can be tailored to match the needs of a particular experiment. For example, $^{3}H$ is a low energy emitter which results in low background levels, however this low energy also results in long time periods for autoradiography. Radioactively labeled ribonucleotides and deoxyribonucleotides are commercially available. Nucleotides are available that are radioactively labeled at the first, or α, phosphate group, or the third, or γ, phosphate group. For example, both [α-$^{32}P$]dATP and [γ-$^{32}P$]dATP are commercially available. In addition, different specific activities for radioactively labeled nucleotides are also available commercially and can be tailored for different experiments.

Suitable non-metallic isotopes include, but are not limited to, $^{11}C$, $^{14}C$, $^{13}N$, $^{18}F$, $^{123}I$, $^{124}I$, and $^{125}I$. Suitable radioisotopes include, but are not limited to, $^{99m}Tc$, $^{95}Tc$, $^{111}In$, $^{62}Cu$, $^{64}Cu$, Ga, $^{68}Ga$, and $^{153}Gd$. Suitable paramagnetic metal ions include, but are not limited to, Gd(III), Dy(III), Fe(III), and Mn(II). Suitable X-ray absorbers include, but are not limited to, Re, Sm, Ho, Lu, Pm, Y, Bi, Pd, Gd, La, Au, Au, Yb, Dy, Cu, Rh, Ag, and Ir. In some embodiments, the radionuclide is bound to a chelating agent or chelating agent-linker attached to the aggregate. Suitable radionuclides for direct conjugation include, without limitation, $^{18}F$, $^{124}I$, $^{125}I$, $^{131}I$, and mixtures thereof. Suitable radionuclides for use with a chelating agent include, without limitation, $^{47}Sc$, $^{64}Cu$, $^{67}Cu$, $^{89}Sr$, $^{86}Y$, $^{87}Y$, $^{90}Y$, $^{105}Rh$, $^{111}Ag$, $^{111}In$, $^{117m}Sn$, $^{149}Pm$, $^{153}Sm$, $^{166}Ho$, $^{177}Lu$, $^{186}Re$, $^{188}Re$, $^{211}At$, $^{212}Bi$, and mixtures thereof. Suitable chelating agents include, but are not limited to, DOTA, BAD, TETA, DTPA, EDTA, NTA, HDTA, their phosphonate analogs, and mixtures thereof. One of skill in the art will be familiar with methods for attaching radionuclides, chelating agents, and chelating agent-linkers to the particles.

Non-radioactive and non-fluorescent label monomers are also available. For example, biotin can be attached directly to nucleotides and detected by specific and high affinity binding to avidin or streptavidin which has been chemically coupled to an enzyme catalyzing a colorimetric reaction (such as phosphatase, luciferase, or peroxidase). Digoxigenin labeled nucleotides can also similarly be used for non-isotopic detection of nucleic acids. Biotinylated and digoxigenin-labeled nucleotides are commercially available.

In some embodiments, enzymatic reaction on a substrate can be utilized a detection method. In such embodiments, enzymes (e.g., horseradish peroxidase or alkaline phosphatase) can be linked to a nucleotide of a nucleic acid label and/or decoder probe. During detection, a substrate on which the particular enzyme reacts can be added to induce a colorimetric reaction. Any enzyme-substrate reactions known in the art can be used herein.

Very small particles, termed nanoparticles, also can be used as detectable labels or detectable molecules to label decoder probes or any nucleic acids. These particles range from 1-1000 nm in size and include diverse chemical structures such as gold and silver particles and quantum dots.

When irradiated with angled incident white light, silver or gold nanoparticles ranging from 40-120 nm will scatter monochromatic light with high intensity. The wavelength of the scattered light is dependent on the size of the particle. Four to five different particles in close proximity will each scatter monochromatic light which when superimposed will give a specific, unique color. Alternatively, the gold nanoparticles can be detected or "developed" using a silver-based developer such that the tiny nanoparticle can be detected easily, even with naked eyes. The particles are being manufactured by companies such as Genicon Sciences. Derivatized silver or gold particles can be generally attached to a broad array of molecular molecules including, proteins, antibodies, small molecules, receptor ligands, and nucleic acids. For example, the surface of the particle can be chemically derivatized to allow attachment to a nucleotide, which can then be incorporated into a decoder probe.

Another type of nanoparticle that can be used as a detectable molecule or detectable label are quantum dots. Quantum dots are fluorescing crystals 1-5 nm in diameter that are excitable by a large range of wavelengths of light. These crystals emit light, such as monochromatic light, with a wavelength dependent on their chemical composition and size. Quantum dots such as CdSe, ZnSe, InP, or InAs possess unique optical properties.

Due to their very small size the quantum dots can be generally coupled into oligonucleotides directly without affecting the solubility or use of the oligonucleotide. Thus, quantum dots can be coupled to decoder probes as described herein. To synthesize a decoder probe-quantum dot complex by conventional batch chemistry, both the decoder probe and the quantum dot require at least a reactive group of different kinds that can be reacted with each other. For example, if a decoder probe has an amino group and a quantum dot has an aldehyde group, these groups can react to form a Schiff base. A decoder probe can be derivatized to attach a single amino or other functional group using chemistry well known in the art. When a quantum dot is derivatized, the quantum dot can be covered with a chemical reagent which results in coating the entire surface of the nanoparticle with several functional groups.

A detectable molecule or detectable label can be attached to a nucleotide of a decoder probe or nucleic acid using a variety of methods well known in the art and described herein. For example, the detectable molecule or detectable label can be directly attached to the nucleotide in a 1:1 correspondence by incorporation of a radioactive phosphate into the phosphate backbone of the nucleotide. Also, for example, a general method for labeling phosphates with a fluorescent label that employs an imidazole derivative prepared from a BODIPY FL hydrazide has been reported (Wang and Giese, Anal. Chem. 65: 3518 (1993).

Depending on the labeling moiety used, it can be desirable to derivatize or chemically modify a nucleotide in order to bind the label monomer. These methods and chemistries are known in the art. In addition, a linker can be used to attach a detectable molecule or detectable label to a nucleotide in a 1:1 correspondence. For example, a fluorescently labeled nucleotide such as fluorescein-12-dUTP can have a fluorophore monomer attached via a four-atom aminoalkynyl group to the dUTP molecule.

These nucleotides attached to detectable molecules or detectable labels can be incorporated into a decoder probe or nucleic acid using several methods for labeling nucleic acids well known in the art. For example, enzymes such as DNA or RNA polymerases, Taq polymerases, terminal deoxynucleotidyl transferases, or reverse transcriptases can be used to incorporate labeled nucleotides into decoder probes or nucleic acids.

Labeled nucleotides can be incorporated into decoder probe sequences or nucleic acids, for example, by nick translation. In this procedure DNAse I is used to create single-strand nicks in double stranded DNA and then the 5' to 3' exonuclease and 5' to 3' polymerase actions of E. coli DNA polymerase I are used to remove stretches of single stranded DNA starting at the nicks and replace them with new strands made by incorporation of labeled nucleotides. Nick translation can utilize any labeled nucleotide including radioactively labeled nucleotides and biotinylated or digoxigenin labeled nucleotides. In a similar way T4 DNA polymerase can be used to incorporate labeled nucleotides. In addition, labeled nucleotides can be incorporated into nucleic acids using the polymerase chain reaction (PCR) and Taq polymerases. The degree of labeling can be controlled by including one, or up to all four labeled nucleotides. In addition, the degree of labeling can be controlled by increasing or decreasing the concentration of the labeled nucleotide(s).

Other methods for labeling decoder probes or nucleic acids include generating single-stranded cDNA from RNA by using a reverse transcriptase in the presence of labeled nucleotides. In addition, DNA can be cloned into a vector with SP6 or T7 polymerase sites. Transcription in the presence of SP6 or T7 RNA polymerase and labeled nucleotides results in a labeled RNA transcript. The transcript can be labeled to different degrees by including one or more labeled nucleotides. In addition, several nucleotides within a nucleic acid can be labeled, for example, by cloning DNA into a bacteriophage M13 based vector. Then the Klenow fragment of DNA polymerase I and the M13 universal probe primer can be used to synthesize the complementary stand with incorporation of labeled nucleotides.

Several methods are described above for incorporation of labeled nucleotides into newly synthesized decoder probes or nucleic acids. Existing nucleic acids can also be labeled using several methods known in the art. For example, RNA or DNA can be end-labeled with [γ-32P]ATP and T4 polynucleotide kinase. This kinase can be used to transfer the radioactive phosphate of ATP to a free 5' OH group in either DNA or RNA. The enzyme also has a phosphatase activity and so two reactions are possible. In the forward reaction, the enzyme catalyzes phosphorylation following removal of 5' terminal phosphates with alkaline phosphatase (or other phosphatase). In the exchange reaction, the kinase catalyzes the exchange of an existing 5' phosphate with the third or γ phosphate of ATP. The latter reaction is carried out in the presence of excess ATP and ADP for efficient phosphorylation. Using this method the radioactive phosphate of ATP is transferred to the end of the nucleic acid molecule.

Decoder probes or nucleic acids can also be labeled with terminal deoxynucleotidyl transferase which adds labeled nucleotides onto the 3' end of DNA fragments. Both single and double-stranded DNAs are substrates for this enzyme. The large (Klenow) fragment of E. coli DNA polymerase I can also be used to label the ends of decoder probes or nucleic acids. Since this enzyme has a 5' to 3' polymerase activity it can be used to "fill in" the 3' ends of nucleic acid (e.g., DNA) fragments opposite of 5' extensions or overhangs with labeled nucleotides. End-labeling of decoder probes or nucleic acids using polynucleotide kinase or terminal deoxynucleotidyl transferase results in the incorporation of one detectable label or detectable molecule per nucleic acid. The "fill in" reaction can be used to label the decoder probe or nucleic acid at one nucleotide per nucleic acid or at more than one nucleotide per nucleic acid.

In addition, decoder probes or nucleic acids can be labeled by modification of nucleotides within the nucleic acid sequences. For example, cytidine residues in DNA and RNA can be modified by reaction with sodium bisulfite to form sulfonate intermediates that can then be directly coupled to hydrazides or aliphatic amines. Virtually any of the fluorescent, biotin or other hydrazides or aliphatic amines can be used in this reaction. The bisulfite-activated cytidylic acid can also be coupled to aliphatic diamines such as ethylenediamine. The amine-modified nucleic acids (e.g., DNA or RNA) can then be modified with any of the amine-reactive dyes. In addition, phosphate groups can be targeted in nucleic acids for labeling. Although phosphate groups of nucleotides are not very reactive in aqueous solution, their terminal phosphate groups can react with carbodiimides and similar reagents in combination with nucleophiles to yield labeled phsophodiesters, phosphoramidates and phosphorothioates. For example, nucleic acids (e.g., DNA) can be reacted quantitatively with carbonyl diimidazole and a diamine such as ethylenediamine to yield a phosphoramidate that has a free primary amine and that this amine can then be modified with amino-reactive reagents. Fluorescent or biotinylated amines have been coupled to the 5' phosphate of tRNA using dithiodipyridine and triphenylphosphine.

The bond between detectable molecules or detectable labels and decoder probes or nucleic acids can be covalent bonds or non-covalent bonds that are stable to hybridization. The detectable molecules or detectable labels can be bound to a decoder probe or a nucleic acid in a sequence specific manner, for example by the incorporation of a labeled nucleotide into a sequence that has been digested by a restriction enzyme. Alternatively the detectable molecules or detectable labels can be bound to a decoder probe or a nucleic acid in a non-sequence specific manner, for example by the incorporation of a label onto the terminal phosphate of a nucleic acid using [γ-$^{32}$P]ATP and T4 polynucleotide kinase.

Synthesis of Nucleic Acids (e.g., for at Least Part of the Nucleic Acid Label Such as Pre-Determined Subsequences and/or Decoder Probe Sequences The nucleic acids described herein can be chemically synthesized using naturally occurring nucleotides or variously modified nucleotides designed to increase the biological stability of the molecules or to increase the physical stability of the duplex formed between the label attachment region and the annealed complementary polynucleotide sequences or segments, e.g., phosphorothioate derivatives and acridine substituted nucleotides can be used. Examples of modified nucleotides which can be used to generate the synthetic nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl)uracil, (acp3)w, and 2,6-diaminopurine.

Alternatively, the synthetic nucleic acid can be produced biologically using a vector into which a nucleic acid has been subcloned. As one example, a linear single-stranded DNA backbone can be made from a double stranded plasmid DNA using a four step protocol that includes (i) linearization of the dsDNA with a restriction enzyme, (ii) dephosphorylation with a thermolabile phosphatase, (iii) digestion with a second restriction enzyme to separate the cloning vector from the backbone sequence, and (iv) digestion with a strand-specific lambda exonuclease digestion, leaving only one strand of the backbone fragment intact.

In various embodiments, the nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al, 1996, Bioorganic & Medicinal Chemistry 40:5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al, 1996, Bioorganic & Medicinal Chemistry 4(1): 5-23; Perry-O'Keefe et al., 1996, Proc. Natl. Acad. Sci. USA 93: 14670-675.

In an exemplary embodiment, the selected novel nucleic acid sequence (e.g., DNA sequence) can be constructed synthetically as double-stranded nucleic acid by a commercial gene synthesis company and cloned in an oriented fashion into a "phagemid", a plasmid vector containing an M13 or f1 phage intergenic (IG) region which contains the cis-acting sequences necessary for nucleic acid (e.g., DNA) replication and phage encapsidation, such as pUC119. The appropriate orientation of the cloned insert relative to the phage origin of replication allows for the generation of a single-stranded DNA backbone which is the reverse complement of the RNA molecules generated by in vitro transcription for each label attachment region.

In order to generate the single-stranded nucleic acid (e.g., DNA) backbone (e.g., of at least part of the nucleic acid label and/or decoder probes), the phagemid is transformed into an *E. coli* strain containing an F' episome. Subsequent infection of the transformed bacteria with a helper phage such as the M113 mutant K07 results in the secretion of the phagemid carrying the single-stranded nucleic acid sequence, packaged phage from which the circular, single-stranded nucleic acid is prepared using a standard protocol. This nucleic acid is linearized and the vector portion is excised by annealing short, complementary oligonucleotides to either end of the single-strander nucleic acid sequence to generate double-stranded restriction sites, followed by treatment with the appropriate restriction enzymes.

Analytes or Target Molecules

The terms "analyte," "target analyte," and "target molecule", as used interchangeably herein, refer to the molecule detected, identified or measured by binding of a detection reagent described herein whose probe reagent(s) recognize (i.e., are specific binding partners) thereto. In some embodiments, a target molecule or an analyte can be, but is not limited to, any of the following or any combinations of the following: nucleic acid, peptide, a polypeptide/protein (e.g., a bacterial or viral protein or an antibody), a lipid, a carbohydrate, a glycoprotein, a glycolipid, a small molecule, an organic monomer, sugar, peptidoglycan, a cell, a virus or a drug. Nucleic acids that can be analyzed by the methods herein include: double-stranded DNA, single-stranded DNA, single-stranded DNA hairpins, DNA/RNA hybrids, RNA (e.g. mRNA or miRNA) and RNA hairpins. Generally, a target molecule can be a naturally occurring molecule or a cDNA of a naturally occurring molecule or the complement of said cDNA. In other embodiments, a target molecule can be modified, e.g., by mutation or chemical reaction. In some embodiments, a target molecule can be synthetic or recombinant.

In some embodiments, an analyte can be an analyte comprising at least one post-translational modification, e.g., phosphorylations and/or glycosylations.

A target molecule or an analyte can be part of a sample that contains other components or can be the sole or major component of the sample. A target molecule or an analyte can be a component of a whole cell, tissue or body fluid, a cell or tissue extract, a fractionated lysate thereof or a substantially purified molecule. The target molecule can be present in solution or attached to a solid substrate, including, for example, to a solid surface such as a chip, microarray, bead or a blotting membrane. Also the target molecule or analyte can have either a known or unknown structure or sequence.

Sample

The methods, detection reagents and kits described herein can be used to analyze a sample from any sources, e.g., but not limited to biological samples (e.g., collected from organisms, animals or subjects), environmental samples, food, food byproduct, soil, archaeological samples, extraterrestrial samples, or any combinations thereof.

In some embodiments, the term "sample" refers to a biological sample. The term "biological sample" as used herein denotes a sample taken or isolated from a biological organism, e.g., tissue cell culture supernatant, cell lysate, a tissue sample (e.g., biopsy), a homogenate of a tissue sample from a subject or a fluid sample from a subject. Exemplary biological samples include, but are not limited to, blood, sputum, urine, cerebrospinal fluid, urine, sweat, mucus, nasal discharge, vaginal fluids, spinal fluid, pleural fluid, nipple aspirates, lymph fluid, the external sections of the skin, respiratory, intestinal, and genitourinary tracts, tears, saliva, milk, feces, sperm, cells or cell cultures, serum, leukocyte fractions, smears, tissue samples of all kinds, plants and parts of plants, microorganisms (such as bacteria), viruses (such as cytomegalo virus, HIV, hepatitis B, hepatitis C, hepatitis δ virus), yeasts, embryos, fungi, cell-free sample material, etc. The term also includes both a mixture of the above-mentioned samples such as fungus-infected plants or whole human blood containing mycobacteria as well as food samples that contain free or bound nucleic acids, or proteins, or cells containing nucleic acids or proteins, environmental samples which contain free or bound nucleic acids, or proteins, or cells containing nucleic acids or proteins. The term "biological sample" also includes untreated or pretreated (or pre-processed) biological samples.

A "biological sample" can contain cells from subject, but the term can also refer to non-cellular biological material, such as non-cellular fractions of blood, saliva, or urine, that can be used to measure gene expression levels. In some embodiments, the sample is from a resection, bronchoscopic biopsy, or core needle biopsy of a primary or metastatic tumor, or a cell block from pleural fluid. In addition, fine needle aspirate samples can be used. Samples can be either paraffin-embedded or frozen tissue. In some embodiments, a biological sample can comprise a biopsy, a surgically removed tissue, a swap, or any combinations thereof.

The sample can be obtained by removing a sample of cells from a subject, but can also be accomplished by using previously isolated cells (e.g. isolated by another person). In addition, the biological sample can be freshly collected or a previously collected sample. Furthermore, the biological sample can be utilized for the detection of the presence and/or quantitative level of a biomolecule of interest. Representative target analytes include, but are not limited to nucleic acids, proteins, and derivatives and fragments thereof.

In some embodiments, the biological sample is an untreated biological sample. As used herein, the phrase "untreated biological sample" refers to a biological sample that has not had any prior sample pre-treatment except for dilution and/or suspension in a solution. Exemplary methods for treating a biological sample include, but are not limited to, centrifugation, filtration, sonication, homogenization, heating, freezing and thawing, and any combinations thereof.

In accordance with some embodiments of various aspects described herein, a biological sample can be pre-processed, as described earlier, before employing the detection reagents and the methods described herein. In some embodiments, the biological sample can be filtered before isolating a cellular material according to the methods, apparatus and kits described herein.

In some embodiments, the biological sample can be treated with a chemical and/or biological reagent. Chemical and/or biological reagents can be employed to protect and/or maintain the stability of the sample or target analytes during processing. In addition, or alternatively, chemical and/or biological reagents can be employed to release or expose target analytes from other components of the sample. One exemplary reagent is a protease inhibitor, which is generally used to protect or maintain the stability of the target analytes during processing.

In some embodiments, the term "sample" as used herein can refer to an environmental sample (including, but not limited to, air, agricultural (e.g., but not limited to hydro-farms or hydroponic samples), pond, water, wastewater, and soil samples); biological warfare agent samples; research samples including extracellular fluids. In some embodiments, an environmental sample can comprise a sample collected from a working surface of an equipment or machine (e.g., but not limited to, food or pharmaceutical product processing equipment or machine), a device (e.g., but not limited to, biomedical devices, implantation devices, fluid delivery devices such as a tubing, and/or a catheter), and/or a building or dwellings (e.g., but not limited to, food processing plants, pharmaceutical manufacturing plants, hospitals, and/or clinics).

In some embodiments, a sample can comprise food (e.g., solid and/or fluid food as well as processed food) and/or food byproduct. For example, the methods, detection reagents and kits described herein can be used to detect an analyte, e.g., a particular nutrient, in food and/or food byproduct, e.g., but not limited to, meat, milk, yoghurt, bread, starch-based products, vegetables, and any combinations thereof. In some embodiments, the methods, detection reagents and kits described herein can be used to detect a contaminant, e.g., bacteria, fungus, spores, molds, and/or viruses, in food and/or food byproduct.

In some embodiments, a sample can comprise a pharmaceutical product (e.g., but not limited to pills, tablets, gel capsules, syrups, vaccines, liquids, sprays, and any combinations thereof). For example, the methods, detection reagents and kits described herein can be used to detect the presence and/or measure the level of a particular active agent present in a pharmaceutical product. In some embodiments, the methods, detection reagents and kits described herein can be used to detect a contaminant, e.g., bacteria, fungus, spores, molds, and/or viruses, in a pharmaceutical product.

In some embodiments, a sample can comprise an archaeological sample. In some embodiments, an archaeological sample can be obtained or collected from artifacts, architecture, biofacts (or ecofact, e.g., an object found at an archaeological site), cultural landscapes, and any combinations thereof.

In some embodiments, a sample can comprise an extraterrestrial sample. For example, an extraterrestrial sample can be any object or specimen (e.g., rock, meteorite, and/or environmental samples) obtained or collected from outer space or universe, and/or planets beyond the planet Earth, e.g., the moon, other planets (e.g., but not limited to, Mars, and/or Jupiter) and/or non-stellar objects.

Applications of the Detection Reagents

The detection reagents, compositions, methods and kits described herein can be used for diagnostic, prognostic therapeutic and screening purposes. The inventions described herein provide the advantage that many different target analytes can be analyzed at one time from a single sample using the methods described herein. This allows, for example, for several diagnostic tests to be performed on one sample.

When the probe reagent is a nucleic acid, the methods described herein can discriminate between nucleotide sequences. The difference between the target nucleotide sequences can be, for example, a single nucleic acid base difference, a nucleic acid deletion, a nucleic acid insertion, or rearrangement. Such sequence differences involving more than one base can also be detected. In some embodiments, the oligonucleotide probe sets have substantially the same length so that they hybridize to target nucleotide sequences at substantially similar hybridization conditions. As a result, the process described herein is able to detect various kinds of diseases or disorders, e.g., but not limited to, infectious diseases, genetic diseases, and cancer.

Without wishing to be bound, the detection reagents, compositions, methods and kits described herein can also be used for environmental monitoring, forensics, and food science. Examples of genetic analyses that can be performed on nucleic acids include e.g., SNP detection, STR detection, RNA expression analysis, promoter methylation, gene expression, virus detection, viral subtyping and drug resistance.

In the area of environmental monitoring, some embodiments of various aspects described herein can be used for detection, identification, and monitoring of pathogenic and indigenous microorganisms in natural and engineered ecosystems and microcosms such as in municipal waste water purification systems and water reservoirs or in polluted areas undergoing bioremediation. It can also be used to detect plasmids containing genes that can metabolize xenobiotics, to monitor specific target microorganisms in population dynamic studies, or either to detect, identify, or monitor genetically modified microorganisms in the environment and in industrial plants.

Some embodiments of various aspects described herein can also be used in a variety of forensic areas, including for human identification for military personnel and criminal investigation, paternity testing and family relation analysis, HLA compatibility typing, and screening blood, sperm, or transplantation organs for contamination.

In the food and feed industry, some embodiments of various aspects described herein have a wide variety of applications. For example, it can be used for identification and characterization of production organisms such as yeast for production of beer, wine, cheese, yogurt, bread, etc. Another area of use is related to the quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections.

In some embodiments, the methods, detection reagents and kits described herein can be used to detect the presence and/or measure the level of a particular active agent present in a pharmaceutical product. In some embodiments, the methods, detection reagents and kits described herein can be used to detect a contaminant, e.g., bacteria, fungus, spores, molds, and/or viruses, in a pharmaceutical product.

In some embodiments, the methods, detection reagents and kits described herein can be used to detect the presence and/or measure the level of an analyte of interest present in an archaeological sample, e.g., obtained or collected from artifacts, architecture, biofacts (or ecofact, e.g., an object found at an archaeological site), cultural landscapes, and any combinations thereof.

In some embodiments, the methods, detection reagents and kits described herein can be used to detect the presence and/or measure the level of an analyte of interest present in an extraterrestrial sample, e.g., any object or specimen (e.g., rock, meteorite, and/or environmental samples) obtained or collected from outer space or universe, and/or planets beyond the planet Earth, e.g., the moon, other planets (e.g., but not limited to, Mars, and/or Jupiter) and/or non-stellar objects. For example, the methods, detection reagents, and kits described herein can be used to analyze the composition of an extratrerresterial sample or specimen, e.g., a rock specimen, a water sample, and/or an air sample.

In some embodiments, the detection reagents and methods described herein can be used to detect and/or identify analytes comprising a post-translation modification, e.g., phosphorylation or glycosylation. As such, in some embodiments, the detection reagents and methods described herein can differentiate between multiple different glycosylation forms of recombinant therapeutic proteins Immunohistochemistry: Some embodiments of various aspects described herein can be used to perform antibody-based staining of cell or tissues for microscopic evaluation. This can involve either unfixed or unpermeabilized samples examined for surface or extracellular antigens, or permeabilized samples wherein intracellular antigens are also probed. While very common, immunohistochemistry is typically limited to probing with a small set of antibodies at a time (due to the limitation of available optical colors), and multiple staining cycles are generally avoided, since the stripping of the preceding cycle's antibodies can damage the sample. Some embodiments of the detection reagents comprising antibodies as probe reagents and nucleic acid labels can allow for many antibodies to be used concurrently, which saves time and sample material, extract more data, and demand less prior knowledge of the sample. In some embodiments, without wishing to be bound by theory, when a subset of the probed antigens can overlap spatially, the detection reagents with a plurality of contiguous pre-determined subsequences (e.g., each pre-determined subsequences contain one nucleotide, as shown in FIG. 3) can be used.

In-situ hybridization: Fluorescence in-situ hybridization (FISH) is a technique for detecting (and/or quantifying) the presence of certain cellular DNA or RNA (often ribosomal RNA). As with other fluorescence-based techniques, FISH is limited to the number of colors available to the microscopy. Using some embodiments of the detection reagents and/or methods described herein, the cells can be probed for many sequences simultaneously, thus allowing the user to save time and sample material, extract more data, and demand less prior knowledge of the sample.

Expression profiling: Nucleic-acid probe reagents of the detection reagents can target messenger RNA or micro RNA and provide information on the RNA-level expression state of the cell. Using some embodiments of the detection reagents and/or methods described herein, the assay can capture and probe numerous mRNA and/or miRNA at once, reducing and/or eliminating potentially harmful stripping steps.

Western blots: Western blots are protein assays wherein proteins are separated electrophoretically, transferred to a membrane and stained. In many cases, the staining is done using one or a few antibodies in order to detect the corresponding antigens in the blot. By using some embodiments of the detection reagents and/or methods described herein, the blot can be simultaneously probed using a large number of antibodies without antibody-stripping steps. This can allow one blot to provide significantly more information than the conventional Western blots where one antibody is usually probed at a time and can require antibody stripping for the next antibody probing, thereby saving sample material and time.

Diagnostic/Prognostic Methods: The present methods can be applied to the analysis of biological samples obtained or derived from a patient so as to determine whether a diseased cell type is present in the sample and/or to stage the disease.

In some embodiments, the methods described herein are used in the diagnosis of a condition. As used herein the term "diagnose" or "diagnosis" of a condition includes predicting or diagnosing the condition, determining predisposition to the condition, monitoring treatment of the condition, diagnosing a therapeutic response of the disease, and prognosis of the condition, condition progression, and response to particular treatment of the condition. For example, a blood sample can be assayed according to any of the methods described herein to determine the presence and/or quantity of markers of a cancerous cell type in the sample, thereby diagnosing or staging the cancer.

In some embodiments, the detection reagents and methods described herein can be directly used as contrast agents for in vivo or in situ diagnosis, in which detection reagents are administered to a subject, either by oral administration or local injection. The probe reagents of the detection reagents can bind to the target analytes, e.g., biomarkers for specific diseases or disorders, and detection of the nucleic acid labels using the methods described herein can then locate the target analytes. In some embodiments, the detection reagents and methods described herein can be used to locate microscopic tumors in a subject, where other conventional methods are not sensitive enough to detect such microscopic tumors.

Cancers which can be detected by some embodiments of the process described herein generally involve oncogenes, tumor suppressor genes, or genes involved in DNA amplification, replication, recombination, or repair. Examples of these include: BRCA1 gene, p53 gene, APC gene, Her2/Neu amplification, Bcr/Abl, K-ras gene, and human papillomavirus Types 16 and 18. Some embodiments of various aspects can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

Genetic diseases can also be detected by some embodiments of the process described herein. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

Alternatively, the methods described herein can be used to diagnose pathogen infections, for example infections by intracellular bacteria and viruses, by determining the presence and/or quantity of markers of bacterium or virus, respectively, in the sample.

A wide variety of infectious diseases can be detected by some embodiments of the process described herein. Typically, these are caused by bacterial, viral, parasite, and fungal infectious agents. The resistance of various infectious agents to drugs can also be determined using some embodiments of various aspects described herein.

Bacterial infectious agents which can be detected by some embodiments of various aspects described herein can include *Escherichia coli, Salmonella, Shigella, Klebsiella, Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia*, B-Hemolytic strep., *Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia*, and *Acitnomycetes*.

Fungal infectious agents which can be detected by some embodiments of various aspects described herein can include *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis*, and *Maduromycosis*.

Viral infectious agents which can be detected by some embodiments of various aspects described herein can include human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by some embodiments of various aspects described herein can include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidum, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis,* trematodes, *Diphyllobothrium latum, Taenia* spp., *Pneumocystis carinii*, and *Necator americanis*.

In some embodiments, contacting a biological sample with the detection reagents described herein immune-staining, in-situ hybridization or a combination, can be used for the purpose of detecting and identifying pathogens in biological samples. In such embodiments, for example, surface or intracellular antigens, DNA, ribosomal RNA and/or messenger RNA can be detected with some embodiments of the detection reagents and methods described herein. Detection reagents and methods described herein can be especially useful in this context since a) which pathogen may be in the sample is not known in advance, and b) each pathogen cell should respond to one or few of the probes, facilitating the detection reagent and nucleic acid label design.

Some embodiments of various aspects described herein can also be used for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with some embodiments of various aspects described herein.

Thus, the target molecules detected using the compositions and methods described herein can be either patient markers (such as a cancer marker) or markers of infection with a foreign agent, such as bacterial or viral markers.

Because of the quantitative nature of detection reagents, the compositions and methods described herein can be used to quantitate target molecules whose abundance is indicative of a biological state or disease condition, for example, blood markers that are upregulated or downregulated as a result of a disease state.

In addition, the compositions and methods described herein can be used to provide prognostic information that assists in determining a course of treatment for a patient. For example, the amount of a particular marker for a tumor can be accurately quantified from even a small sample from a patient. For certain diseases like breast cancer, overexpression of certain genes, such as Her2-neu, indicate a more aggressive course of treatment will be needed.

In some embodiments, the compositions and methods described herein can be administered to a subject for in vivo diagnosis and/or monitoring of a disease or disorder. Specific devices or methods known in the art for the in vivo detection of fluorescence, e.g., from fluorophores or fluorescent proteins, include, but are not limited to, in vivo near-infrared fluorescence (see, e.g., Frangioni, Curr. Opin. Chem. Biol, 7:626-634 (2003)), the Maestro™ in vivo fluorescence imaging system (Cambridge Research & Instrumentation, Inc.; Woburn, Mass.), in vivo fluorescence imaging using a flying-spot scanner (see, e.g., Ramanujam et al, IEEE Transactions on Biomedical Engineering, 48:1034-1041 (2001), and the like. Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes.

Any device or method known in the art for detecting the radioactive emissions of radionuclides in a subject is suitable for use in various aspects described herein. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled aggregate. Positron emission tomography (PET) is another suitable technique for detecting radiation in a subject.

Analysis of Pathology Samples: RNA extracted from formaldehyde- or paraformaldehyde-fixed paraffin-embedded tissue samples is typically poor in quality (fragmented) and low in yield. This makes gene expression analysis of low-expressing genes in histology samples or archival pathology tissues extremely difficult and often completely infeasible. The detection reagents and methods described herein can fill this unmet need by allowing the analysis of very small quantities of low-quality total RNA.

To use detection reagents in such an application, total RNA can be extracted from formaldehyde- or paraformaldehyde-fixed paraffin-embedded tissue samples (or similar) using commercially available kits such as RecoverAll Total Nucleic Acid Isolation Kit (Ambion) following manufacturer's protocols. RNA in such samples is frequently degraded to small fragments (200 to 500 nucleotides in length), and many paraffin-embedded histology samples only yield tens of nanograms of total RNA. Small amounts (5 to 100 ng) of this fragmented total RNA can be used directly as target analyte upon contact with the detection reagents described herein, using the methods described herein described herein.

Screening Methods: The methods described herein can be used, among other things, for determining the effect of a perturbation, including chemical compounds, mutations, temperature changes, growth hormones, growth factors, disease, or a change in culture conditions, on various target molecules, thereby identifying target molecules whose presence, absence or levels are indicative of particular biological states. In one embodiment, some aspects described herein can be used to elucidate and discover components and pathways of disease states. For example, the comparison of quantities of target molecules present in a disease tissue with "normal" tissue allows the elucidation of important target molecules involved in the disease, thereby identifying targets for the discovery/screening of new drug candidates that can be used to treat disease.

Targeted Delivery Vehicles: In some embodiments, the therapeutic and/or diagnostic agent can be encapsulated within the particles that provide conjugation sites for the probe reagents and nucleic acid labels. In such embodiments, the detection reagents and methods described herein can be used to deliver a therapeutic and/or diagnostic agent to cells where the probe reagents of the detection reagents bind. Nucleic acid labels of the detection reagents can be detected to monitor the location of drug administration.

Cell Lineage Tracking: In some embodiments, the detection reagents described herein can be used to track cell lineage, e.g., in culture or in vivo. For example, the probe reagents of the detection reagents can bind to live cells of interest, allowing labeling and/or tracking of individual cell differentiation. Examples of such application include, but are not limited to, lineage tracking in stem cell differentiation, and lineage determination of dendritic cells and/or white blood cells. In some embodiments, these cells after lineage determination can be further used accordingly.

Kits Comprising Detection Reagents

Kits for various assays are also provided herein. In some embodiments, a kit can comprise: (a) a plurality of nucleic acid labels of the detection reagents described herein; and (b) at least one coupling reagent required to conjugate the nucleic acid labels to probe reagents of interest. In such embodiments, users can attach the provided nucleic acid labels to their probe reagents of interest to form their own detection reagents described herein. Examples of the coupling reagent required for nucleic acid label-probe reagent conjugation can include any reagents that are generally used to perform any of the conjugation methods described herein, e.g., biotin and avidin-like molecules such as streptavidin or neutravidin. However, in alternative embodiments, the kit can comprise a plurality of the detection reagents described herein that are ready for use and thus no nucleic acid label-probe reagent conjugation steps are required to be performed by users prior to use.

In some embodiments, the kit can further comprise at least one reagent, e.g., used in a readout method described herein. For example, if the readout method is sequencing-based, the kit can further comprise at least one agent used in sequencing-based readout. Alternatively, if the readout method is hybridization-based, the kit can further comprise at least one set of decoder probes complementary to at least a portion of subsequences of the detection reagents, wherein each subpopulation of the decoder probes comprises a different detectable label, each different detectable label producing a different signal signature.

Accordingly, in some embodiments, a kit for hybridization-based readout can comprise: (a) a plurality of nucleic acid labels of the detection reagents described herein; (b) at least one reagent required to conjugate the nucleic acid labels to probe reagents of interest; and (c) at least one set of decoder probes complementary to at least a portion of subsequences of the detection reagents, wherein each subpopulation of the decoder probes comprises a different detectable label, each different detectable label producing a different signal signature. In some embodiments, the kit can further comprise at least one reagent, e.g., used in the readout method.

In alternative embodiments, a kit for hybridization-based readout can comprise: (a) a plurality of the detection reagents described herein; (b) at least one set of decoder probes complementary to at least a portion of subsequences of the detection reagents, wherein each subpopulation of the decoder probes comprises a different detectable label, each different detectable label producing a different signal signature; and (c) at least one reagent.

In any embodiments of the kit described herein, the plurality of the detection reagents can include one or more different kinds of the detection reagents. In some embodiments, it is desirable to provide different kinds of the detection reagents (e.g., different types of probe reagents, target binding domains, and/or target analytes) in separate containers. The number of different kinds of the detection reagents provided in the kit can be tailored for each application described herein. In some embodiments, the kit can comprise at least 2, at least 3, at least 4, at least 5, at least 6 at least 7, at least 8, at least 9, at least 10, at least 20, at least 30, at least 40, at least 50, at least 60, at least 70, at least 80, at least 90, at least 100 or more different kinds of the detection reagents.

In any embodiments of the kit described herein, the kit can comprise a plurality of sets of decoder probes, e.g., e.g., 2, 3, 4, 5, 6, 7, 8, 9, 10 or more sets of decoder probes, wherein each set of decoder probes can target a different pre-determined sequence of the nucleic acid label. In each set of the decoder probes, there can be about 2, 3, 4, 5, 6, 7, 8, 9, 10 or more distinct populations of decoder probes. The decoder probes can be pre-labeled with at least one detectable label or unlabeled. In some embodiments where the decoder probes are not pre-labeled, the kit can further comprise one or more distinct detectable labels provided in separate containers for labeling the decoder probes. In some embodiments, the detectable label can be an optical label described herein.

Examples of a reagent, e.g., used in a readout method, can include, but are not limited to, a readout reagent, a wash buffer, a signal removal buffer, buffers for performing hybridization reactions, restriction endonucleases, nucleic acid ligases, and any combinations thereof.

In some embodiments, the detection reagents can be provided in a solution phase. In other embodiments, the detection reagents can be immobilized in a solid support or substrate.

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce.

Generally the substrate is flat (planar), although as will be appreciated by those in the art, other configurations of substrates may be used as well; for example, three dimensional configurations can be used, for example by embedding the detection reagents in a porous block of plastic that allows sample access to the detection reagents and using a confocal microscope for detection. In some embodiments, the detection reagents can be placed on the inside surface of a tube, for flow-through sample analysis to minimize sample volume. Preferred substrates include optical fiber bundles, and flat planar substrates such as glass, polystyrene and other plastics and acrylics. In some embodiment, the solid support or substrate can be a multi-well plate.

In addition to the above mentioned components, the kit can include informational material. The informational material can be descriptive, instructional, marketing or other material that relates to the methods described herein and/or the use of the aggregates for the methods described herein. For example, the informational material describes methods for administering the detection reagents to a subject, and/or includes instructions to label decoder probes with detectable labels provided therein and/or instructions to conjugate at least one nucleic acid label to a probe reagent. The kit can also include a delivery device.

In some embodiments, the informational material can include instructions to administer the formulation in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., an adult human. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments, the kit contains separate containers, dividers or compartments for each component and informational material. For example, each different component can be contained in a bottle, vial, or syringe, and the informational material can be contained in a plastic sleeve or packet. In other embodiments, the separate elements of the kit are contained within a single, undivided container. For example, the formulation is contained in a bottle, vial or syringe that has attached thereto the informational material in the form of a label.

In some embodiments, the kit includes a plurality, e.g., a pack, of individual containers, each containing one or more unit dosage forms of the composition comprising the detection reagents. For example, the kit includes a plurality of syringes, ampules, foil packets, or blister packs, each containing a single unit dose of the formulation. The containers of the kits can be air tight and/or waterproof.

Embodiments of various aspects described herein can be illustrated by the following numbered paragraphs.

1. A method for detecting a plurality of analytes in a sample, comprising:
 a. contacting the sample with a composition comprising a plurality of detection reagents, wherein each subpopulation of the detection reagents targets at least one different analyte, and wherein each detection reagent comprises:
  at least one probe reagent targeting an analyte and at least one nucleic acid label comprising one or a plurality of pre-determined subsequences, wherein said at least one probe reagent and said at least one nucleic acid label are conjugated together; and wherein at least a portion of said one or the plurality of pre-determined subsequences form an identifier of said at least one probe reagent; and
 b. detecting in a temporally-sequential manner said one or the plurality of the pre-determined subsequences of said detection reagent, wherein said detection of the subsequences each generates a signal signature corresponding to said subsequence, and wherein a temporal order of the signal signatures corresponding to said one or the plurality of the subsequences of said detection reagent identifies a subpopulation of the detection reagents.

2. The method of paragraph 1, wherein said each subpopulation of the detection reagents targets a set of analytes (e.g., at least two analytes or more).

3. The method of paragraph 1 or 2, wherein the temporal order of the signal signatures corresponding to said one or the plurality of the subsequences of said detection reagent is unique for each subpopulation of the detection reagents.

4. The method of any of paragraphs 1-3, wherein said detection reagents are present in a soluble phase.

5. The method of any of paragraphs 1-4, further comprising processing said sample before said contacting with said plurality of detection reagents.

6. The method of any of paragraphs 1-5, further comprising removing any unbound detection reagents before the detecting step (b).

7. The method of any of paragraphs 1-6, further comprising comparing said temporal order of the signal signatures with different identifiers of said at least one probe reagent, wherein an agreement between the temporal order of the signal signatures and a particular identifier of said at least one probe reagent identifies the analyte in the sample.

8. The method of any of paragraphs 1-7, further comprising measuring the intensity of the signal signatures generated from each subpopulation of the detection reagents.

9. The method of paragraph 8, wherein the intensity of the signal signatures generated from each subpopulation of the detection reagents indicates an amount of the analyte.

10. The method of paragraph 8 or 9, wherein the intensity of the signal signatures generated from each subpopulation of the detection reagents is used in identification of the subpopulation of the detection reagents.

11. The method of any of paragraphs 1-10, wherein said detecting of step (b) comprises sequencing.

12. The method of paragraph 11, wherein said sequencing is performed via ligation, hybridization, synthesis, amplification, or single-base extension.

13. The method of any of paragraphs 1-12 wherein said detecting of step (b) comprises hybridizing a decoder probe with said subsequence, wherein said decoder probe comprises a detectable label.

14. The method of any of paragraphs 1-13, wherein said detecting of step (b) comprises:
 a. hybridizing a set of decoder probes with a subsequence of the detection reagents, wherein each subpopulation of the decoder probes comprises a detectable label, each detectable label producing a signal signature;
 b. detecting said signal signature produced by the hybridization of said set of decoder probes;
 c. optionally removing said different signal signature produced by the hybridization of said set of decoder probes; and
 d. repeating steps (a) through (c) for other subsequences of said detection reagents, thereby producing a temporal order of the signal signatures corresponding to said each detection reagent.

15. The method of paragraph 14, wherein said each subpopulation of the decoder probes comprises a different detectable label, each different detectable label producing a different signal signature.

16. The method of paragraph 14 or 15, wherein said each subpopulation of the decoder probes is at least partially or completely complementary to said subsequence of the detection reagents.

17. The method of any of paragraphs 14-16, wherein at least two or more subpopulations of the decoder probes are at least partially or completely complementary to the same subsequence of the detection reagents.

18. The method of any of paragraphs 14-17, wherein said removing step is performed by washing, heating, photobleaching, displacement, cleavage, enzymatic digestion, quenching, chemical degradation, bleaching, oxidation or any combinations thereof.

19. The method of any of paragraphs 14-18, wherein said detectable label comprises or is an optical label selected from the group consisting of a small-molecule dye, a fluorescent molecule, a fluorescent protein, a quantum dot, Raman label, a chromophore, and any combinations thereof.

20. The method of any of paragraphs 14-19, wherein said detectable label comprises or is a colorimetric reagent.

21. The method of any of paragraphs 14-20, wherein said detectable label comprises or is a Raman label.

22. The method of any of paragraphs 1-21, wherein said signal signatures comprise or are optical signatures.

23. The method of paragraph 22, wherein said optical signatures comprise signatures of fluorescent color, visible light, no-color, Raman label, or any combinations thereof.

24. The method of paragraph 22, wherein said optical signatures comprise signatures of one or more fluorescent colors, one or more visible lights, one or more no-colors, one or more Raman labels, or any combinations thereof.

25. The method of any of paragraphs 22-24, wherein said optical signatures are detected by optical imaging or spectroscopy.

26. The method of any of paragraphs 1-25, wherein said analytes are selected from the group consisting of antigens, receptors, proteins, peptides, sugars, glycoproteins, peptidoglycans, lipids, nucleic acids, oligonucleotides, cells, viruses, and any combinations thereof.

27. The method of any of paragraphs 1-26, wherein said nucleic acids are selected from the group consisting of cellular DNA or RNA, messenger RNA, microRNA, ribosomal RNA, and any combinations thereof.

28. The method of any of paragraphs 1-27, wherein said sample is a protein sample immobilized on a solid support.

29. The method of paragraph 28, wherein the solid support is a blotting membrane.

30. The method of any of paragraphs 1-27, wherein said sample is a biological sample.

31. The method of paragraph 30, wherein said biological sample comprises one or more cells, one or more tissues, one or more fluids or any combinations thereof.

32. The method of paragraph 30 or 31, wherein said biological sample comprises blood, sputum, cerebrospinal fluid, urine, saliva, sperm, sweat, mucus, nasal discharge, vaginal fluids or any combinations thereof.

33. The method of any of paragraphs 30-31, wherein the said biological sample comprises a biopsy, a surgically removed tissue, a swap or any combinations thereof.

34. The method of paragraphs 1-27, wherein said sample comprises an environmental sample, food, food byproduct, soil, an archaeological sample, an extraterrestrial sample, or any combinations thereof.

35. The method of any of paragraphs 1-34, wherein said at least one probe reagent and said at least one nucleic acid label are conjugated together by at least one linker.

36. The method of paragraph 35, wherein said linker is a bond.

37. The method of paragraph 35 or 36, wherein said linker is a linker molecule.

38. The method of paragraph 37, wherein said linker molecule is a polymer, sugar, nucleic acid, peptide, protein, hydrocarbon, lipid, polyethylene glycol, crosslinker, or any combinations thereof.

39. The method of any of paragraphs 35-38, wherein said linker is a particle.

40. The method of paragraph 39, wherein said particle is selected from a group consisting of a gold nanoparticle, a magnetic bead or nanoparticle, a polystyrene bead, a nanotube, a nanowire, a microparticle, and any combinations thereof.

41. The method of paragraph 40, wherein said particle is a nanoparticle.

42. The method of any of paragraphs 39-41, wherein said particle is modified.

43. The method of any of paragraphs 39-42, wherein said particle is coated with streptavidin or a derivative thereof.

44. The method of any of paragraphs 39-43, wherein said particle is modified with at least one functional group.

45. The method of paragraph 44, wherein said at least one functional group is selected from the group consisting of amine, carboxyl, hydroxyl, aldehyde, ketone, tosyl, silanol, chlorine, hydrazine, hydrazide, photoreactive groups, and any combinations thereof.

46. The method of any of paragraphs 35-45, wherein said linker is multivalent.

47. The method of paragraph 46, wherein when the multivalent linker is an avidin-like molecule, both the probe reagent and the nucleic acid label are biotinylated.

48. The method of any of paragraphs 1-47, wherein said at least one probe reagent is selected from the group consisting of a nucleic acid, an antibody or a portion thereof, an antibody-like molecule, an enzyme, a cell, an antigen, a small molecule, a protein, a peptide, a peptidomimetic, a sugar, a carbohydrate, a lipid, a glycan, a glycoprotein, an aptamer, and any combinations thereof.

49. The method of any of paragraphs 1-48, wherein said at least one probe reagent is modified.

50. The method of any of paragraphs 1-49, wherein said at least one probe reagent is biotinylated.

51. The method of any of paragraphs 1-50, wherein said at least one nucleic acid label is single-stranded, double-stranded, partially double-stranded, a hairpin, linear, circular, branched, a concatemer, or any combinations thereof.

52. The method of any of paragraphs 1-51, wherein said at least one nucleic acid label is modified.

53. The method of any of paragraphs 1-52, wherein said at least one nucleic acid label is designed for minimal cross-hybridization of bases with each other.

54. The method of any of paragraphs 1-53, wherein said at least one nucleic acid label is conjugated to at least one detectable molecule.

55. The method of paragraph 54, wherein said at least one detectable molecule is an optical molecule selected from the group consisting of a small-molecule dye, a fluorescent protein, a quantum dot, a Raman label, a chromophore, and any combinations thereof.

56. The method of any of paragraphs 1-55, wherein each of said plurality of the pre-determined subsequences comprises at least one base.

57. The method of any of paragraphs 1-56, wherein each of said plurality of the pre-determined subsequences comprises from 1 to 100 nucleobases.

58. The method of any of paragraphs 1-57, wherein said plurality of the pre-determined subsequences are conjugated together by at least one sequence linker.

59. The method of paragraph 58, wherein said sequence linker is a bond.

60. The method of any of paragraphs 58-59, wherein said sequence linker is a nucleotidic linker.

61. The method of paragraph 60, wherein said nucleotidic linker is single-stranded, double-stranded, partially double-stranded, a hairpin or any combinations thereof.

62. The method of paragraph 60 or 61, wherein said nucleotidic linker is at least one nucleotide long.

63. The method of any of paragraphs 1-62, wherein said detection reagent comprises one probe reagent and a plurality of nucleic acid labels.

64. The method of any of paragraphs 1-62, wherein said detection reagent comprises a plurality of probe reagents and a nucleic acid label.

65. The method of any of paragraphs 1-62, wherein said detection reagent comprises a plurality of probe reagents and a plurality of nucleic acid labels.

66. The method of any of paragraphs 1-65, wherein the method is adapted for use in immunofluorescence.

67. The method of any of paragraphs 1-66, wherein the method is adapted for use in immunohistochemistry.

68. The method of any of paragraphs 1-67, wherein the method is adapted for use in fluorescence in situ hybridization.

69. The method of any of paragraphs 1-68, wherein the method is adapted for use in western blot.

70. A detection reagent comprising at least one probe reagent and at least one nucleic acid label,
  wherein said at least one nucleic acid label comprises at least one pre-determined subsequence to be detected in a temporally-sequential manner;
  wherein said at least one pre-determined subsequence forms an identifier of said at least one probe reagent; and
  wherein said at least one probe reagent and said at least one nucleic acid label are conjugated together.

71. The detection reagent of paragraph 70, wherein the detection reagent is present in a soluble phase.

72. The detection reagent of paragraph 70 or 71, wherein said at least one probe reagent and said at least one nucleic acid label are conjugated together by at least one linker.

73. The detection reagent of paragraph 72, wherein said linker is a bond.

74. The detection reagent of paragraph 72 or 73, wherein said linker is a linker molecule.

75. The detection reagent of paragraph 74, wherein said linker molecule is a polymer, sugar, nucleic acid, peptide, protein, hydrocarbon, lipid, polyethelyne glycol, crosslinker or combination thereof.

76. The detection reagent of any of paragraphs 72-75, wherein said linker is a particle.

77. The detection reagent of paragraph 76, wherein said particle is selected from a group consisting of a gold nanoparticle, a magnetic bead or nanoparticle, a polystyrene bead, a nanotube, a nanowire, a microparticle, and any combinations thereof.

78. The detection reagent of paragraph 76 or 77, wherein said particle is a nanoparticle.

79. The detection reagent of any of paragraphs 76-78, wherein said particle is modified.

80. The detection reagent of any of paragraphs 76-79, wherein said particle is coated with streptavidin or a derivative thereof.

81. The detection reagent of any of paragraphs 76-80, wherein said particle is modified with at least one functional group.

82. The detection reagent of paragraph 81, wherein the at least one functional group is selected from the group consisting of amine, carboxyl, hydroxyl, aldehyde, ketone, tosyl, silanol, chlorine, hydrazine, hydrazide, photoreactive groups, and any combinations thereof.

83. The detection reagent of any of paragraphs 72-82, wherein said linker is multivalent.

84. The detection reagent of paragraph 83, wherein when the multivalent linker is an avidin-like molecule, both the probe reagent and the nucleic acid label are biotinylated.

85. The detection reagent of any of paragraphs 70-84, wherein said at least one probe reagent is selected from the group consisting of a nucleic acid, an antibody or a portion thereof, an antibody-like molecule, an enzyme, a cell, an antigen, a small molecule, a protein, a peptide, a peptidomimetic, a sugar, a carbohydrate, a lipid, a glycan, a glycoprotein, an aptamer, and any combinations thereof.

86. The detection reagent of any of paragraphs 70-85, wherein said at least one probe reagent is modified.

87. The detection reagent of any of paragraphs 70-86, wherein said at least one probe reagent is biotinylated.

88. The detection reagent of any of paragraphs 70-87, wherein said at least one nucleic acid label is single-stranded, double-stranded, partially double-stranded, a hairpin, linear, circular, branched, a concatemer, or any combinations thereof.

89. The detection reagent of any of paragraphs 70-88, wherein said at least one nucleic acid label is modified.

90. The detection reagent of any of paragraphs 70-89, wherein said at least one nucleic acid label is designed for minimal cross-hybridization of bases with each other.

91. The detection reagent of any of paragraphs 70-90, wherein said at least one nucleic acid label is conjugated to at least one detectable molecule.

92. The detection reagent of paragraph 91, wherein said at least one detectable molecule is an optical molecule selected from the group consisting of small-molecule dye, a fluorescent protein, a quantum dot, a Raman label, a chromophore, and any combinations thereof.

93. The detection reagent of any of paragraphs 70-92, wherein said at least one nucleic acid label comprises a plurality of pre-determined subsequences.

94. The detection reagent of any of paragraphs 70-93, wherein each of said plurality of predetermined subsequences comprises at least one base.

95. The detection reagent of any of paragraphs 70-94, wherein each of said plurality of predetermined subsequences comprises from 1 to 100 nucleobases.

96. The detection reagent of any of paragraphs 70-95, wherein said plurality of the pre-determined subsequences are conjugated together by at least one sequence linker.

97. The detection reagent of paragraph 96, wherein said sequence linker is a bond.

98. The detection reagent of any of paragraphs 96-97, wherein said sequence linker is a nucleotidic linker.

99. The detection reagent of paragraph 98, wherein said nucleotidic linker is single-stranded, double-stranded, partially double-stranded, a hairpin, or any combinations thereof.

100. The detection reagent of paragraph 98 or 99, wherein said nucleotidic linker is at least one nucleotide long.

101. The detection reagent of any of paragraphs 70-100, wherein said detection reagent comprises one probe reagent and a plurality of nucleic acid labels.

102. The detection reagent of any of paragraphs 70-101, wherein said detection reagent comprises a plurality of probe reagents and a nucleic acid label.

103. The detection reagent of any of paragraphs 70-102, wherein said detection reagent comprises a plurality of probe reagents and a plurality of nucleic acid labels.

104. The detection reagent of any of paragraphs 70-103, wherein the detection reagent is adapted for use in immunofluorescence.

105. The detection reagent of any of paragraphs 70-104, wherein the detection reagent is adapted for use in immunohistochemistry.

106. The detection reagent of any of paragraphs 70-105, wherein the detection reagent is adapted for use in fluorescence in situ hybridization.

107. The detection reagent of any of paragraphs 70-106, wherein the detection reagent is adapted for use in western blot.

108. A kit comprising:
  a. a plurality of the detection reagents of any of paragraphs 70-107; and
  b. at least one reagent.

109. The kit of paragraph 108, wherein the kit further comprises at least one set of decoder probes complementary to at least a portion of subsequences of the detection reagents, wherein each subpopulation of the decoder probes comprises a different detectable label, each different detectable label producing a different signal signature.

110. The kit of paragraph 108 or 109, wherein said detection reagents are present in a soluble phase.

111. The kit of any of paragraphs 108-110, wherein said detection reagents are immobilized in a multi-well plate.

112. The kit of any of paragraphs 108-111, wherein said at least one reagent is selected from the group consisting of a readout reagent, a wash buffer, a signal removal buffer, and any combinations thereof.

113. A kit comprising:
   a. a plurality of the nucleic acid labels of the detection reagents of any of paragraphs 70-107;
   b. at least one coupling agent that allows a user to conjugate the nucleic acid labels to the user's probe reagents of interest, thereby forming the detection reagents comprising the user's probe reagents of interest; and
   c. at least one reagent.

114. The kit of paragraph 113, wherein the kit further comprises at least one set of decoder probes complementary to at least a portion of subsequences of the detection reagents, wherein each subpopulation of the decoder probes comprises a different detectable label, each different detectable label producing a different signal signature.

115. The kit of paragraph 113 or 114, wherein the detection reagents comprising the user's probe reagents of interest are present in a soluble phase.

116. The kit of any of paragraphs 113-115, wherein the detection reagents comprising the user's probe reagents of interest are immobilized in a multi-well plate.

117. The kit of any of paragraphs 113-116, wherein said at least one reagent is selected from the group consisting of a readout reagent, a wash buffer, a signal removal buffer, and any combinations thereof.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not. Additionally, the term "comprising" or "comprises" includes "consisting essentially of" and "consisting of."

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages can mean±1%.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the term "identifier" generally refers to a unique expression to distinguish variations from one to another among a class of substances, items, or objects. In particular embodiments, the term "identifier" as used herein refers to association of a unique pre-determined subsequence to a specific probe reagent, thus conferring the presence and identity of the probe reagent when the pre-determined subsequence is detected.

The term "statistically significant" or "significantly" refers to statistical significance and generally means a two standard deviation (2SD) above or below a reference level. The term refers to statistical evidence that there is a difference. It is defined as the probability of making a decision to reject the null hypothesis when the null hypothesis is actually true. The decision is often made using the p-value.

As used herein, the term "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "substantially" means a proportion of at least about 90%, at least about 95%, at least about 98%, at least about 99% or more, or any integer between 90% and 100%. In some embodiments, the term "substantially" can include 100%.

The term "sphere" means a particle having an aspect ratio of at most 3:1. The term "aspect ratio" means the ratio of the longest axis of an object to the shortest axis of the object, where the axes are not necessarily perpendicular.

The term "rod" means a particle having a longest dimension of at most 5000 nm, and having an aspect ratio of from 3:1 to 20:1.

The term "prism" means a particle having at least two non-parallel faces connected by a common edge.

As used herein, the term "pharmaceutically acceptable carrier" refers to a pharmaceutically-acceptable material, composition or vehicle for administration of the detection reagents. Pharmaceutically acceptable carriers include any and all solvents, dispersion media, coatings, antibacterial and antifungal agents, isotonic and absorption delaying agents, and the like which are compatible with the activity of the detection reagents and are physiologically acceptable to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" are used interchangeably herein.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "therapeutic agent" refers to a biological or chemical agent used for treatment, curing, mitigating, or preventing deleterious conditions in a subject. The term "therapeutic agent" also includes substances and agents for combating a disease, condition, or disorder of a subject, and includes drugs, diagnostics, and instrumentation. "Therapeutic agent" also includes anything used in medical diagnosis, or in restoring, correcting, or modifying physiological functions. The terms "therapeutic agent" and "pharmaceutically active agent" are used interchangeably herein.

A therapeutic agent can be selected according to the treatment objective and biological action desired. Thus, a therapeutic agent can be selected from any class suitable for the therapeutic objective. Further, the therapeutic agent may be selected or arranged to provide therapeutic activity over a period of time.

Exemplary pharmaceutically active compound include, but are not limited to, those found in Harrison's Principles of Internal Medicine, 13th Edition, Eds. T. R. Harrison McGraw-Hill N.Y., NY; Physicians Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's The Pharmacological Basis of Therapeutics; and current edition of The Merck Index, the complete content of all of which are herein incorporated in its entirety.

Exemplary pharmaceutically active agents include, but are not limited to, steroids and nonsteroidal anti-inflammatory agents, antirestenotic drugs, antimicrobial agents, angiogenic factors, calcium channel blockers, thrombolytic agents, antihypertensive agents, anti-coagulants, antiarrhythmic agents, cardiac glycosides, and the like.

In some embodiments, the therapeutic agent is selected from the group consisting of salicylic acid and derivatives (aspirin), para-aminophenol and derivatives (acetaminophen), arylpropionic acids (ibuprofen), corticosteroids, histamine receptor antagonists and bradykinin receptor antagonists, leukotriene receptor antagonists, prostaglandin receptor antagonists, platelet activating factor receptor antagonists, sulfonamides, trimethoprim-sulfamethoxazole, quinolones, penicillins, cephalosporin, basic fibroblast growth factor (FGF), acidic fibroblast growth factor, vascular endothelial growth factor, angiogenic transforming growth factor alpha and beta, tumor necrosis factor, angiopoietin, platelet-derived growth factor, dihydropyridines (e.g., nifedipine, benzothiazepines such as dilitazem, and phenylalkylamines such as verapamil), urokinase plasminogen activator, urokinase, streptokinase, angiotensin converting enzyme (ACE) inhibitors, spironolactone, tissue plasminogen activator (tPA), diuretics, thiazides, antiadrenergic agents, clonidine, propanolol, angiotensin-converting enzyme inhibitors, captopril, angiotensin receptor antagonists, losartan, calcium channel antagonists, nifedine, heparin, warfarin, hirudin, tick anti-coagulant peptide, and low molecular weight heparins such as enoxaparin, lidocaine, procainamide, encainide, flecanide, beta adrenergic blockers, propranolol, amiodarone, verpamil, diltiazem, nickel chloride, cardiac glycosides, angiotensin converting enzyme inhibitors, angiotensin receptor antagonists, nitrovasodilators, hypolipidemic agents (e.g., nicotinic acid, probucol, etc.), bile acid-binding resins (e.g., cholestyramine, and fibric acid derivatives e.g., clofibrate), HMG CoA reductase inhibitors, HMG CoA synthase inhibitors, squalene synthase inhibitors, squalene epoxidase inhibitors, statins (e.g., lovastatin, cerivastatin, fluvastatin, pravastatin, simvaststin, etc.), anti-psychotics, SSRIs, antiseizure medication, contraceptives, systemic and local analgesics (chronic pain, bone growth/remodeling factors (osteoblast/osteoclast recruiting and stimulating factors), neurotransmitters (L-DOPA, Dopamine, neuropeptides), emphysema drugs, TGF-beta), rapamycin, naloxone, paclitaxel, amphotericin, Dexamethasone, flutamide, vancomycin, phenobarbital, cimetidine, atenolol, aminoglycosides, hormones (e.g., thyrotropin-releasing hormone, p-nitrophenyl beta-cellopentaosideand luteinizing hormone-releasing hormone), vincristine, amiloride, digoxin, morphine, procainamide, quinidine, quinine, ranitidine, triamterene, trimethoprim, vancomycin, aminoglycosides, and penicillin, and pharmaceutically acceptable salts thereof.

As used herein, the term "fluorescent color" refers to a color emitted by any fluorophore (e.g., fluorescent dye, fluorescent particles such as quantum dots, and/or fluorescent proteins) upon light excitation and/or electromagnetic radiation. Fluorescent dye as disclosed herein refers to a dye which exhibits energy and is visible under illumination at a predefined wavelength. Numerous fluorescent molecules are commercially available and can be adapted for use in the methods, detection reagents and kits as disclosed herein, and include those from Molecular Probes, Sigma and similar other commercial sources. In some embodiments, a "fluorescent color" can be produced by phosphorescence. In some embodiments, a "fluorescent color" can be produced by luminescence (including bioluminescence).

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Figure 8B:
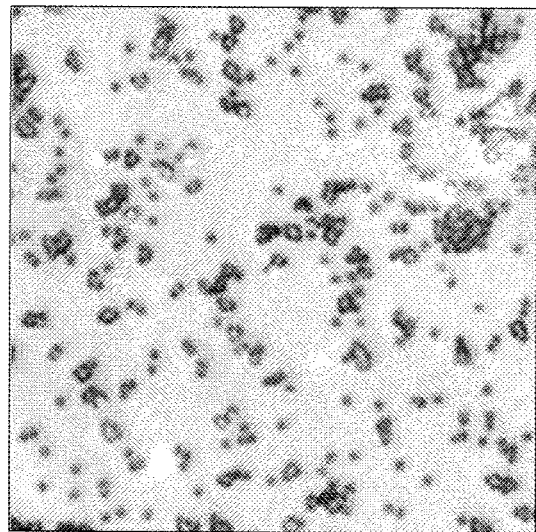
FIGS. 8A-8B show the readout images of DYNA-BEADS® beads (1 μm in size) localized on a sample using an exemplary hybridization-based detection method. Each bead was conjugated to one of 6 nucleic acid labels, which in turn hybridized with a different set of decoder probes conjugated to either a green, red or blank optical label during each readout stage (FIG. 8A: Readout stage 1.
Figure 8A:
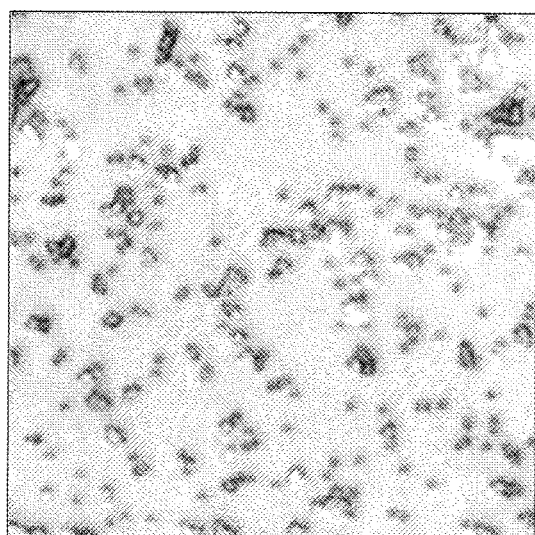

Example 1: Exemplary Hybridization-Based Detection Methods of Detection Reagents A solution suspension of streptavidin-coated Dynabeads (of about 1 μm), each conjugated to one of six nucleic acid labels and a corresponding probe reagent specific for a target analyte, wherein each of the nucleic acid labels comprised at least one pre-determined subsequence, e.g., a first (e.g., A1, A2, and A3) and a second (B1, B2, and B3) pre-determined subsequence, was prepared. The nucleic acid labels can comprise a nucleic acid sequence of any length. In some embodiments, the nucleic acid labels can comprise at least 15 nucleotides, at least 20 nucleotides, at least 22 nucleotides, or at least 24 nucleotides. A sample containing multiple target analytes was contacted with the target analyte-specific Dynabeads, so that the Dynabeads would bind to the respective target analyte on the sample. Any unbound Dynabeads was then removed, e.g., by washing. In the first readout, a set of three decoder probes, each with a distinct sequence complementary to the first pre-determined subsequences (e.g., A1*, A2*, and A3*) and a corresponding optical label (e.g., selected from red, green or blank), was added to the sample with bound Dynabeads, and then imaged with fluorescent microscopy (FIG. 8A). The fluorescent signal was then removed, e.g., by photobleaching, from the previous stage before the next readout. In the second readout, a different set of three decoder probes, each with a distinct complementary sequence to the second pre-determined subsequences (e.g., B1*, B2*, B3*) and a corresponding optical label (e.g., selected from red, green blank), was added to the photobleached sample, and then imaged with fluorescent microscopy (FIG. 8B). The temporal sequence of the optical signatures obtained from each bead can then be analyzed to determine the identity of the probe and thus the presence of the corresponding target analyte on the sample. Based on the intensity and/or coverage of the optical signals, the amount of the target analyte can also be determined.

By way of example only, a biotinylated anti-*C. albicans* antibody (e.g., an commercially-available antibody from Pierce Antibodies PA1-27145) was conjugated with a plurality of different biotinylated nucleic acid labels (e.g., 8 different biotinylated SeqTag label sequences) using any conjugation methods known in the art. In one embodiment, the biotinylated anti-*C. albicans* antibody was conjugated with a plurality of different biotinylated nucleic acid labels (e.g., biotinylated SeqTag label sequences) using a streptavidin-like protein (e.g., Neutravidin) as a bridge. The SeqTag label sequences are shown in Table 5. The SeqTag label sequences can comprise at least about 24 nucleotides. In some embodiments, the SeqTag label sequences can comprise DNA, RNA or a combination thereof. Each conjugate was incubated with a sample comprising *C. albicans*, washed, and readout using any readout method as described herein, e.g., the displacement-hybridization method.

TABLE 5

DNA sequences of exemplary SeqTag labels

| SEQ ID NO: | SeqTag label | DNA Sequence |
|---|---|---|
| 59 | SeqTag 1 | 5'-Biotin-TTTCGCTTTCTGTAATGGAGTGGA-3' |
| 60 | SeqTag 2 | 5'-Biotin-TTTCGCTTTAGCCTAAGTGAAATC-3' |
| 61 | SeqTag 3 | 5'-Biotin-TTTCGCTTTTTTGGGGAAAAGACA-3' |
| 62 | SeqTag 4 | 5'-Biotin-TTTCGCTTTTAGGCATTAGCATTG-3' |
| 63 | SeqTag 5 | 5'-Biotin-TTTCGCTTTGGAAGCACCTATTCC-3' |
| 64 | SeqTag 6 | 5'-Biotin-TTTCGCTTTCTGGAGAAAGGGCCA-3' |
| 65 | SeqTag 7 | 5'-Biotin-TTTCGCTTTCGGTTCCAAAGACAC-3' |
| 66 | SeqTag 8 | 5'-Biotin-TTTCGCTTTGAAGCCGGTTATAGC-3' |

Figure 9:
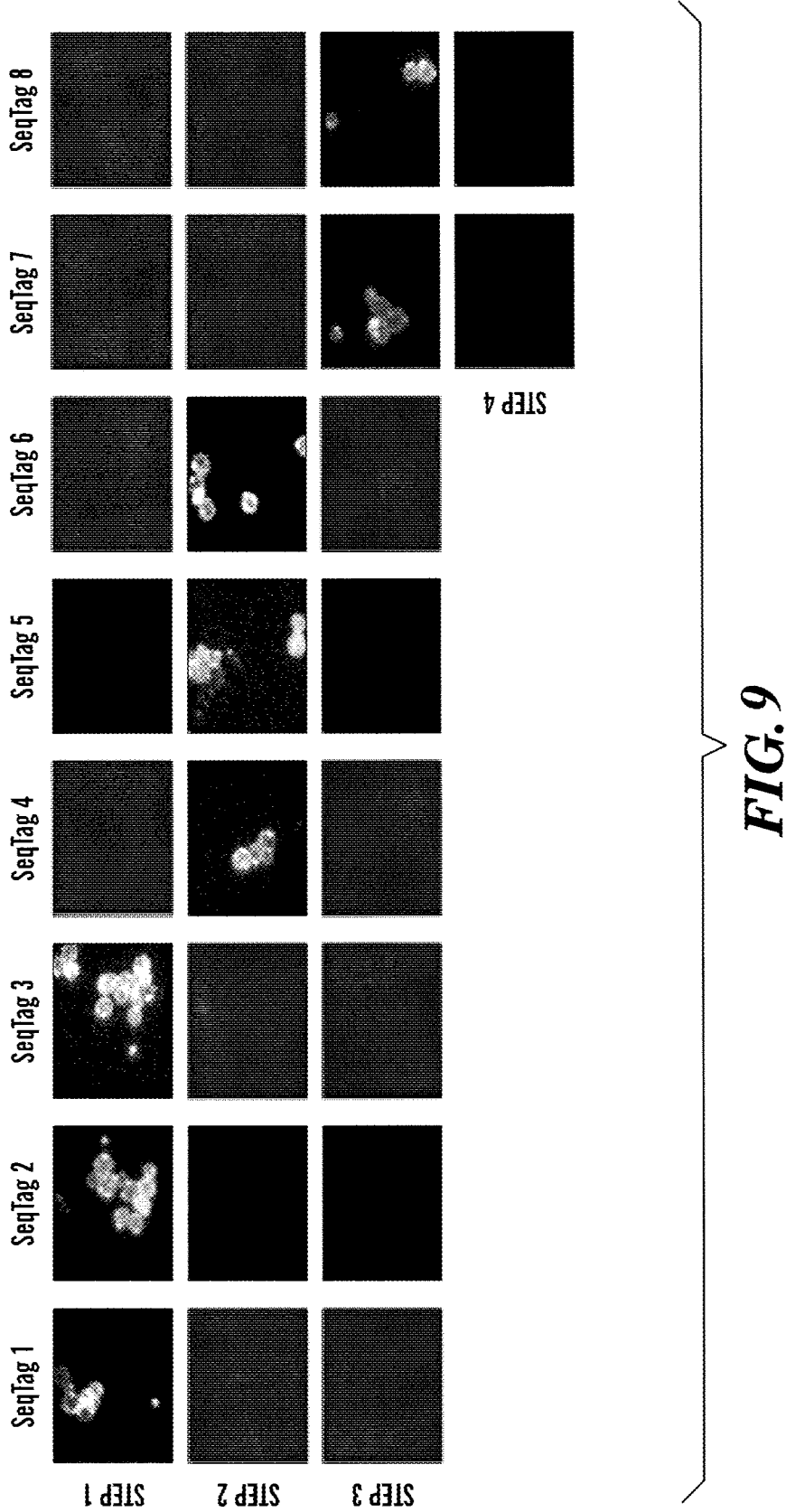
FIG. 9 is a set of images showing that each of the detection molecule constructs (SeqTag labels) properly stained the yeast and fluoresced in accordance with three pre-determined sets of decoder probes. SeqTag labels and oligonucleotide displacers were applied as follow.

During the displacement hybridization method, by way of example only, as shown in FIG. 9, the yeast was incubated in readout step 1 with a mixture of all three "set 1" decoder probes, followed by an incubation with a mixture of the "set 2" decoder probes and the "set 1 displacers" (which are nucleic acid sequences to remove "set 1" fluorescence), and similarly with appropriate sets of decoder probes and displacers for steps 3 and 4. The decoder probes can comprise a nucleic acid sequence (e.g., DNA, RNA or a combination thereof) and a detection label, e.g., at its 5' end. The nucleic acid sequence of the decoder probes can be of any length. In some embodiments, the decoder probes can comprise at least about 10 nucleotides, at least about 12 nucleotides, at least about 14 nucleotides, at least about 16 nucleotides, at least about 18 nucleotides, at least about 20 nucleotides or longer. Detection labels can be any art-recognized label described herein, e.g., fluorescent detection labels such as FAM, Cy3, and C5, or any labels described herein. Probe displacers, as described earlier, are nucleic acid sequences that are used to remove or displace the previous decoder probes hybridized to the nucleic acid labels (e.g., SeqTag labels) such that a different set of decoder probes can be added and hybridized to the nucleic acid labels. The probe displacers can have a nucleic acid sequence of any length. In some embodiments, the nucleic acid sequence of the probe displacers can be longer than that of the decoder probes. In some embodiments, the probe displacers can comprise at least about 12 nucleotides, at least about 14 nucleotides, at least about 16 nucleotides, at least about 18 nucleotides, at least about 20 nucleotides, at least about 21 nucleotides or longer. Tables 2 and 3 show DNA sequences of exemplary decoder probes (or readout probes) and probe displacers, respectively. As seen in FIG. 9, each biotinylated anti-*C albicans* antibody conjugated with a different SeqTag label sequence properly stained the yeast and fluorescenced only as designated by its SeqTag label with appropriate sets of decoder probes and probe displacer in each readout step.

TABLE 6

DNA sequences of exemplary decoder probes

| SEQ ID NO: | Readout probe | DNA Sequence |
| --- | --- | --- |
| 67 | Set 1 FAM | 5'-FAM-TTTTCCACTCCATTACAG-3' |
| 68 | Set 1 Cy3 | 5'-Cy3-TTTGATTTCACTTAGGCT-3' |
| 69 | Set 1 Cy5 | 5'-Cy5-TTTTGTCTTTTCCCCAAA-3' |
| 70 | Set 2 FAM | 5'-FAM-TTTCAATGCTAATGCCTA-3' |
| 71 | Set 2 Cy3 | 5'-Cy3-TTTGGAATAGGTGCTTCC-3' |
| 72 | Set 2 Cy5 | 5'-Cy5-TTTTGGCCCTTTCTCCAG-3' |
| 73 | Set 3 FAM | 5'-FAM-TTTGTGTCTTTGGAACCG-3' |
| 74 | Set 3 Cy3 | 5'-Cy3-TTTGCTATAACCGGCTTC-3' |

TABLE 7

DNA sequences of exemplary probe displacers

| SEQ ID NO: | Probe Displacer | DNA Sequence |
| --- | --- | --- |
| 75 | Set 1 FAM-Displacer | 5'-TCCACTCCATTACAGAAAGCG-3' |
| 76 | Set 1 Cy3-Displacer | 5'-GATTTCACTTAGGCTAAAGCG-3' |
| 77 | Set 1 Cy5-Displacer | 5'-TGTCTTTTCCCCAAAAAAGCG-3' |
| 78 | Set 2 FAM-Displacer | 5'-CAATGCTAATGCCTAAAGCG-3' |
| 79 | Set 2 Cy3-Displacer | 5'-GGAATAGGTGCTTCCAAAGCG-3' |
| 80 | Set 2 Cy5-Displacer | 5'-TGGCCCTTTCTCCAGAAAGCG-3' |
| 81 | Set 3 FAM-Displacer | 5'-TGTGTCTTTGGAACCGAAAGCG-3' |
| 82 | Set 3 Cy3-Displacer | 5'-GCTATAACCGGCTTCAAAGCG-3' |

Content of all patents and other publications identified herein is expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method for identifying an analyte at a location in a biological sample, comprising:

(a) binding a detection reagent to said analyte at said location of said biological sample, wherein said detection reagent comprises (i) a probe that binds to said analyte and (ii) a nucleic acid label that identifies said probe, and wherein said detection reagent is identifiable by a temporal order of signal signatures associated with said nucleic acid label;

SEQUENCE LISTING

<160> NUMBER OF SEQ ID NOS: 1

<210> SEQ ID NO 1
<211> LENGTH: 18
<212> TYPE: DNA
<213> ORGANISM: Artificial
<220> FEATURE:
<223> OTHER INFORMATION: PCR primer

<400> SEQUENCE: 1
tctcgggaac gctgaaga (b) performing three or more readout cycles to generate said temporal order of signal signatures, wherein said three or more readout cycles comprise:
  (i) a first readout cycle, comprising: (1) imaging said biological sample and detecting a first optical signal at said location, wherein said first optical signal is associated with said nucleic acid label of said detection reagent bound to said analyte at said location, thereby obtaining a first signal signature of said temporal order of signal signatures, and (2) removing said first optical signal from said location;
  (ii) a second readout cycle, comprising imaging said biological sample and detecting an absence of an optical signal at said location, thereby obtaining a second signal signature of said temporal order of signal signatures; and
  (iii) a third readout cycle, comprising imaging said biological sample and detecting a second optical signal at said location, wherein said second optical signal is associated with said nucleic acid label of said detection reagent bound to said analyte at said location, thereby obtaining a third signal signature of said temporal order of signal signatures; and
(c) using said temporal order of signal signatures to identify said analyte at said location of said biological sample.

2. The method of claim 1, wherein said nucleic acid label comprises a predetermined sequence and wherein said first readout cycle further comprises, prior to said imaging of (b)(i)(1), using a first decoder probe to associate a first optical label with said predetermined sequence.

3. The method of claim 2, wherein said third readout cycle further comprises, prior to said imaging of (b)(iii), using a second decoder probe to associate a second optical label with said predetermined sequence.

4. The method of claim 1, wherein said nucleic acid label comprises two or more predetermined sequences, wherein said first readout cycle further comprises, prior to said imaging of (b)(i)(1), using a first decoder probe to associate a first optical label with a first predetermined sequence of said two or more predetermined sequences, wherein said first decoder probe is complementary to and hybridizes with said first predetermined sequence, and wherein said imaging of (b)(i)(1) comprises detecting said first optical label at said location, thereby detecting said first optical signal at said location.

5. The method of claim 4, wherein said third readout cycle further comprises, prior to said imaging of (b)(iii), using a second decoder probe to associate a second optical label with a second predetermined sequence of said two or more predetermined sequences, wherein said first decoder probe is complementary to and hybridizes with said second predetermined sequence, and wherein said imaging of (b)(iii) comprises detecting said second optical label at said location, thereby detecting said second optical signal.

6. The method of claim 5, wherein, in (b)(i)(2), removing said first optical signal from said location comprises photobleaching, quenching, chemically degrading, bleaching, or oxidizing said first optical label.

7. The method of claim 5, wherein, in (b)(i)(2), removing said first optical signal from said location comprises washing or displacing said first decoder probe from said first predetermined sequence.

8. The method of claim 5, wherein, in (b)(i)(2), removing said first optical signal from said location comprises washing said first decoder probe from said first predetermined sequence, wherein said washing comprises heating said biological sample, varying a salt concentration of said biological sample, applying a detergent to said biological sample, applying a denaturant to said biological sample, or a combination thereof.

9. The method of claim 5, wherein, in (b)(i)(2), removing said first optical signal from said location comprises cleaving or enzymatically digesting said first decoder probe.

10. The method of claim 5, wherein said first decoder probe comprises a cleavable linker and wherein removing said first optical signal from said location comprises cleaving said cleavable linker.

11. The method of claim 5, wherein said first optical label is directly conjugated to said first decoder probe and wherein said second optical label is directly conjugated to said second decoder probe.

12. The method of claim 5, wherein said first optical label is indirectly attached to said first decoder probe and wherein said second optical label is indirectly attached to said second decoder probe.

13. The method of claim 5, wherein said first optical label is indirectly attached to said first decoder probe via a first intermediary molecule and said second optical label is indirectly attached to said second decoder probe via a second intermediary molecule.

14. The method of claim 5, wherein said first optical label is indirectly attached to said first decoder probe via a first binding molecule that hybridizes to said first decoder probe, and wherein said second optical label is indirectly attached to said second decoder probe via a second binding molecule that hybridizes to said second decoder probe.

15. The method of claim 14, wherein said first binding molecule is directly conjugated to said first optical label and wherein said second binding molecule is directly conjugated to said second optical label.

16. The method of claim 1, wherein said biological sample is a cell or tissue sample, wherein said analyte is a cellular nucleic acid analyte, wherein said detection reagent is a linear nucleic acid molecule, wherein said probe comprises a first sequence complementary to a second sequence of said cellular nucleic acid analyte, and wherein binding said detection reagent to said analyte comprises hybridizing said first sequence to said second sequence.

17. The method of claim 16, further comprising, prior to (b), circularizing said linear nucleic acid molecule to generate a circularized detection reagent and performing rolling circle amplification using said circularized detection reagent as a template.

18. The method of claim 17, wherein circularizing said linear nucleic acid molecule comprises use of a ligase.

19. The method of claim 1, wherein said biological sample is immobilized on a solid support.

20. The method of claim 19, wherein said solid support does not comprise discrete sites configured to attach to beads.

21. The method of claim 19, wherein said solid support comprises discrete sites configured to attach to or associate with beads.

22. The method of claim 19, wherein said solid support is a planar substrate.

23. The method of claim 1, wherein said biological sample is a tissue section on a microscopy slide.

24. The method of claim 23, further comprising, prior to (a), permeabilizing said tissue section.

25. The method of claim 1, wherein said first readout cycle, said second readout cycle, and said third readout cycle are performed sequentially.

26. A method for nucleic acid analysis, comprising:
(a) providing a cell or tissue sample, wherein said cell or tissue sample is attached to a solid support, and wherein said cell or tissue sample comprises a target nucleic acid molecule at a location of said cell or tissue sample;
(b) permeabilizing said cell or tissue sample attached to said solid support;
(c) binding a detection reagent to said target nucleic acid molecule at said location of said cell or tissue sample, wherein said detection reagent comprises a nucleic acid molecule comprising (i) a probe sequence complementary to a sequence of said target nucleic acid molecule, which probe sequence hybridizes with said sequence of said target nucleic acid molecule and (ii) a nucleic acid tag comprising a first predetermined sequence and a second predetermined sequence, wherein said nucleic acid tag does not bind to said target nucleic acid molecule, and wherein said detection reagent is identifiable by a temporal order of signal signatures associated with said nucleic acid tag;
(d) performing three or more readout cycles to generate said temporal order of signal signatures, wherein said temporal order of signal signatures comprises a first signal signature, a second signal signature, and a third signal signature, and wherein said three or more readout cycles comprise:
  (i) a first readout cycle, comprising (1) using a first decoder probe to associate a first fluorescent label with said nucleic acid tag of said detection reagent bound to said target nucleic acid molecule at said location, wherein said first decoder probe is complementary to and hybridizes with said first predetermined sequence; (2) imaging said cell or tissue sample and detecting said first fluorescent label at said location, thereby obtaining said first signal signature; and (3) removing said first fluorescent label from said location;
  (ii) a second readout cycle, comprising imaging said cell or tissue sample and detecting an absence of a fluorescent signal associated with said nucleic acid tag of said detection reagent bound to said target nucleic acid molecule at said location, thereby obtaining said second signal signature; and
  (iii) a third readout cycle, comprising (1) using a second decoder probe to associate a second fluorescent label with said nucleic acid tag of said detection reagent bound to said target nucleic acid molecule at said location, wherein said second decoder probe is complementary to and hybridizes with said second predetermined sequence; and (2) imaging said cell or tissue sample and detecting said second fluorescent label at said location, thereby obtaining said third signal signature; and
(e) using said temporal order of signal signatures generated at said location to identify said target nucleic acid at said location of said cell or tissue sample.

27. The method of claim 26, wherein said solid support does not comprise discrete sites configured to attach to beads.

28. The method of claim 26, wherein said solid support comprises discrete sites configured to attach to or associate with beads.

29. The method of claim 26, wherein said cell or tissue sample is a tissue section on a microscopy slide.

30. The method of claim 26, wherein said first readout cycle, said second readout cycle, and said third readout cycle are performed sequentially.

31. The method of claim 1, wherein said first readout cycle, said second readout cycle, and said third readout cycle are performed in any order.

32. The method of claim 26, wherein said first readout cycle, said second readout cycle, and said third readout cycle are performed in any order.

33. The method of claim 16, wherein said cellular nucleic acid analyte is a deoxyribonucleic acid (DNA) molecule.

34. The method of claim 16, wherein said cellular nucleic acid analyte is a ribonucleic acid (RNA) molecule.

35. The method of claim 34, wherein said RNA molecule is a messenger RNA molecule.

36. The method of claim 34, wherein said RNA molecule is a microRNA (miRNA) molecule.

37. The method of claim 1, wherein said probe comprises an antibody or an antigen-binding fragment of an antibody.

38. The method of claim 37, wherein said analyte is a protein.

39. The method of claim 5, wherein said first optical label and said second optical label are covalently attached to said first decoder probe and said second decoder probe, respectively, via a linker.

40. The method of claim 5, wherein said first optical label comprises a first fluorescent molecule and said second optical label comprises a second fluorescent molecule.

41. The method of claim 40, wherein said first fluorescent molecule and said second fluorescent molecule have the same fluorescent color.

42. The method of claim 40, wherein said first fluorescent molecule and said second fluorescent molecule have different fluorescent colors.

43. The method of claim 2, wherein said predetermined sequence is 5-50 nucleotides in length.

44. The method of claim 5, wherein said first predetermined sequence is 5-50 nucleotides in length and said second predetermined sequence is 5-50 nucleotides in length.

45. The method of claim 23, wherein said tissue section is a fixed, paraffin-embedded tissue section.

46. The method of claim 5, wherein said biological sample is a cell or tissue sample, wherein said analyte is a messenger ribonucleic acid (mRNA) molecule, wherein said detection reagent is a nucleic acid molecule comprising a probe sequence complementary to a sequence of said mRNA molecule, which probe sequence hybridizes with said sequence, and wherein said nucleic acid label does not hybridize with said mRNA molecule.

47. The method of claim 44, wherein said biological sample is a tissue section on a slide.

48. The method of claim 46, wherein said first predetermined sequence is 550 nucleotides in length and wherein said second predetermined sequence is 5-50 nucleotides in length.

49. The method of claim 48, wherein said first decoder probe is 5-50 nucleotides in length and wherein said second decoder probe is 5-50 nucleotides in length.

50. The method of claim 48, wherein (b)(i)(2) comprises cleaving said first decoder probe thereby removing said first optical signal from said location.

51. The method of claim 50, wherein said first decoder probe comprises a cleavable linker and wherein removing said first optical signal from said location comprises cleaving said cleavable linker.

52. The method of claim 48, wherein removing said first optical signal from said location further comprises washing said biological sample.

53. The method of claim 52, wherein said washing further comprises heating said biological sample, varying a salt concentration of said biological sample, applying a detergent to said biological sample, applying a denaturant to said biological sample, or a combination thereof.

54. The method of claim 48,
wherein said nucleic acid label comprises three or more predetermined sequences comprising said first predetermined sequence, said second predetermined sequence, and a third predetermined sequence 5-50 nucleotides in length;
wherein (b) comprises performing four or more readout cycles to detect said temporal order of signal signatures; wherein said four or more readout cycles comprises said first readout cycle, said second readout cycle, said third readout cycle, and a fourth readout cycle;
wherein said third readout cycle comprises, after said imaging of (b)(iii), removing said second optical signal from said location; and
wherein said fourth readout cycle comprises: (1) using a third decoder probe to associate a third optical label with said third predetermined sequence, wherein said third decoder probe is complementary to and hybridizes with said third predetermined sequence, and (2) imaging said biological sample to detect said third optical label at said location, thereby detecting said third optical signal at said location, and thereby obtaining a fourth signal signature of said temporal order of signal signatures.

55. The method of claim 54, wherein said first readout cycle, said second readout cycle, said third readout cycle, and said fourth readout cycle are performed in any order.

56. The method of claim 54, wherein said first readout cycle, said second readout cycle, said third readout cycle, and said fourth readout cycle are performed sequentially.

57. The method of claim 54, wherein (b) comprises performing five or more readout cycles to detect said temporal order of signal signatures; wherein said five or more readout cycles comprises said first readout cycle, said second readout cycle, said third readout cycle, said fourth readout cycle, and a fifth readout cycle; wherein said fourth readout cycle further comprises, after imaging said biological sample to detect said third optical label at said location, removing said third optical signal from said location; and
wherein said fifth readout cycle comprises imaging said biological sample and detecting an absence of an optical signal at said location, thereby obtaining a fifth signal signature of said temporal order of signal signatures.

58. The method of claim 57, wherein said first readout cycle, said second readout cycle, said third readout cycle, said fourth readout cycle, and said fifth readout cycle are performed in any order.

59. The method of claim 57, wherein said first readout cycle, said second readout cycle, said third readout cycle, said fourth readout cycle, and said fifth readout cycle are performed sequentially.

60. The method of claim 26, wherein in (d)(i)(3), removing said first fluorescent label from said location comprises photo-bleaching, quenching, chemically degrading, bleaching, or oxidizing said first fluorescent label.

61. The method of claim 26, wherein in (d)(i)(3), removing said first fluorescent label from said location comprises washing said first decoder probe from said first predetermined sequence, wherein said washing comprises heating said biological sample, varying a salt concentration of said biological sample, applying a detergent to said biological sample, applying a denaturant to said biological sample, or a combination thereof.

62. The method of claim 26, wherein in (d)(i)(3), removing said first fluorescent label from said location comprises displacing said first decoder probe from said first predetermined sequence using a displacement oligonucleotide.

63. The method of claim 62, wherein said first predetermined sequence comprises a toehold sequence and wherein said displacement oligonucleotide hybridizes to said toehold sequence and displaces said first decoder probe from said first predetermined sequence.

64. The method of claim 26, wherein in (d)(i)(3), removing said first fluorescent label from said location comprises cleaving or enzymatically digesting said first decoder probe.

65. The method of claim 26, wherein said first decoder probe comprises a cleavable linker and wherein removing said first fluorescent label from said location comprises cleaving said cleavable linker.

66. The method of claim 26, wherein said first fluorescent label is directly conjugated to said first decoder probe and wherein said second fluorescent label is directly conjugated to said second decoder probe.

67. The method of claim 26, wherein said first fluorescent label is indirectly attached to said first decoder probe and wherein said second fluorescent label is indirectly attached to said second decoder probe.

68. The method of claim 67, wherein said first fluorescent label is indirectly attached to said first decoder probe via a first intermediary molecule and said second fluorescent label is indirectly attached to said second decoder probe via a second intermediary molecule.

69. The method of claim 67, wherein said first fluorescent label is indirectly attached to said first decoder probe via a first binding molecule that hybridizes to said first decoder probe, and wherein said second fluorescent label is indirectly attached to said second decoder probe via a second binding molecule that hybridizes to said second decoder probe.

70. The method of claim 69, wherein said first binding molecule is directly conjugated to said first fluorescent label and wherein said second binding molecule is directly conjugated to said second fluorescent label.

71. The method of claim 26, wherein said first fluorescent molecule and said second fluorescent molecule have the same fluorescent color.

72. The method of claim 26, wherein said first fluorescent molecule and said second fluorescent molecule have different fluorescent colors.

73. The method of claim 26, wherein said first predetermined sequence is 5-50 nucleotides in length and said second predetermined sequence is 5-50 nucleotides in length.

74. The method of claim 26, wherein said cell or tissue sample is a tissue section on a microscopy slide.

75. The method of claim 74, wherein said tissue section is a fixed, paraffin-embedded tissue section.

76. The method of claim 26, wherein said nucleic acid tag further comprises a third predetermined sequence; wherein said third readout cycle further comprises, after said imaging in (d)(iii)(2), removing said second fluorescent label from said location;
wherein (d) comprises performing four or more readout cycles to detect said temporal order of signal signatures; wherein said temporal order of signal signatures further comprises a fourth signal signature; and
wherein said four or more readout cycles comprises said first readout cycle, said second readout cycle, said third readout cycle, and a fourth readout cycle comprising (1) using a third decoder probe to associate a third fluorescent label with said nucleic acid tag of said detection reagent bound to said target nucleic acid molecule at said location, wherein said third decoder probe is complementary to and hybridizes with said third predetermined sequence; and (2) imaging said cell or tissue sample to detect said third fluorescent label at said location, thereby obtaining said fourth signal signature.

77. The method of claim 76, wherein said first readout cycle, said second readout cycle, said third readout cycle, and said fourth readout cycle are performed in any order.

78. The method of claim 76, wherein said first readout cycle, said second readout cycle, said third readout cycle, and said fourth readout cycle are performed sequentially.

79. The method of claim 76, wherein (d) comprises performing five or more readout cycles to detect said temporal order of signal signatures; wherein said temporal order of signal signatures further comprises a fifth signal signature; wherein said fourth readout cycle further comprises, after imaging said cell or tissue sample to detect said third fluorescent label at said location, removing said third fluorescent label from said location; wherein said five or more readout cycles comprises said first readout cycle, said second readout cycle, said third readout cycle, said fourth readout cycle, and a fifth readout cycle comprising imaging said cell or tissue sample and detecting an absence of a fluorescent signal associated with said nucleic acid tag of said detection reagent bound to said target nucleic acid molecule at said location, thereby obtaining said fifth signal signature.

80. The method of claim 79, wherein said first readout cycle, said second readout cycle, said third readout cycle, said fourth readout cycle, and said fifth readout are performed in any order.

81. The method of claim 79, wherein said first readout cycle, said second readout cycle, said third readout cycle, said fourth readout cycle, and said fifth readout are performed sequentially.

82. The method of claim 1, further comprising, after said third readout cycle, removing said second optical signal from said location.

* * * * *

UNITED STATES PATENT AND TRADEMARK OFFICE
CERTIFICATE OF CORRECTION

PATENT NO. : 11,293,052 B2
APPLICATION NO. : 17/238682
DATED : April 5, 2022
INVENTOR(S) : Church et al.

Page 1 of 1

It is certified that error appears in the above-identified patent and that said Letters Patent is hereby corrected as shown below:

In the Specification

Column 1, under STATEMENT OF GOVERNMENT INTERESTS, Line 35-37:
Please delete "This invention was made with Government support under grant number 1P50HG005550 awarded by NHGRI. The Government has certain rights in the invention." and insert --This invention was made with government support under HG005550 awarded by National Institutes of Health (NIH). The government has certain rights in this invention.--

Signed and Sealed this
Twenty-seventh Day of September, 2022

Katherine Kelly Vidal
*Director of the United States Patent and Trademark Office*